(12) United States Patent
Hustedt et al.

(10) Patent No.: US 11,622,796 B2
(45) Date of Patent: Apr. 11, 2023

(54) IMPLANT AND METHOD FOR LONG BONE FIXATION

(71) Applicant: MeduLoc, LLC, Del Mar, CA (US)

(72) Inventors: Joshua Hustedt, Phoenix, AZ (US); Benjamin Arnold, San Diego, CA (US); Brian Bowman, Carlsbad, CA (US); Kristen Ybarra, Yuma, AZ (US)

(73) Assignee: MeduLoc, LLC, Del Mar, CA (US)

( * ) Notice: Subject to any disclaimer, the term of this patent is extended or adjusted under 35 U.S.C. 154(b) by 260 days.

(21) Appl. No.: 17/012,852

(22) Filed: Sep. 4, 2020

(65) Prior Publication Data

US 2020/0397488 A1 Dec. 24, 2020

Related U.S. Application Data

(63) Continuation of application No. 15/699,821, filed on Sep. 8, 2017, now Pat. No. 10,813,673.
(Continued)

(51) Int. Cl.
*A61B 17/72* (2006.01)
*A61B 17/92* (2006.01)
(Continued)

(52) U.S. Cl.
CPC ...... *A61B 17/7266* (2013.01); *A61B 17/7233* (2013.01); *A61B 17/7291* (2013.01); *A61B 17/80* (2013.01); *A61B 17/8863* (2013.01); *A61B 17/8872* (2013.01); *A61B 17/8875* (2013.01); *A61B 17/921* (2013.01); *A61B 17/1604* (2013.01); *A61B 17/1717* (2013.01); *A61B 17/7225* (2013.01); *A61B 17/7275* (2013.01)

(58) Field of Classification Search
CPC ............... A61B 17/72; A61B 17/7233; A61B 17/7258–7275
See application file for complete search history.

(56) References Cited

U.S. PATENT DOCUMENTS 3,759,257 A 9/1973 Fischer
3,760,802 A 9/1973 Fischer
(Continued)

FOREIGN PATENT DOCUMENTS

CN 104665908 A 6/2015
EP 0689800 A2 1/1996
(Continued)

OTHER PUBLICATIONS

Supplementary EP Search Report for corresponding EP application No. 17849660, dated Jul. 23, 2020, 4 pages.
(Continued)

*Primary Examiner* — Eduardo C Robert
*Assistant Examiner* — Michelle C Eckman
(74) *Attorney, Agent, or Firm* — Acuity IP, LLC; Nathan S. Cassell

(57) ABSTRACT

An implant and method for fixation of long bones. The implant provides rotational, longitudinal, and bending stability. The implant comprises one or more elongated members that span the intramedullary cavity of a long bone, a distal tip that expands radially relative to the long axis of the implant, and a locking mechanism at the proximal end of the implant.

31 Claims, 46 Drawing Sheets

Related U.S. Application Data

(60) Provisional application No. 62/385,044, filed on Sep. 8, 2016, provisional application No. 62/450,700, filed on Jan. 26, 2017.

(51) Int. Cl.
*A61B 17/88* (2006.01)
*A61B 17/80* (2006.01)
*A61B 17/16* (2006.01)
*A61B 17/17* (2006.01)

(56) References Cited

U.S. PATENT DOCUMENTS

| | | | |
|---|---|---|---|
| 3,779,239 A * | 12/1973 | Fischer | A61B 17/7225 606/63 |
| 3,799,239 A | 3/1974 | Dumont-Fillon et al. | |
| 4,091,806 A * | 5/1978 | Aginsky | A61B 17/7225 606/63 |
| 4,227,518 A | 10/1980 | Aginsky | |
| 5,441,500 A | 8/1995 | Seidel et al. | |
| 6,168,597 B1 | 1/2001 | Biedermann | |
| 6,224,600 B1 * | 5/2001 | Protogirou | A61B 17/7266 606/68 |
| 6,575,973 B1 | 6/2003 | Shekalim | |
| 7,601,152 B2 | 10/2009 | Levy | |
| 7,909,825 B2 | 3/2011 | Saravia | |
| 8,337,495 B1 | 12/2012 | Powlan | |
| 8,460,293 B2 | 6/2013 | Coati | |
| 9,028,496 B2 | 5/2015 | Tontz | |
| 9,060,809 B2 | 6/2015 | Tipirneni | |
| 9,452,003 B2 | 9/2016 | Voor | |
| 9,498,266 B2 | 11/2016 | McCormick | |
| 9,532,789 B2 | 1/2017 | Coope | |
| 9,545,274 B2 | 1/2017 | McCormick | |
| 9,913,727 B2 | 3/2018 | Thommen | |
| 9,968,349 B2 | 5/2018 | Heaven | |
| 10,813,673 B2 | 10/2020 | Hustedt et al. | |
| 2002/0068939 A1 | 6/2002 | Levy et al. | |
| 2002/0161369 A1 | 10/2002 | Bramlet | |
| 2002/0165544 A1 * | 11/2002 | Perren | A61B 17/7266 606/63 |
| 2003/0130660 A1 * | 7/2003 | Levy | A61B 17/744 606/63 |
| 2004/0138663 A1 | 7/2004 | Kosashvili et al. | |
| 2004/0230193 A1 | 11/2004 | Cheung | |
| 2005/0216007 A1 | 9/2005 | Woll | |
| 2006/0229617 A1 | 10/2006 | Meller | |
| 2006/0264950 A1 | 11/2006 | Nelson | |
| 2007/0100342 A1 | 5/2007 | Green | |
| 2007/0173834 A1 | 7/2007 | Thakkar | |
| 2008/0262495 A1 | 10/2008 | Coati | |
| 2008/0287851 A1 | 11/2008 | Stoneburner | |
| 2009/0005782 A1 * | 1/2009 | Chirico | A61B 17/1617 606/300 |
| 2009/0182336 A1 * | 7/2009 | Brenzel | A61B 17/869 606/62 |
| 2009/0216232 A1 | 8/2009 | Buford, III | |
| 2010/0023010 A1 | 1/2010 | Nelson | |
| 2010/0023011 A1 | 1/2010 | Nakamura | |
| 2010/0087820 A1 | 4/2010 | Mantovani | |
| 2010/0312292 A1 | 12/2010 | Tipirneni | |
| 2011/0077651 A1 | 3/2011 | Lozier et al. | |
| 2011/0137312 A1 * | 6/2011 | Mantovani | A61B 17/7266 606/63 |
| 2012/0065638 A1 | 3/2012 | Moore | |
| 2012/0123415 A1 | 5/2012 | Vienney | |
| 2012/0226326 A1 | 9/2012 | Overes | |
| 2012/0239038 A1 | 9/2012 | Saravia | |
| 2013/0012942 A1 | 1/2013 | Nelson | |
| 2013/0079776 A1 | 3/2013 | Zwirkoski | |
| 2013/0116693 A1 | 5/2013 | Nelson | |
| 2013/0131678 A1 | 5/2013 | Dahners | |
| 2013/0158552 A1 * | 6/2013 | Overes | A61B 17/7258 606/64 |
| 2013/0238036 A1 | 9/2013 | Sinha | |
| 2013/0253661 A1 * | 9/2013 | D'Agostino | A61L 27/443 428/377 |
| 2013/0325007 A1 | 12/2013 | Beyar | |
| 2014/0114312 A1 | 4/2014 | Krause | |
| 2014/0309636 A1 | 10/2014 | Meek | |
| 2015/0073413 A1 | 3/2015 | Palmer et al. | |
| 2015/0257800 A1 | 9/2015 | Harshman | |
| 2015/0374411 A1 * | 12/2015 | Ehmke | A61B 17/686 606/329 |
| 2016/0051295 A1 | 2/2016 | Nakamura et al. | |
| 2016/0089189 A1 | 3/2016 | Buscaglia | |
| 2016/0317200 A1 | 11/2016 | Hoogervorst | |
| 2017/0238977 A1 | 8/2017 | Harshman | |
| 2018/0064475 A1 | 3/2018 | Polat | |
| 2018/0078293 A1 | 3/2018 | Hustedt | |
| 2019/0105087 A1 | 4/2019 | Sommers | |
| 2019/0120282 A1 | 4/2019 | Krause | |

FOREIGN PATENT DOCUMENTS

| | | |
|---|---|---|
| WO | 2012010184 A1 | 1/2012 |
| WO | 2015090954 A1 | 6/2015 |

OTHER PUBLICATIONS

Partial supplementary European search report with provisional opinion for corresponding EP application No. 17849660, dated Mar. 25, 2020, 10 pages.

PCT/US2017/050781 International Search Report and Written Opinion dated Jan. 18, 2018.

\* cited by examiner

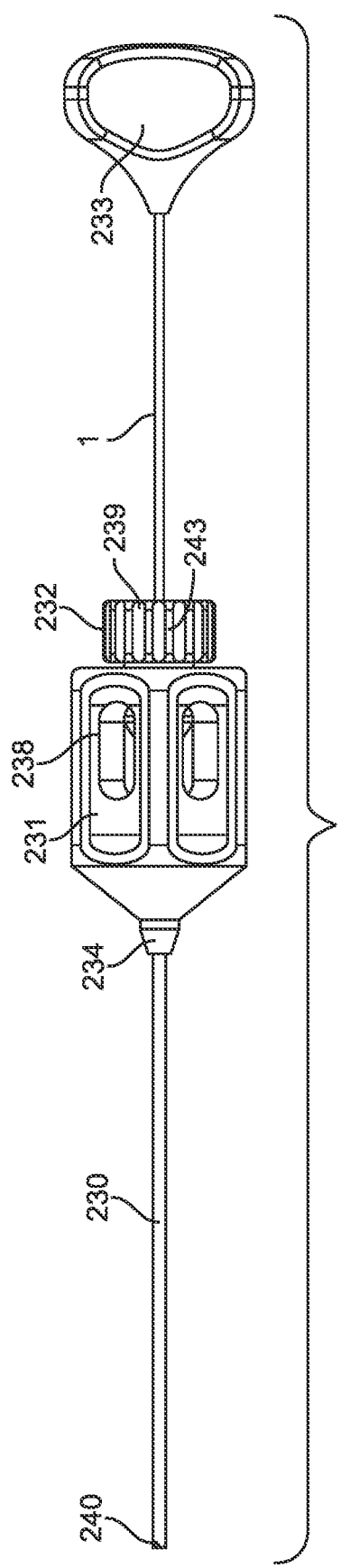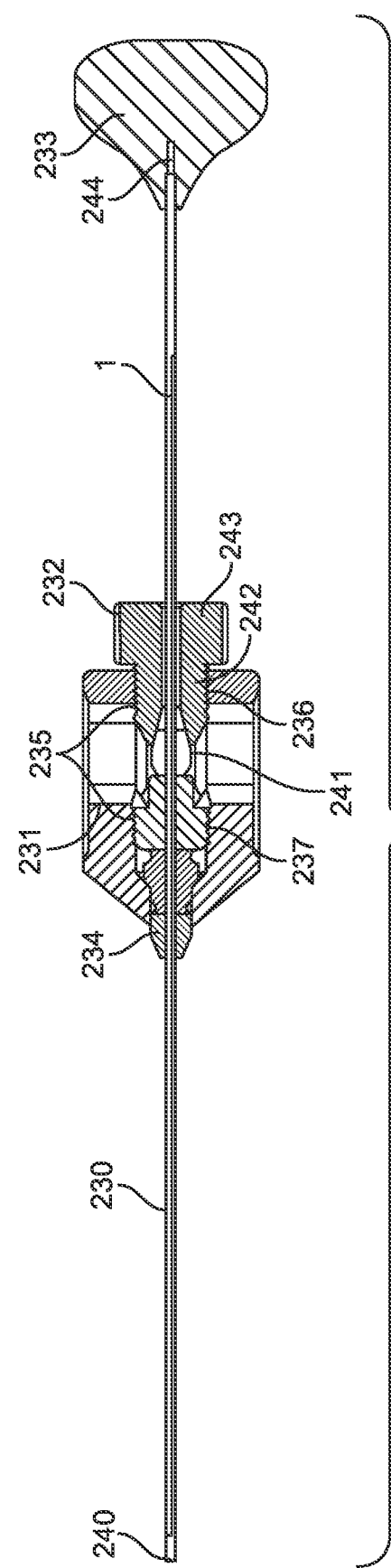
FIG. 35A
FIG. 35B

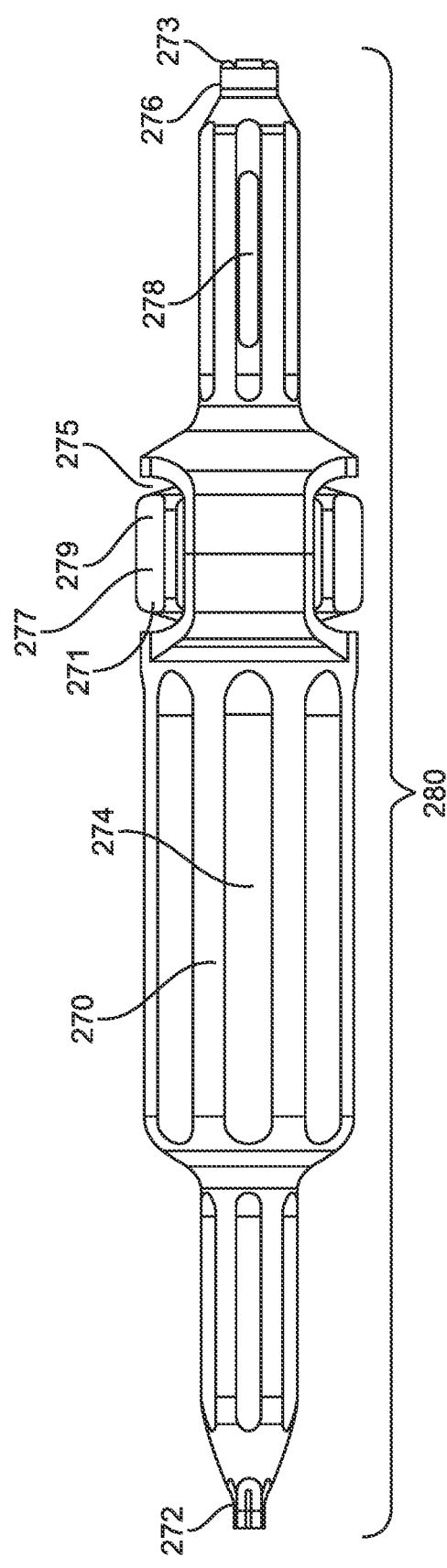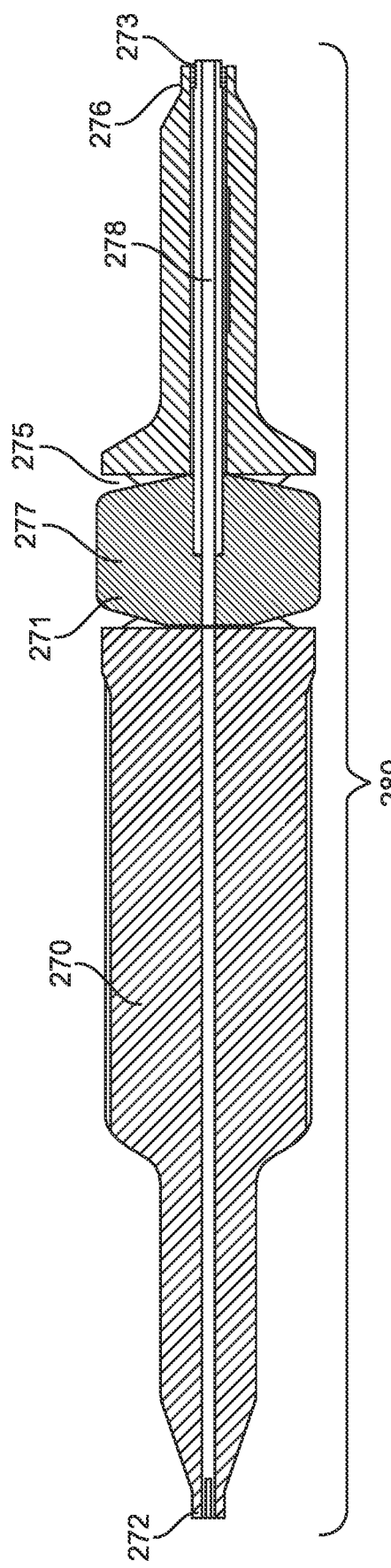
FIG. 37A
FIG. 37B

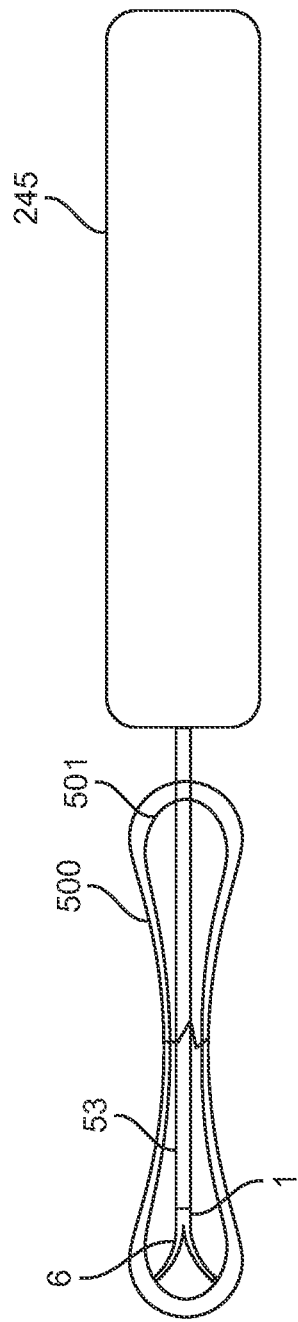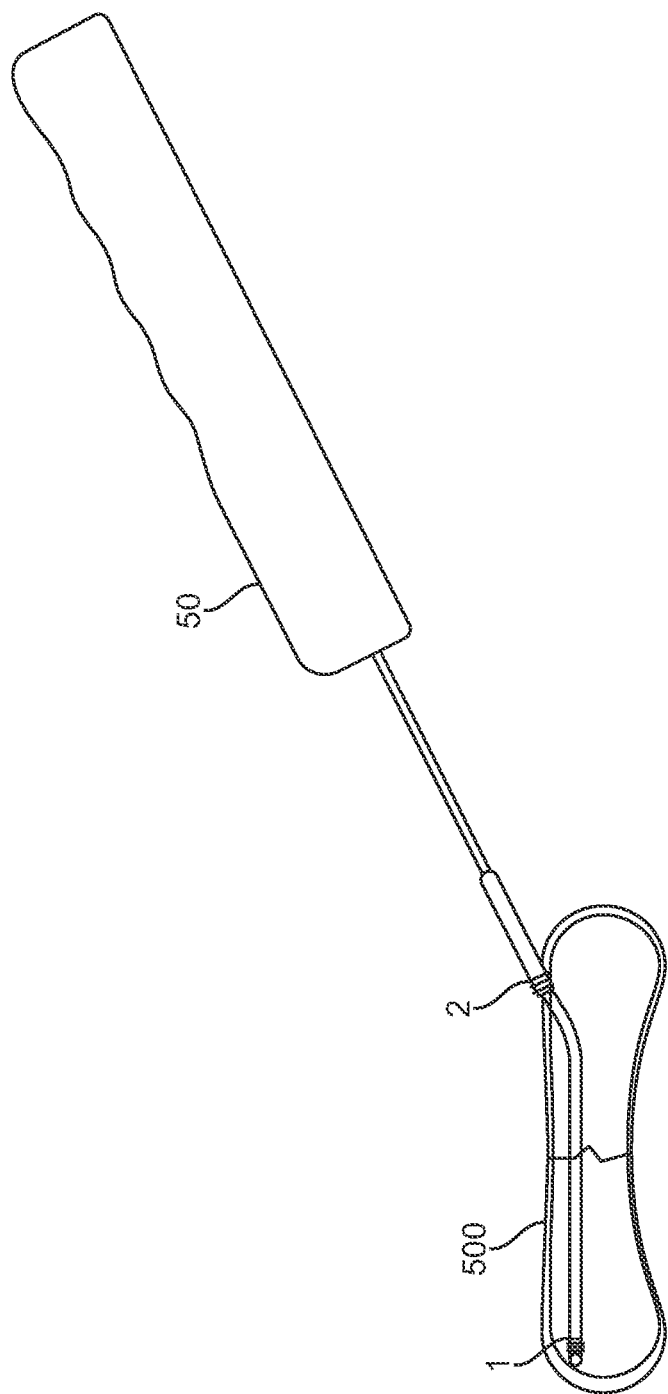

IMPLANT AND METHOD FOR LONG BONE FIXATION

CROSS-REFERENCE TO RELATED APPLICATIONS

This is a continuation application of U.S. patent application Ser. No. 15/699,821 filed Sep. 8, 2017, which is a non-provisional of, and claims the benefit of U.S. Provisional Patent Application Nos. 62/385,044 filed Sep. 8, 2016, and 62/450,700 filed Jan. 26, 2017. The entire content of each of the above referenced applications is incorporated herein by reference.

BACKGROUND OF THE INVENTION

Fractures of long bones are currently treated with a variety of internal fixation devices, including plates which are fixated to the surface of a bone with screws, nails or wires running inside the medullary canal, and/or screws affixing both ends of a fractured bone together. In general, fracture fixation using methods listed above or others may provide longitudinal (along the long axis of the bone), transverse (across the long axis of the bone), and rotational (about the long axis of the bone) stability. Fracture fixation may also preserve normal function during and after healing.

Plates are one traditional method of treating long bone fractures. A plate is placed along the length of the bone and screws are inserted in the bone generally perpendicular to the length of bone and on each side of the fracture. Such a method is relatively invasive when compared to other common methods due to large soft tissue dissection needed for plate placement. Plates can handle difficult fracture patterns; however, proper alignment and repair with this method is strongly dependent on fracture type and physician skill set. Plates have additional issues in smaller bones such as the metacarpals. Plates in these bones are more likely to have issues with tendon adhesion due to the raised surface of the plate, prevalence of tendons, and the tight anatomy which may cause range of motion issues in the hand after surgery. This method also creates a larger scar than other methods.

Screws are another method for treating fractures. In this method one or multiple screws are affixed to the bone across the fracture. Although this method is less invasive than plates, it is only able to be done on spiral and oblique fractures and is a technically difficult procedure.

Intramedullary fixation is another traditional method for treating long bone fractures, affixing the bone fracture using intramedullary nails or wires, without disturbing the periosteum of the bone. Such a method may be accomplished in a closed manner, and the fractured bone may be functionally used (including weight bearing in some cases) during healing. The surgical approach for insertion of intramedullary nails or wires varies slightly for each bone and is well described in the orthopedic literature.

Some of the challenges associated with conventional intramedullary fixation methods include lack of rotational stability and/or undesired migration of nails and wires. Intramedullary fixation methods may also introduce interlocking screws across the nail for larger bones, creating some disadvantages. Specifically, conventional intramedullary fixation nails for long bones include a rigid structure that may be locked at the ends of the nail with screws applied transversely through the bone walls and the nail itself. This step greatly increases the complexity of the surgery and requires extra incisions, and requires additional X-rays.

It would therefore be desirable to provide improved fracture fixation devices and methods that overcome some of the challenges of existing treatments. The embodiments described herein address at least some of these challenges.

SUMMARY OF THE INVENTION

The present disclosure generally relates to medical devices and methods and more particularly relates to implants and methods for fixation of long bones.

One embodiment of the implant comprises an elongate member with a distal end and a proximal end. The distal end may comprise a distal tip that changes shape when inserted into a medullary cavity of a long bone with a fracture. The distal tip may be designed to prevent rotation and translation of one end of the bone and one of a variety of locking mechanisms for securing the proximal end of the implant to the other end of the bone.

Locking mechanisms may comprise a plate attached adjacent a surface along the length of the long bone towards the proximal end. The locking mechanism may further comprise one or more pins that secure the plate to the bone. Additional locking mechanisms may lock the proximal end of the implant to the bone with or without the use of a plate. These solutions may comprise a cannulated locking screw or stapling an exposed section of the elongate member to the surface of the bone. Alternatively, or in combination, the elongate member may be fixated inside the bone using an expanding proximal end. This end may be shape memory wire and expand immediately upon insertion, may be expanded upon removal of an outer sheath, or may be expanded with the aid of a surgeon.

Optionally, in any embodiment, the elongate member may be sized for the bone anatomy or may be cut to length.

Optionally, in any embodiment, the distal tip of the fixation implant may have one or more slots extending from the distal end proximally such that the two or more arms may expand into arcuate shapes having an increased profile for anchoring the distal tip in the long bone. The distal end may have cutouts along its length that may expand into arcuate shapes having an increased profile for anchoring the distal tip in the long bone.

Optionally, in any embodiment, the distal tip of the fixation implant may expand into an arcuate shape having an increased profile for anchoring the distal tip in the long bone. The arcuate shape may be any shape including but not limited to a ring, an undulating shape, a J-shape, or a Shepherd's crook. The distal tip may have one or more grooves for improved bone fixation.

Optionally, in any embodiment, the distal end of the fixation implant may comprise a radially-expanding coil having an increased profile for anchoring the distal tip in the long bone.

Optionally, in any embodiment, the locking mechanism may comprise a plate that compresses the elongate member to the bone.

Optionally, in any embodiment, the locking mechanism may comprise a plate with a transverse hole and internal tang configured to receive the elongate member freely in one direction and inhibit translation in the opposite direction.

Optionally, in any embodiment, the locking mechanism may comprise two coupled plates with transverse holes that may be configured to receive the elongate member and hold the elongate member with a shear force when the transverse holes are offset.

Optionally, in any embodiment, the locking mechanism may comprise a bone screw and a set screw that is threadably engaged with the bone screw to clamp the elongate member therebetween. Implantation of the fixation device may include locking the device with the locking mechanism by threadably engaging a set screw with a bone screw thereby engaging the fixation implant therebetween.

Optionally, in any embodiment, the locking mechanism may comprise an anchor configured to receive and hold the proximal end of the implant and anchor to the bone.

Optionally in any embodiment, the locking mechanism may comprise one or more expanding ends on the proximal end to provide fixation. The proximal end configuration may take any form described herein as related to the distal end expanding configurations.

Optionally in any embodiment, the method of implanting the fixation implant may comprise expanding the implant. The implant may be expanded using shape memory wire that can expand when heated to body temperature, the implant may be naturally in its expanded state and be inserted under constraint, or the implant may be expanded manually by a surgeon using a pin, a threaded mechanism, or the like. The implant may also be plastically deformed to maintain its expanded shape.

Optionally, in any embodiment, the implant may be implanted using a set of custom instruments which may include but is not limited to an awl to access the intramedullary canal, a marker to indicate the point of entry, a reamer to create space in the intramedullary canal. an inserter with a sheath to insert the implant into the intramedullary canal in its unexpanded state, an impaction attachment to impact the inserter and implant into place, a driver to insert the locking mechanism, and a cutter to cut the implant to length.

Optionally, in any embodiment, the implant may be removed with one or more custom instruments which may include but is not limited to a removal instrument to snap over locking mechanism, ream bone around the locking mechanism, and pull the implant out of the intramedullary canal.

Optionally, in any embodiment, the elongate member may contract or shorten in order to compress the bone together.

These and other embodiments are described in further detail in the following description related to the appended drawing figures.

BRIEF DESCRIPTION OF THE DRAWINGS

Specific embodiments of the disclosed device, delivery systems, or methods will now be described with reference to the drawings. Nothing in this detailed description is intended to imply that any particular component, feature, or step is essential to the invention.

FIG. 35A shows a side view of an exemplary embodiment of an inserter.

FIG. 35B shows a cross-section view of an exemplary embodiment of an inserter.

FIG. 37A shows a side view of an exemplary embodiment of a driver.

FIG. 37B shows a cross-section view of an exemplary embodiment of a driver.

FIG. 45 shows a top view of an inserter retracting and an implant expanding.

FIG. 46 shows a side view of a locking mechanism being driven into a long bone by a driver.

DETAILED DESCRIPTION OF THE INVENTION

Specific embodiments of the disclosed device and method of use will now be described with reference to the drawings. Nothing in this detailed description is intended to imply that any particular component, feature, or step is essential to the invention.

It would be desirable to provide improved fracture fixation devices and methods that overcome some of the challenges of existing treatments. For example, it would be desirable to provide an intramedullary device that provides both rotational and longitudinal stability to a fractured bone. Additionally, it would be desirable to provide an intramedullary device that provides rotational stability without the addition of perpendicular screws. The embodiments described herein address at least some of these challenges.

Figure 1:
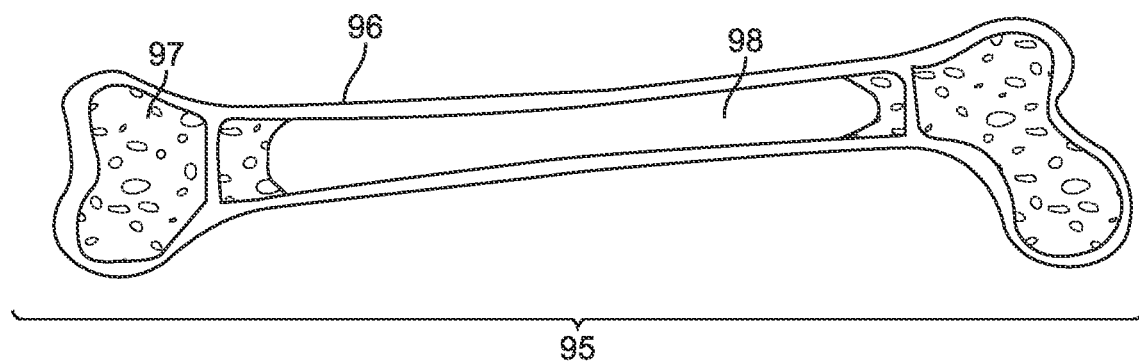
FIG. 1 shows a cross-section view of a long bone.

FIG. 1 shows an embodiment of a long bone 95. FIG. 1 illustrates an embodiment with optional features, any of which may be optionally used or substituted with other features in other embodiments discussed herein. Some embodiments of a long bone comprise cortical bone 96 which makes up the surface of the bone, softer cancellous bone 97 located at the ends of the long bone 95, and a medullary cavity 98 which runs through the center of the long axis of the bone and contains bone marrow. Some embodiments of long bones 95 may include, but are not limited to, metacarpal bones, metatarsal bones, phalanges, ulna, radius, clavicle, and fibula.

Figure 2:
FIG. 2 shows a side view of an exemplary embodiment of an implant for long bone fixation.

FIG. 2 shows a side view of an exemplary embodiment of an implant for long bone fixation. FIG. 2 illustrates an embodiment with optional features, any of which may be optionally used or substituted with other features in other embodiments discussed herein.

In some cases, an embodiment of an implant as provided in FIG. 2 may be implanted into a long bone (not pictured) to provide stability. The implant may comprise an elongate member 1 and a locking mechanism 2 comprising of a threaded component 3 and a driving component 4. The implant may be sized according to the local anatomy of a patient.

The elongate member 1 is preferably circular with a proximal end and distal end. The elongate member 1 may also be of ovular cross-section, square cross-section or any other shape. The elongate member 1 may have varying cross-sections across its length. The proximal end of the elongate member 1 may have at least one flat surface to interface with instruments (not pictured). The elongate member 1 is preferably a solid member but may also be hollow. The elongate member 1 may be available in various lengths to provide for different long bone uses and varying patient anatomy. In some cases, the elongate member 1 may have a length of 100 mm to 150 mm for use in a clavicle. In some cases, the elongate member 1 may have a length of 320 to 370 mm for use in a fibula. The elongate member 1 may be cut to length during implantation. The elongate member 1 may have various diameters to account for different long bone uses and varying patient anatomy. The elongate member 1 preferably has a diameter of 1 mm to 5 mm. More preferably, the elongate member 1 may have a diameter of 1.5 mm to 3.5 mm. The elongate member 1 is preferably rigid across its entire length. The elongate member 1 may be flexible along a portion or all of its length. The elongate 1 member may be nitinol. The elongate member 1 may be nickel titanium or any metal. Further details about the proximal and distal ends are discussed later.

The locking mechanism 2 is preferably tubular. The locking mechanism 2 may be any shape. The locking mechanism 2 is preferably cannulated. The locking mechanism 2 may have an inner diameter such that it can slide over the elongate member 1. The locking mechanism 2 may have a uniform outer diameter. The locking mechanism 2 may be tapered to have varying outer diameters. The locking mechanism 2 preferably has an outer diameter of 1 mm to 10 mm. More preferably, the locking mechanism 2 has an outer diameter of 1.5 mm to 5.5 mm. The locking mechanism 3 may have a threaded component 3. The locking mechanism 3 may also have any other configuration of components as described in further detail in this application. The threaded component 3 may have external threads to engage with bone. The threads may span the entire length of the threaded component 3. The threads may span partially across the length of the threaded component 3. The threaded component 3 may have a pitch of 0.2 to 1 mm. More preferably, the threaded component 3 may have a pitch of 0.3 mm to 0.6 mm. The threaded component 3 may have a cancellous bone thread profile. The threaded component 3 may have a cortical bone thread profile. The threaded component 3 may have varying thread profiles along its length. The locking mechanism 3 may have a driving component 4. The driving component 4 may have a bullet nose. The driving component 4 may have slots radially to increase the flexibility of the material in between.

The driving component 4 may slide over the proximal end of the elongate shaft 1. The threaded component 3 may slide over the proximal end of the driving component 4. The threaded component 3 and driving component 4 may be sized such that as the threaded component 3 slides over the driving component 4, the gap on the driving component 4 narrows to decrease the inner diameter, creating a tight fit between the elongate shaft 1 and the driving component 4. In this way, the elongate shaft 1 may be restricted axially and radially by the locking mechanism 2. The threaded component 3 may snap onto the driving component 2. The threaded component 3 may lock onto the driving component 2 in any way to maintain the rotational alignment between the two components. A more detailed description of the locking mechanism 2 components will be described later in this application.

Figure 3:
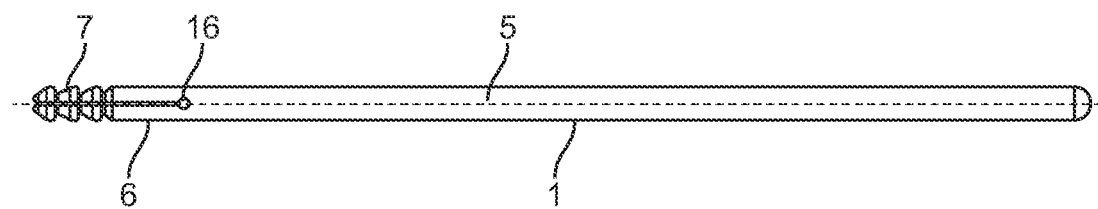
FIG. 3 shows a side view of an exemplary embodiment of the elongate member with an unexpanded distal end.

FIG. 3 shows a side view of an exemplary embodiment of the elongate member with an unexpanded distal end. FIG. 3 illustrates an embodiment with optional features, any of which may be optionally used or substituted with other features in other embodiments discussed herein. In particular, the elongate member in FIG. 3 is similar to the elongate member in FIG. 2. The elongate member 1 comprises a longitudinal axis 5, a distal end 6, and grooves 7. The distal end 6 may be tapered at the tip. The distal end 6 may be sectioned into two or more pieces with a slit extending longitudinally toward the proximal end. The distal end 6 sectioned pieces may be abutting each other such that there is no slit. The distal end 6 slit preferably extends proximally 5 mm to 30 mm along its length. More preferably, the distal end 6 slit extends 5 mm to 15 mm. The distal end 6 slit preferably has a width of 0 mm to 2 mm. The distal end 6 split may have a relief feature 16. The relief feature 16 may be a circular cutout. The distal end 6 may be sectioned by cutting, wire EDM, or any other method of separation. The distal end 6 of the elongate member 1 may have an expanded state and an unexpanded state such that the distal end 6 may expand inside the cancellous bone at the end of the long bone (not pictured) when implanted. The distal end 6 may be naturally in the expanded state. The distal end 6 may be naturally in the unexpanded state. The distal end 6 may be self-expanding. The distal end 6 may be expanded through mechanical, temperature, or other manipulation. FIG. 2 shows a drawing of the elongate member 1 in its unexpanded state. The elongate member 1 in its unexpanded state may have a constant overall outer diameter. The distal end 6 of the elongate member 1 may have one or more grooves 7 to aid in gripping cancellous bone. The grooves 7 may be circumferential rings. The grooves 7 may be sharp barbs. The grooves 7 may be cutouts of any shape. The grooves 7 may be disposed axially along the distal portion.

Figure 4:
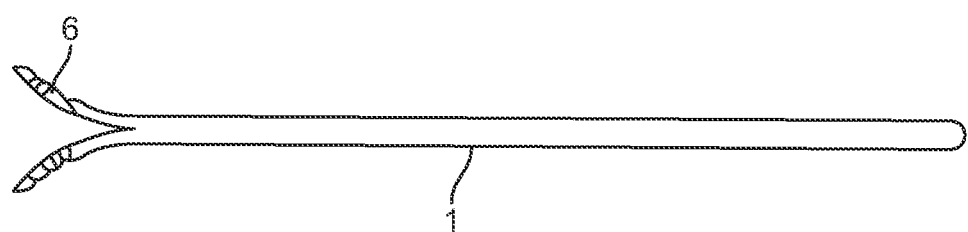
FIG. 4 shows a side view of another exemplary embodiment of the elongate member with an expanded distal end.

FIG. 4 shows a side view of another exemplary embodiment of the elongate member with an expanded distal end. FIG. 4 illustrates an embodiment with optional features, any of which may be optionally used or substituted with other features in other embodiments discussed herein. In particular, the elongate member 1 in FIG. 4 is similar to the elongate member in FIG. 2 and FIG. 3 in its expanded state. The distal end 6 tips may flare radially outward away from one another in its expanded state. The distal end 6 tips may have an arcuate shape. The distal end 6 may have any other shape. The distance between the distal end 6 tips in its expanded state is preferably 5 mm to 30 mm. More preferably, the distance between the distal end 6 may be 5 mm to 15 mm. The preferred expansion method is disclosed herein.

Figure 5:
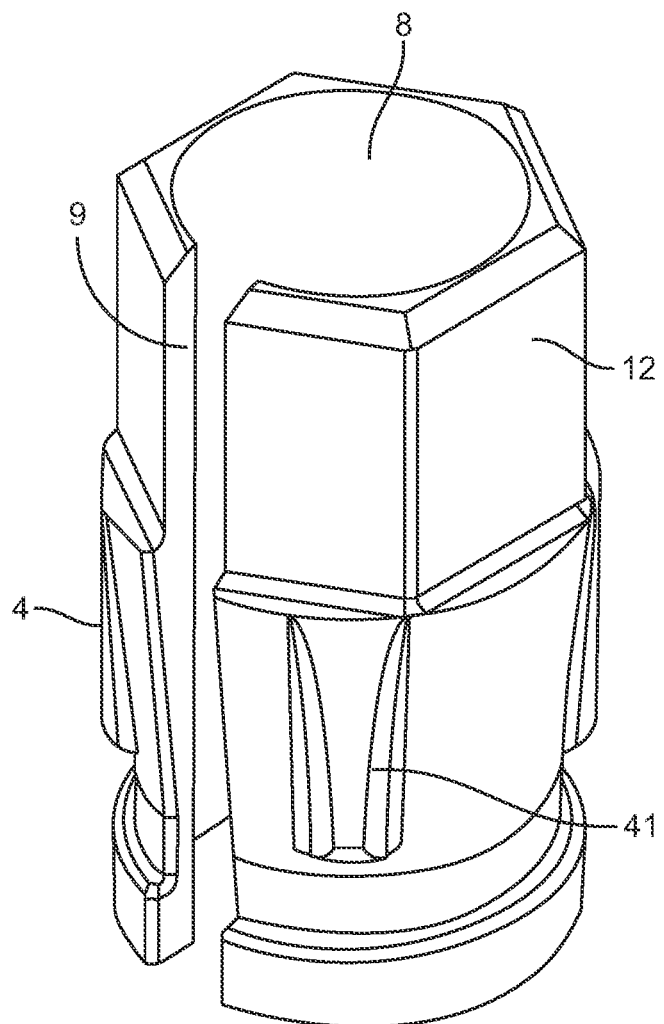
FIG. 5 shows a perspective view of an exemplary embodiment of a driving component.

FIG. 5 shows a perspective view of an exemplary embodiment of a driving component. FIG. 5 illustrates an embodiment with optional features, any of which may be optionally used or substituted with other features in other embodiments discussed herein. In particular, the driving component shown in FIG. 5 is similar to driving component 4, as described in FIG. 2, which may be used with any of the embodiments disclosed herein. The driving component 4 comprises a hole 8 which allows the driving component to slide over the elongate member (not pictured), a hexagonally extruded outer body 12 that allows the locking mechanism to be driven by a wrench or other driving device, and a gap 9 that preferably extends along the entire length of the driving component 4 and allows the hole 8 to decrease in diameter and maintain grip on the elongate member. The driving component 4 may also have a plurality of tabs 41 on its outer surface. Preferably there are one to six tabs 41. More preferably, there are one to four tabs 41. The tabs 41 may be of triangular shape. The tabs 41 may be any other shape. The tabs 41 may be located circumferentially around the driving component 4. The tabs 41 may be located near the distal end of the driving component 41. The tabs 41 may be oriented with the thick portion located distally. The tabs 41 may be oriented substantially parallel to the long axis of the driving component 4.

Figure 6:
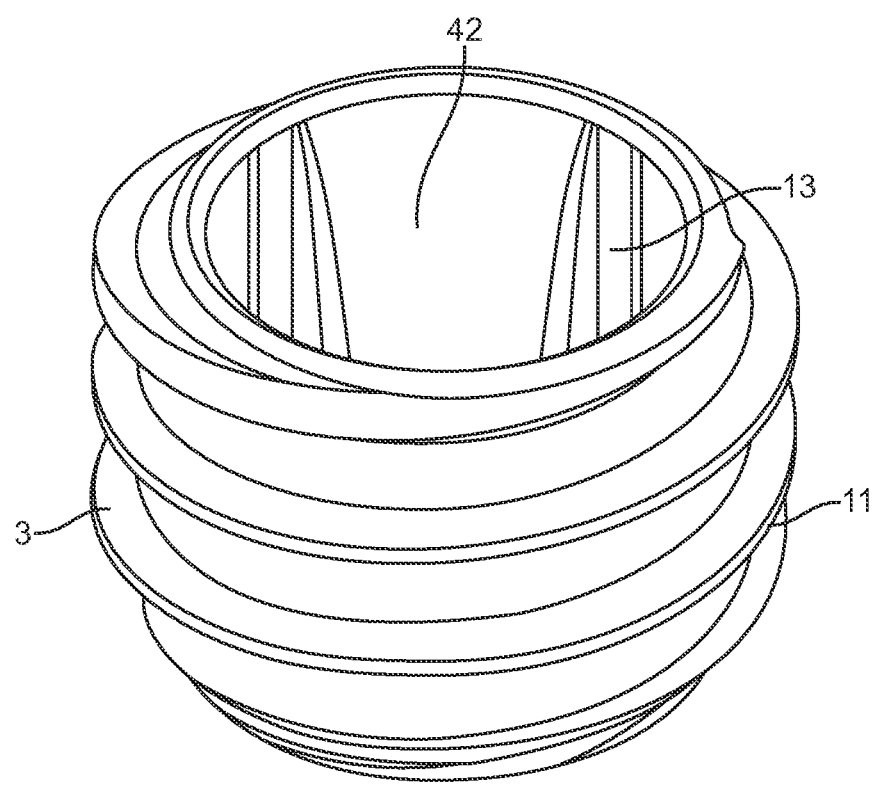
FIG. 6 shows a perspective view of an exemplary embodiment of a threaded component.

FIG. 6 shows a perspective view of an exemplary embodiment of a threaded component. FIG. 6 illustrates an embodiment with optional features, any of which may be optionally used or substituted with other features in other embodiments discussed herein. In particular, the threaded component shown in FIG. 6 is similar to threaded component 3, as described in FIG. 2, which may be used with any of the embodiments disclosed herein. The threaded component 3 may have a circular hole 42. The threaded component 3 may have a hole 42 of any shape. The hole 42 may be sized to receive the driving component (not pictured). The threaded component 3 may comprise external threads 11 to engage with the proximal end of the bone. The threaded component 3 may also comprise one or more internal recesses 13. The recesses 13 may be sized and shaped to receive the tabs on the driving component (not pictured). The recesses 13 may engage with the tabs to prevent rotational movement of the driving component with respect to the threaded component 3.

Figure 7:
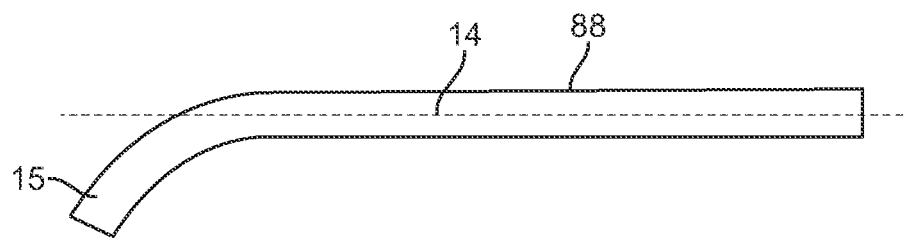
FIG. 7 shows a side view of an exemplary embodiment of the elongate member with an expanded distal end.

FIG. 7 shows a side view of an exemplary embodiment of the elongate member with an expanded distal end. FIG. 7 illustrates an embodiment with optional features, any of which may be optionally used or substituted with other features in other embodiments discussed herein. This embodiment comprises an elongate member 88, having a linear portion with a longitudinal axis 14, and a curved distal end 15 which can curve after implantation. The elongate member 88 is preferably tubular with a proximal end and distal end 15. The elongate member 88 may also be of ovular cross-section, square cross-section or any other shape. The elongate member 88 is preferably a solid member but may also be hollow. The elongate member 88 may be available in various lengths to provide for different long bone uses and varying patient anatomy. In some cases, the elongate member 88 may have a length of 100 mm to 150 mm for use in a clavicle. In some cases, the elongate member 88 may have a length of 320 to 370 mm for use in a fibula. The elongate member 88 may be cut to length during implantation. The elongate member 88 may have various diameters to account for different long bone uses and varying patient anatomy. The elongate member 88 preferably has a diameter of 1 mm to 5 mm. More preferably, the elongate member 88 may have a diameter of 1.5 mm to 3.5 mm. The elongate member 88 is preferably rigid across its entire length. The elongate member 88 may be flexible along a portion or all of its length. The elongate member 88 may be nitinol. The elongate member 88 may be nickel titanium or any metal. The elongate member 88 may be self-expanding or self-curving. The distal end 15 preferably curves proximally 5 mm to 30 mm. More preferably, the distal end 6 curve extends 5 mm to 15 mm. The distal end 15 preferably curves outwardly 2 mm to 20 mm. More preferably, the distal end 15 curves outwardly 2 mm to 8 mm. The distal end 15 of the elongate member 88 may have an expanded state and an unexpanded state such that the distal end 15 may expand or curve inside the cancellous bone at the end of the long bone (not pictured) when implanted. The distal end 15 may be naturally in the expanded state. The distal end 15 may be naturally in the unexpanded state. The distal end 6 may be expanded through mechanical, temperature, or other manipulation.

Figure 8:
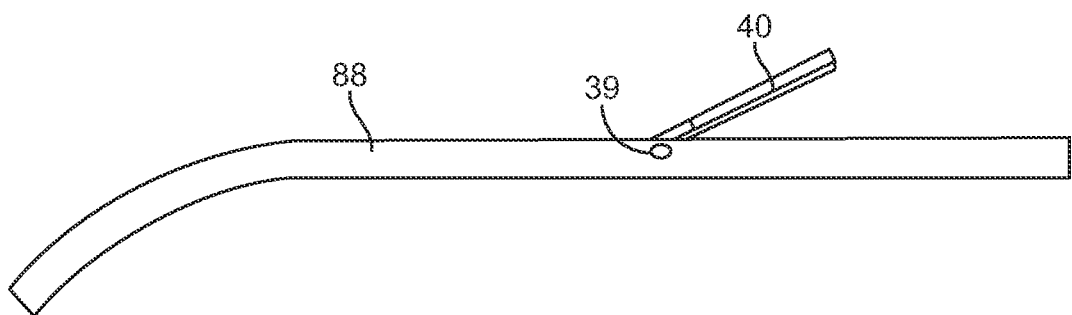
FIG. 8 shows a side view of another exemplary embodiment of an implant for long bone fixation.

FIG. 8 shows a side view of another exemplary embodiment of the implant for long bone fixation. FIG. 8 illustrates an embodiment with optional features, any of which may be optionally used or substituted with other features in other embodiments discussed herein. The implant for long bone fixation as seen in FIG. 8 comprises elongate member 88 shown in FIG. 7 and an optional locking mechanism which may be used in this embodiment or any other embodiment described herein. The locking mechanism comprises a pin 39 and an anchor 40. The elongate member 88 may comprise a plurality of locking mechanisms located on the linear portion. The locking mechanisms may be located radially around the elongate member 88. The locking mechanisms may be located axially about the elongate member 88. The locking mechanisms may be located axially and radially about the elongate member 88. The locking mechanism can expand inside the bone to provide translational and rotational stability. The anchor 40 may be a radially outward expanding arm. The anchor 40 may be tubular. The anchor 40 may have a rectangular cross-section or any other shape. The anchor 40 is preferably 5 mm to 30 mm long. More preferably, the anchor 40 is 10 mm to 20 mm long. The anchor 40 may be coupled to the elongate member 88 by a pin 39. The anchor 40 may rotate about the pin 39. The anchor 40 may be naturally in its expanded state. The anchor 40 may be naturally in its unexpanded state. The elongate member 88 may be inserted into the intramedullary canal with the anchor 40 in its unexpanded state. The anchor 40 may transition into its expanded state inside the intramedullary canal. The anchor 40 may expand so that the anchor 40 contacts the intramedullary walls. The anchor 40 may provide translational and/or rotational stability by anchoring to the bone. The anchor 40 may be self-expanding. The anchor 40 may be manually expanded. The pin 39 may be spring loaded to maintain the anchor 40 in its expanded state. The pin 39 may have any mechanism to maintain the anchor 40 in its expanded state. The anchor 40 may lay flat against the elongate member 88 in its unexpanded state. The pin 39 and anchor 40 may be located near the proximal end of the elongate member 88. The pin 39 and anchor 40 are preferably 5 mm to 100 mm from the proximal end. More preferably, the pin 39 and anchor 40 are 5 mm to 30 mm from the proximal end.

Figure 9:
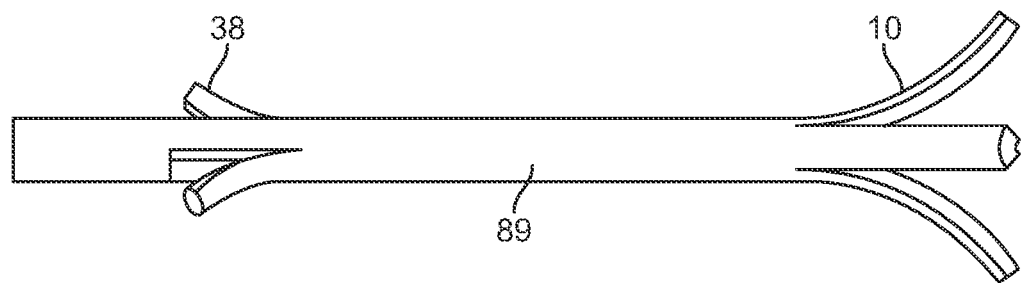
FIG. 9 shows a side view of another exemplary embodiment of an implant for long bone fixation.

FIG. 9 shows a side view of another exemplary embodiment of the implant for long bone fixation. FIG. 9 illustrates an embodiment with optional features, any of which may be optionally used or substituted with other features in other embodiments discussed herein. The implant for long bone fixation as seen in FIG. 9 comprises an elongate member 89 with one or more flared members 10, 38. The elongate member 89 may comprise a plurality of flared members 10 near the proximal end. The proximal flared members 10 are preferably 5 mm to 20 mm from the proximal end. More preferably, the flared members 10 are 5 mm to 10 mm from the proximal end. The elongate member 89 may comprise a plurality of flared members 38 near the distal end. The distal flared members 38 are preferably 5 mm to 20 mm from the distal end. More preferably, the flared members 38 are 5 mm to 10 mm from the distal end. The flared members 10, 38 may be located radially around the elongate member 89. The flared members 10, 38 may be located axially about the elongate member 89. The flared members 10, 38 may be located radially and axially about the elongate member 89. The flared members may face forward or backward. The flared members 10, 38 may have an unexpanded state wherein the flared members 10, 38 are flush with the elongate member 89 so that the overall diameter is the same throughout. The flared members 10, 38 may have an expanded state wherein the flared members 10, 38 bend radially outward. The flared members 10, 38 may expand in an arcuate shape. The flared members 10, 38 may expand in any other shape. The flared members 10, 38 may be all of the same shape and size. The flared members 10, 38 may be of various shapes and sizes. The proximal flared members 10 preferably extend outwardly 2 mm to 20 mm. More preferably, the proximal flared members 10 extend outwardly 10 mm to 15 mm. The distal flared members 38 preferably extend outwardly 2 mm to 20 mm. More preferably, the distal flared members 38 extend outwardly 5 mm to 10 mm. The flared members 10, 38 may be naturally in their expanded state. The flared members 10, 38 may be naturally in their unexpanded state. The elongate member 89 may be inserted into the intramedullary canal with the flared members 10, 38 in their unexpanded state. The flared members 10, 38 may transition into their expanded state inside the intramedullary canal. The flared members 10, 38 may expand so that the flared members 10, 38 contact the intramedullary walls. The flared members 10, 38 may provide translational and/or rotational stability by anchoring to the bone. The flared members 10, 38 may be self-expanding. The flared members 10, 38 may expand when heated to body temperature. The flared members 10, 38 may be expanded through mechanical, temperature, or other manipulation.

Figure 10:
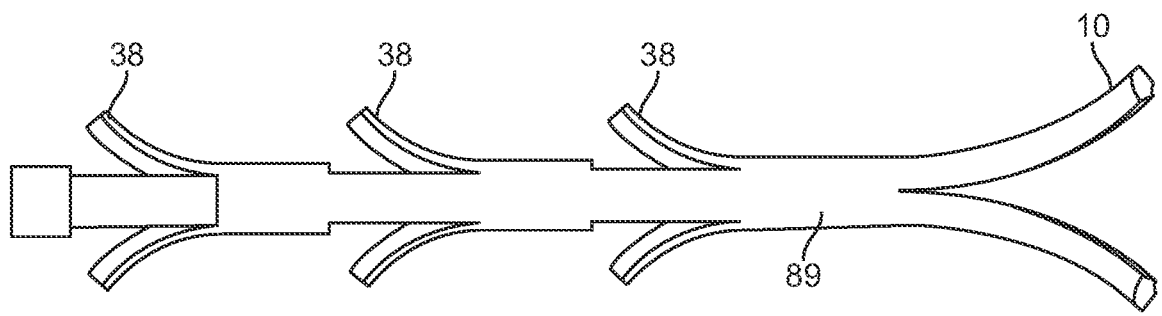
FIG. 10 shows a top view of another exemplary embodiment of an implant for long bone fixation.

FIG. 10 shows a top view of another exemplary embodiment of an implant for long bone fixation. FIG. 10 illustrates an embodiment with optional features, any of which may be optionally used or substituted with other features in other embodiments discussed herein. In particular, FIG. 10 shows an embodiment of the embodiment as described in FIG. 9, comprising the same elongate member 89 and one or more flared members 10, 38. The plurality of flared members 10, 38 may grip the bone along several locations along the medullary cavity. Said members 10, 38 may extend either forward or backward. In some cases, in this exemplary embodiment there are three axial positions and two radial positions for distal flared members 38 and one axial position and two radial positions for proximal flared members 10. FIG. 8 shows the flared members 10, 38 in their expanded state.

Figure 11:
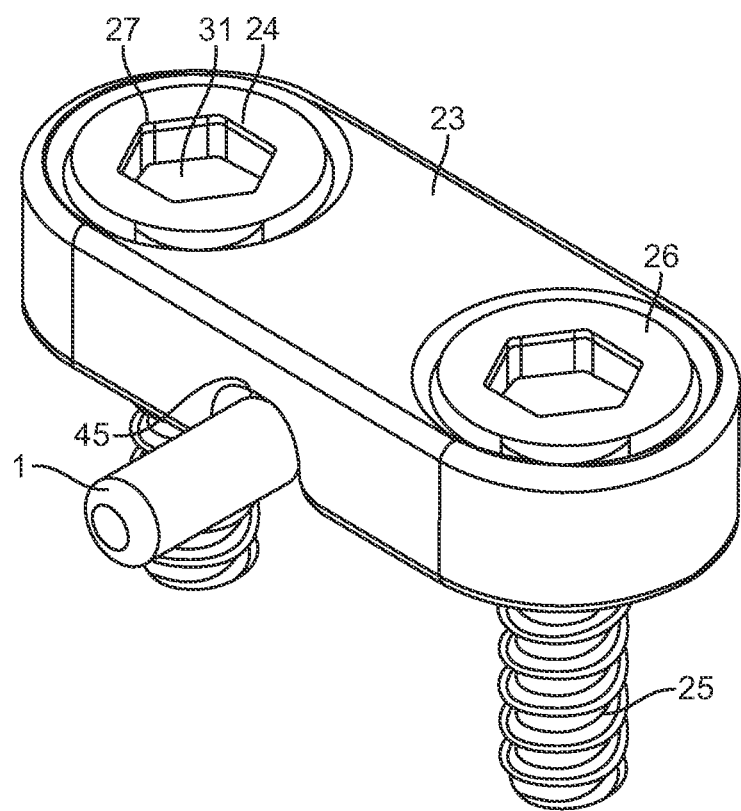
FIG. 11 shows a perspective view of an exemplary embodiment of a locking mechanism.

FIG. 11 shows a perspective view an exemplary embodiment of a locking mechanism. FIG. 11 illustrates an embodiment with optional features, any of which may be optionally used or substituted with other features in other embodiments discussed herein. The locking mechanism as shown in FIG. 11 may be used with any of the embodiments disclosed herein and comprises a plate 23 with a recess 45 and at least two through holes 31 to receive at least two screws 24. The plate 23 may have flat inferior and superior surfaces. The plate 23 may have inferior and superior surfaces to mimic bone surface. The plate 23 may have inferior and superior surfaces of any profile. The plate 23 may be pill shaped. The plate 23 may be rectangular. The plate 23 may be any other shape. The plate 23 may have a recess 45 on its inferior surface. The recess 45 may extend the length of the plate. The recess 45 may be centered on the plate 23. The recess 45 may be positioned anywhere on the plate 23 such that the two through holes 31 to receive screws 24 are outward of the recess 45. The recess 45 may be of ovular or circular shape. The recess 45 may be shaped to receive a portion of the elongate member 1. The through holes 31 may be sized to receive screws 24. The through holes 31 may be located on each end. The through holes 31 may have chamfers on the superior surface. The screws 24 may comprise a shaft with threads 25 and a head 26. The screws 24 may have external threads 25 to engage with bone. The threads 25 may span the entire length of screw 24 shaft. The threads 25 may span partially across the length of the screw 24 shaft. The threads 25 may have a pitch of 0.2 to 1 mm. More preferably, the threads 25 may have a pitch of 0.3 mm to 0.6 mm. The threads 25 may have a cancellous bone thread profile. The threads 25 may have a cortical bone thread profile. The threads 25 may have varying thread profiles along its length. The head 26 may comprise a recess 27 that allows for driving of the screw. The recess 27 may be hexagonally shaped to receive a hex head tool. The recess 27 may have any other shape. The recess 45 of the plate 23 may clamp a portion of the elongate member 1 to the bone by pinching it between the plate 23 and an outer surface of the bone.

Figure 12:
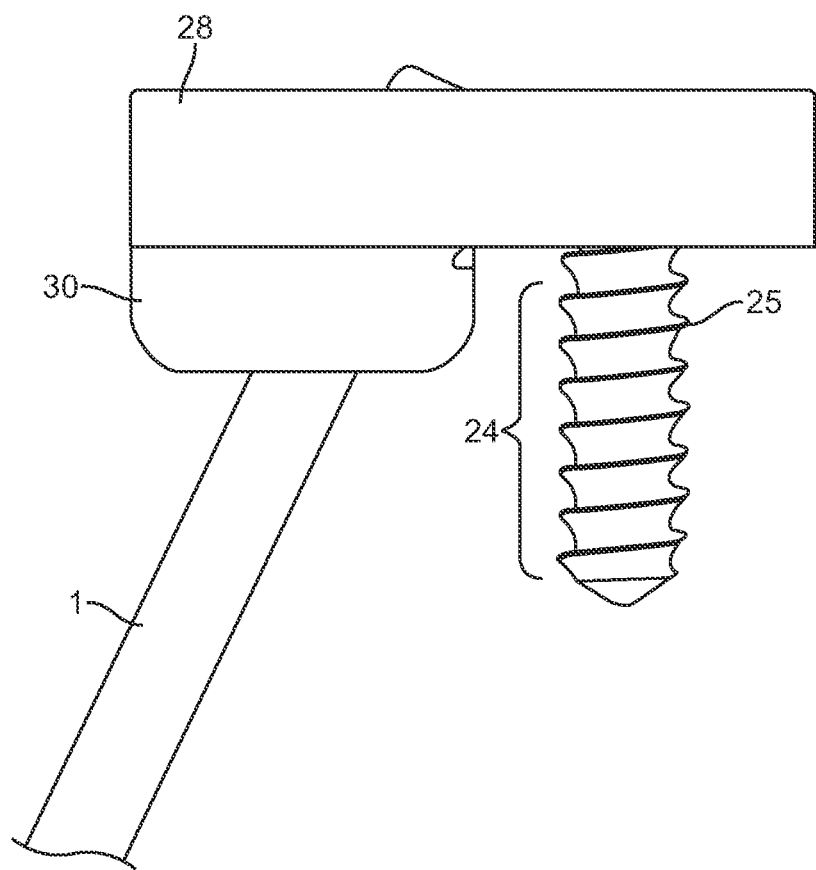
FIG. 12 shows a side view of an exemplary embodiment of a locking mechanism.
Figure 13:
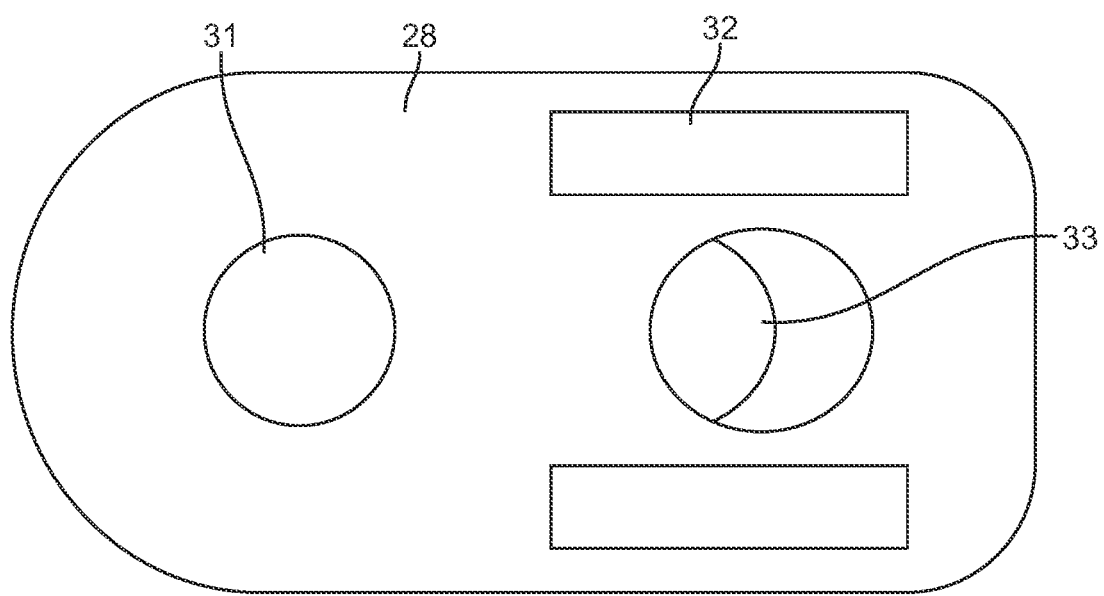
FIG. 13 shows a bottom view of an exemplary embodiment of a plate.
Figure 14:
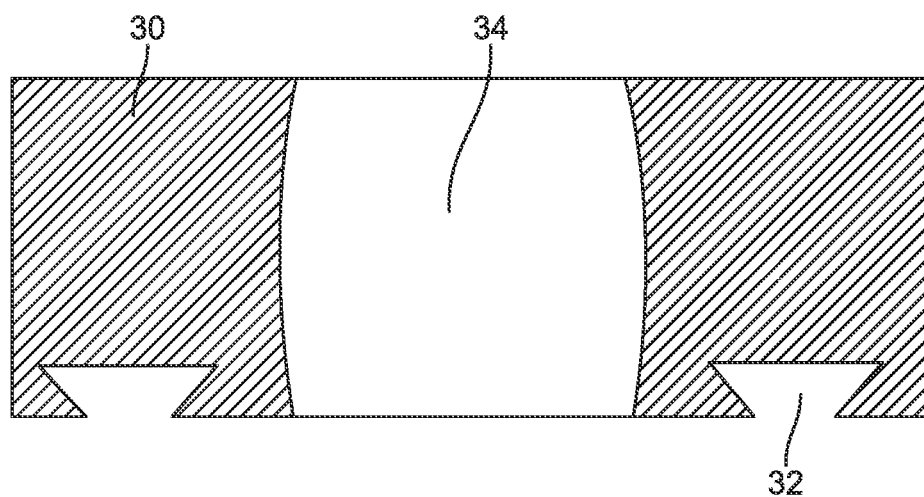
FIG. 14 shows a cross-section view of an exemplary embodiment of a shear clamp.

FIGS. 12-14 show an embodiment of a locking mechanism which may be used with any of the embodiments described herein. FIGS. 12-14 each illustrate an embodiment with optional features, any of which may be optionally used or substituted with other features in other embodiments discussed herein. FIG. 12 shows a side view of an exemplary embodiment of a locking mechanism. FIG. 13 shows a bottom view of an exemplary embodiment of a plate. FIG. 14 shows a cross-section view of an exemplary embodiment of a shear clamp.

FIGS. 12-14 comprise a screw 24, a plate 28 and a shear clamp 30. The plate 23 may have flat inferior and superior surfaces. The plate 28 may have inferior and superior surfaces to mimic bone surface. The plate 28 may have inferior and superior surfaces of any profile. The plate 28 may be pill shaped. The plate 28 may be rectangular. The plate 28 may be any other shape. The shear clamp 30 may have a corresponding shape to that of the plate 28. The shear clamp 30 may be shaped to fit into an awled out portion of bone so as to sit flush. As shown in FIG. 12, the shear clamp 30 and plate 28 may attach with one or more rails 32. The plate 28 may sit on top of the shear clamp 30. The rails 23 may span from the distal end toward the proximal end. The rails 23 may span a portion of the length of the plate 28. The rails 23 may span the entire length of the shear clamp 30. The shear clamp 30 may have a female rail and the plate 28 may have a male rail. Alternatively, the shear clamp 30 may have a male rail and the plate 28 may have a female rail. The rails 32 may be mating shapes. As shown in FIG. 14, the rails 32 may be dove-tail in shape. The rails 32 may also be any other mating shape. The rails 32 allow the shear clamp to slide along the length of the plate 28. The plate 28 may have a diagonally oriented round hole 33. The hole 33 is preferably offset at an angle of 30 degrees to 60 degrees. More preferably, the hole 33 is offset at an angle of 40 degrees to 50 degrees. The hole 33 may be sized to have a sliding fit with the elongate member 1. The shear clamp 30 may have a diagonally oriented hole 34. The hole 34 may have the same size and angle-orientation as the plate 28 hole 33. The holes 33, 34 may be positioned on the plate 28 and shear clamp 30 such that the holes are aligned as the shear clamp 30 is in a starting position on the plate 28 rail 23. The holes 33, 34 may be positioned on the plate 28 and shear clamp 30 such that the holes 33, 34 are offset as the shear clamp 30 reaches the end position of the plate 28 rail 23, as shown in FIG. 12. When the holes 33, 34 are aligned, the elongate member 1 may pass through freely. When the holes 33, 34 are offset, the elongate member 1 may be pinched by a shear force. The shear force to the elongate member 1 may prevent rotational and translational motion. The plate 28 and shear clamp 30 may be able to be locked in place together with a locking feature described in FIGS. 15 and 16. The plate 28 may have a round though hole 31 placed near the proximal end. The through hole 31 is preferably orthogonal to the plate. The through hole 31 may be sized to receive a screw 24. The through hole 31 may be chamfered on the superior surface. The screw 24 may comprise a shaft with threads 25 and a head (not pictured). The screw 24 may have external threads 25 to engage with bone. The threads 25 may span the entire length of screw 24 shaft. The threads 25 may span partially across the length of the screw 24 shaft. The threads 25 may have a pitch of 0.2 to 1 mm. More preferably, the threads 25 may have a pitch of 0.3 mm to 0.6 mm. The threads 25 may have a cancellous bone thread profile. The threads 25 may have a cortical bone thread profile. The threads 25 may have varying thread profiles along its length. The head may comprise a recess (not pictured) that allows for driving of the screw. The recess may be hexagonally shaped to receive a hex head tool. The recess may have any other shape. The screw 24 may secure the locking mechanism to an outward surface of the bone.

Figure 15:
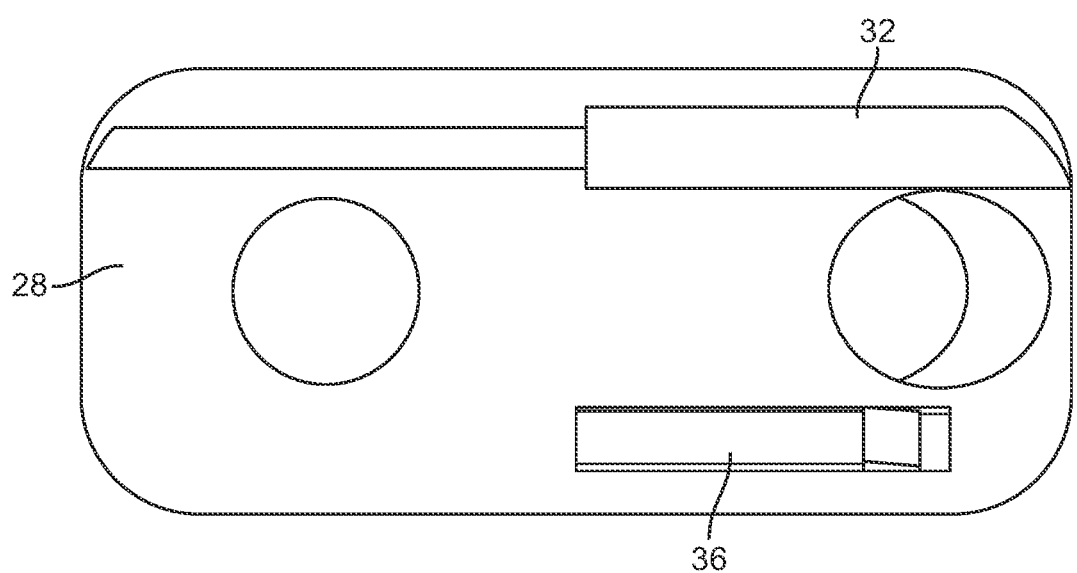
FIG. 15 shows a bottom view of another exemplary embodiment of a plate.
Figure 16:
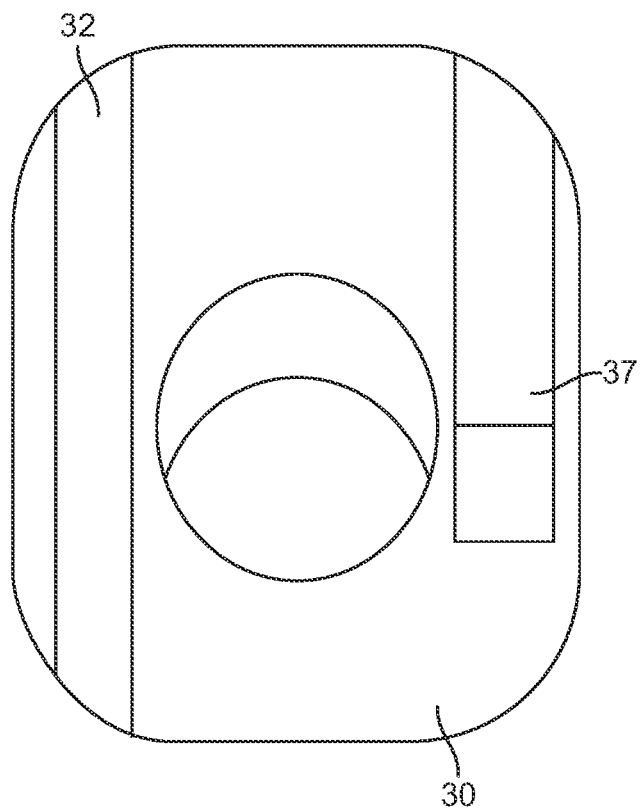
FIG. 16 shows a top view of another exemplary embodiment of a shear clamp.

FIGS. 15 and 16 show an embodiment as described in FIGS. 12-14 when they are coupled together, which may be used with any embodiment described herein. FIGS. 15 and 16 each illustrate an embodiment with optional features, any of which may be optionally used or substituted with other features in other embodiments discussed herein. FIG. 15 shows a bottom view of another exemplary embodiment of a plate. FIG. 16 shows a top view of another exemplary embodiment of a shear clamp.

As one embodiment, in this embodiment the rail 32 on the plate 28 comprises a latch 36 (as shown in FIG. 15) and the rail 32 on the shear clamp 30 comprises a concave cutout 37 (as shown in FIG. 16) for receiving said latch 36. The latch 36 may be a lip with an angled edge. The latch 36 may be flexible to spring out and back. The concave cutout 37 may be of a shape corresponding to the latch 36 such that the angled edge mates with the concave cutout 37. When the latch 36 engages with the concave cutout 37, the linear motion of the shear clamp 30 with respect to the plate 28 may be constrained.

Figure 17:
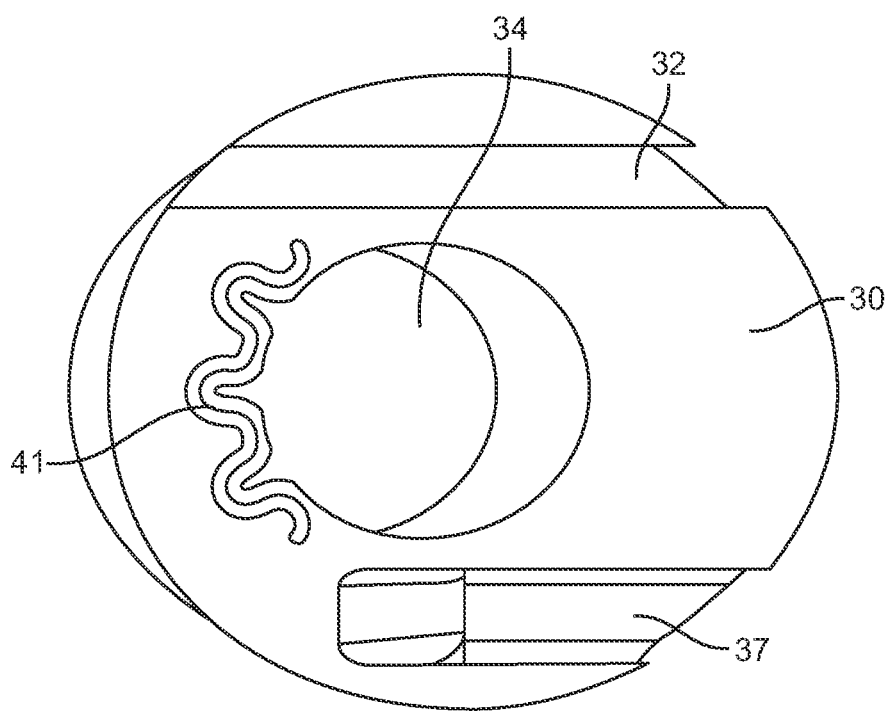
FIG. 17 shows a top view of another exemplary embodiment of a shear clamp.

FIG. 17 shows a top view of another exemplary embodiment of a shear clamp. FIG. 17 illustrates an embodiment with optional features, any of which may be optionally used or substituted with other features in other embodiments discussed herein. In particular, FIG. 17 shows an embodiment of the shear clamp 30 with rails 32, a concave cutout 37, and a hole 34, as described in FIG. 16. In this embodiment, the shear clamp 30 may be ovular. In this embodiment, the embodiment may comprise a dampening slot 41. The dampening slot 41 may be distal to the hole 34. The dampening slot 41 may offset the hole 34 in a c-shape. The dampening slot 41 may offset the hole 34 with a snaking pattern. The dampening slot 41 may be any shape. The dampening slot 41 preferably offsets the hole 34 by 1 mm to 10 mm. More preferably, the dampening slot 41 offsets the hole 34 by 1 mm to 3 mm. The dampening slot 41 may allow for deflection of the shear clamp 30 during locking of the latch on the plate (not pictured) to the concave cutout 37 on the shear clamp 30.

Figure 18:
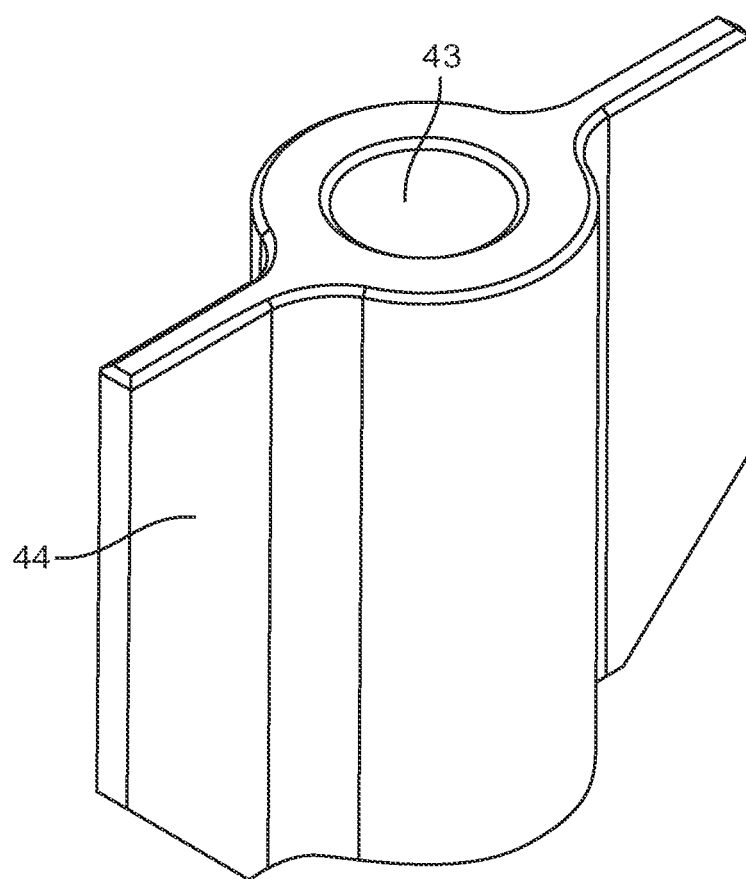
FIG. 18 shows a perspective view of another exemplary embodiment of a locking mechanism.

FIG. 18 shows a perspective view of another exemplary embodiment of a locking mechanism. FIG. 18 illustrates an embodiment with optional features, any of which may be optionally used or substituted with other features in other embodiments discussed herein. In particular, FIG. 18 shows another embodiment of a locking mechanism which may be used with any embodiment described herein. The locking mechanism may have a cylindrical body. The locking mechanism may be any shape. The locking mechanism may comprise a round hole 43 spanning the length of the cylindrical body. The hole 43 may be sized to slidably receive any of the elongate members described herein (not pictured). The tight fit between the hole 43 and elongate member may provide translational and rotational stability. This embodiment may comprise a plurality of wings 44. The wings 44 may be flat planar elements. The wings 44 may extend radially outward from the cylindrically shaped body. There are preferably two wings, spaced 180 degrees apart but may have more or less wings 44. The wings 44 may provide rotational stability when inserted into bone.

Figure 19:
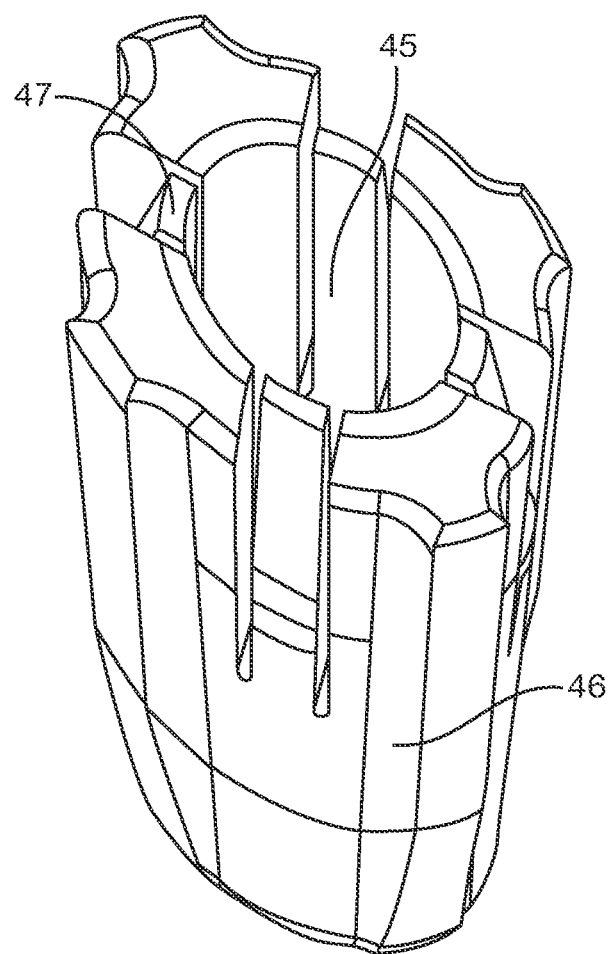
FIG. 19 shows a perspective view of another exemplary embodiment of a locking mechanism.

FIG. 19 shows a perspective view of another exemplary embodiment of a locking mechanism. FIG. 19 illustrates an embodiment with optional features, any of which may be optionally used or substituted with other features in other embodiments discussed herein. In particular, FIG. 19 shows another embodiment of a locking mechanism which may be used with any embodiment described herein. The locking mechanism may have a cylindrical body. The locking mechanism may be any shape. This embodiment may comprise a round hole 45. The hole 45 may extend the length of the locking mechanism. The hole 45 may be sized to receive any of the elongate members described herein (not pictured). This embodiment may comprise one or more of crimp tabs 47. The crimp tabs 47 may be formed due to slots on either side of the tabs 45. The crimp tabs 47 may be flexible to bend inwardly. The crimp tabs 47 may have an angled outside surface such that the thickness increases proximally to distally. The crimp tabs 47 may span from the proximal end, partially across the length of the locking mechanism. The crimp tabs 47 may be located radially around the locking mechanism. There are preferably three to six crimp tabs 47. More preferably, there are three to five crimp tabs 47 evenly spaced around the circumference of the locking mechanism. The crimp tabs 47 may be pushed inwardly to grasp the elongate member passing through the hole 45. The crimp tabs 47 may prevent translational or rotational motion of the elongate member relative to the locking mechanism. The locking mechanism may comprise one or more anti-rotation tabs 46. The anti-rotation tabs 46 may have a thickness greater than the crimp tabs 47. The anti-rotation tabs 46 may have a triangular cross-sectional shape. The anti-rotation tabs 46 may have any cross-sectional shape. The anti-rotation tabs 46 may be tapered. The anti-rotation tabs 46 may span across the length of the locking mechanism. The anti-rotation tabs 46 may span partially across the length of the locking mechanism. The anti-rotation tabs 46 may be positioned in between the crimp tabs 47. The anti-rotation tabs 46 may be located radially around the locking mechanism. There are preferably three to six anti-rotation tabs 46. More preferably, there are three to five anti-rotation tabs 46 evenly spaced around the circumference of the locking mechanism. The anti-rotation tabs 46 may be rigid. The anti-rotation tabs 46 may engage with the bone to prevent rotational motion of the locking mechanism relative to the bone.

Figure 20A:
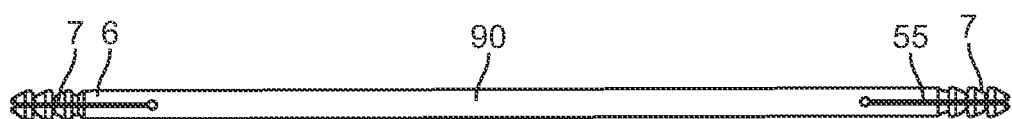
FIG. 20A shows a side view of another exemplary embodiment of an implant before expansion.
Figure 20B:
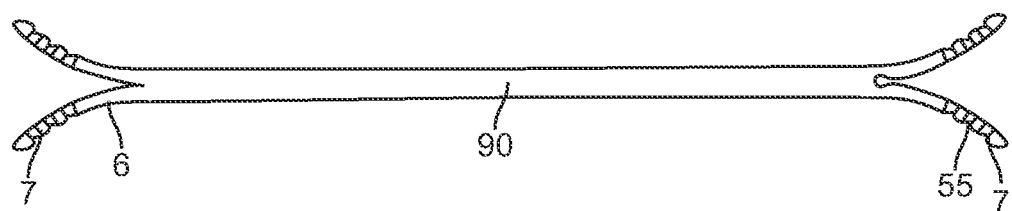
FIG. 20B shows a side view of another exemplary embodiment of an implant after expansion.

FIGS. 20A-20B show another embodiment of an implant for treating fractured bones. FIGS. 20A and 20B each illustrate an embodiment with optional features, any of which may be optionally used or substituted with other features in other embodiments discussed herein. FIG. 20A shows a side view of another exemplary embodiment of an implant before expansion. FIG. 20B shows a side view of another exemplary embodiment of an implant after expansion.

The implant may comprise an elongate member 90 with distal end 6 and proximal end 55. The elongate member 90 is preferably circular. The elongate member 90 may also be of ovular cross-section, square cross-section or any other shape. The elongate member 90 is preferably a solid member but may also be hollow. The elongate member 90 may be available in various lengths to provide for different long bone uses and varying patient anatomy. In some cases, the elongate member 90 may have a length of 100 mm to 150 mm for use in a clavicle. In some cases, the elongate member 90 may have a length of 320 to 370 mm for use in a fibula. The elongate member 90 may be cut to length during implantation. The elongate member 90 may have various diameters to account for different long bone uses and varying patient anatomy. The elongate member 90 preferably has a diameter of 1 mm to 5 mm. More preferably, the elongate member 90 may have a diameter of 1.5 mm to 3.5 mm. The elongate member 90 is preferably rigid across its entire length. The elongate member 90 may be flexible along a portion or all of its length. The elongate member 90 may be nitinol. The elongate member 90 may be nickel titanium or any metal. The distal end 6 may be tapered at the tip. The proximal end 55 may be tapered at the tip. The distal end 6 and proximal end 55 may have features for expansion and bone contact described herein. The distal end 6 and proximal end 55 may have identical features. The distal end 6 and proximal end 55 may have features of varying shape and/or size. The ends 6, 55 may be sectioned into two or more pieces with a slit extending longitudinally toward the opposite end. The ends 6, 55 sectioned pieces may be abutting each other such that there is no slit. The ends 6, 55 slits preferably extend 5 mm to 30 mm along its length. More preferably, the ends 6, 55 slits extend 5 mm to 15 mm. The ends 6, 55 may be sectioned by cutting, wire EDM, or any other method of separation. The ends 6, 55 of the elongate member 90 may have an expanded state and an unexpanded state such that the ends 6, 55 may expand inside the cancellous bone at the end of the long bone (not pictured) when implanted. The ends 6, 55 may be naturally in the expanded state. The ends 6, 55 may be naturally in the unexpanded state. The ends 6, 55 may be self-expanding.

The ends 6, 55 may be expanded through mechanical, temperature, or other manipulation. FIG. 20A shows the elongate member 90 in its unexpanded state. The elongate member 90 in its unexpanded state may have a constant across the length the elongate member 90. The ends 6, 55 of the elongate member 90 may have one or more grooves 7 to aid in gripping cancellous bone. The grooves 7 may be circumferential rings. The grooves 7 may be sharp barbs. The grooves 7 may be cutouts of any shape. The grooves 7 may be disposed axially along the distal portion. FIG. 20B shows the elongate member 90 in its expanded state. The end 6, 55 tips may flare radially outward away from one another in its expanded state. The end 6, 55 tips may have an arcuate shape. The ends 6, 55 may have any other shape. The distance between the end 6, 55 tips in its expanded state is preferably 5 mm to 30 mm. More preferably, the distance between the ends 6, 55 may be 5 mm to 15 mm.

Figure 21A:
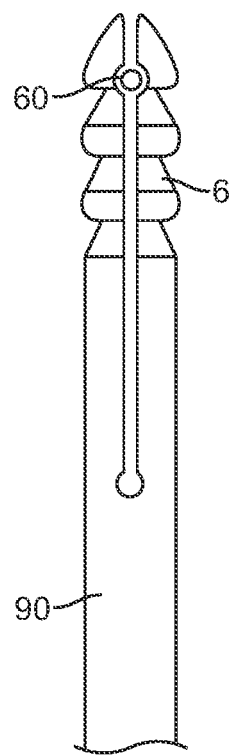
FIG. 21A shows a side view of a distal end of another exemplary embodiment of an implant before expansion.
Figure 21B:
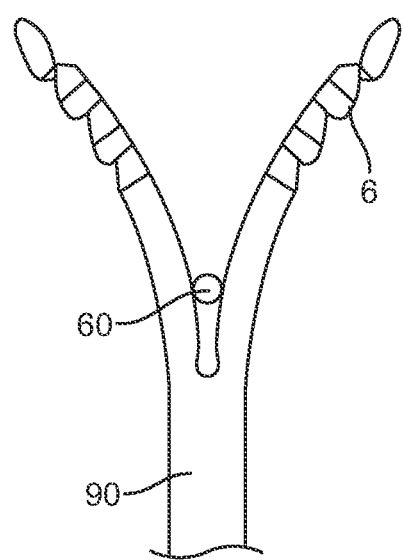
FIG. 21B shows a side view of a distal end of another exemplary embodiment of an implant after expansion.

FIGS. 21A-21B show the distal end of the embodiment described in FIGS. 20A-20B, which may be used with any of the elongate members disclosed herein. FIGS. 21A and 21B each illustrate an embodiment with optional features, any of which may be optionally used or substituted with other features in other embodiments discussed herein. FIG. 21A shows a side view of a distal end of another exemplary embodiment of an implant before expansion. FIG. 21B shows a side view of a distal end of another exemplary embodiment of an implant after expansion. FIGS. 21A-21B show an embodiment of a method for expanding the elongate member 90 ends. The elongate member 90 may comprise a distal tip 6 which may be expanded manually by a surgeon using a pin 60. The pin 60 may be inserted between the distal end 6 arms. The pin 60 may be pre-assembled, disposed between the arms. The pin 60 may be moved toward the proximal end to push the arms radially outward into their expanded state. The distal end 6 may deform plastically to maintain its expanded state. After expansion, the pin 60 may be removed. FIG. 21A shows the distal end 6 in its unexpanded state and FIG. 21B shows the distal end 6 in its expanded state. The distal end 6 of the elongate member 90 may have an expanded state and an unexpanded state such that the end 6 may expand inside the cancellous bone at the end of the long bone (not pictured) when implanted.

Figure 22A:
FIG. 22A shows a side view of another exemplary embodiment of an implant before expansion.
Figure 22B:
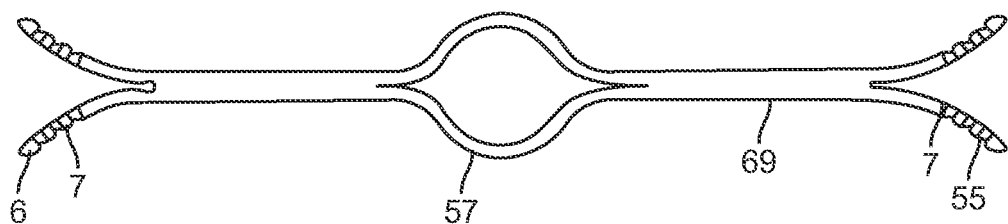
FIG. 22B shows a side view of another exemplary embodiment of an implant after expansion.

FIGS. 22A-22B show another embodiment of an implant for treating fractured bones. FIGS. 22A and 22B each illustrate an embodiment with optional features, any of which may be optionally used or substituted with other features in other embodiments discussed herein. FIG. 22A shows a side view of another exemplary embodiment of an implant before expansion. FIG. 22B shows a side view of another exemplary embodiment of an implant after expansion.

The implant may comprise an elongate member 69 with a distal end 6, proximal end 55, and expanding center 57. The elongate member 69 is preferably circular. The elongate member 69 may also be of ovular cross-section, square cross-section or any other shape. The elongate member 69 is preferably a solid member but may also be hollow. The elongate member 69 may be available in various lengths to provide for different long bone uses and varying patient anatomy. In some cases, the elongate member 69 may have a length of 100 mm to 150 mm for use in a clavicle. In some cases, the elongate member 69 may have a length of 320 to 370 mm for use in a fibula. The elongate member 69 may be cut to length during implantation. The elongate member 69 may have various diameters to account for different long bone uses and varying patient anatomy. The elongate member 69 preferably has a diameter of 1 mm to 5 mm. More preferably, the elongate member 69 may have a diameter of 1.5 mm to 3.5 mm. The elongate member 69 is preferably rigid across its entire length. The elongate member 69 may be flexible along a portion or all of its length. The elongate member 69 may be nickel titanium or any metal. The distal end 6 may be tapered at the tip. The proximal end 55 may be tapered at the tip. The distal end 6 and proximal end 55 may have features for expansion and bone contact described herein. The distal end 6 and proximal end 55 may have identical features. The distal end 6 and proximal end 55 may have features of varying shape and/or size. The ends 6, 55 may be sectioned into two or more pieces with a slit extending longitudinally toward the opposite end. The ends 6, 55 sectioned pieces may be abutting each other such that there is no slit. The ends 6, 55 slits preferably extend 5 mm to 30 mm along its length. More preferably, the ends 6, 55 slits extend 5 mm to 15 mm. The ends 6, 55 may be sectioned by cutting, wire EDM, or any other method of separation. The ends 6, 55 of the elongate member 90 may have one or more grooves 7 to aid in gripping cancellous bone. The grooves 7 may be circumferential rings. The grooves 7 may be sharp barbs. The grooves 7 may be cutouts of any shape. The grooves 7 may be disposed axially along the distal portion. The expanding center 57 may be positioned half way from the proximal end to the distal end. The expanding center 57 may be positioned at any point along the length of the elongate member 69. The expanding center 57 may be sectioned into two or more pieces with a slit extending longitudinally toward the opposite end. The expanding center 57 sectioned pieces may be abutting each other such that there is no slit. The expanding center 57 slits preferably extend 5 mm to 30 mm. More preferably, the expanding center 57 slits extend 5 mm to 15 mm. The expanding center 57 may be sectioned by cutting, wire EDM, or any other method of separation. The ends 6, 55 and expanding center 57 of the elongate member 69 may have an expanded state and an unexpanded state such that the ends 6, 55 and center 57 may expand inside the cancellous bone at the end of the long bone (not pictured) when implanted. The ends 6, 55 and center 57 may be naturally in the expanded state. The ends 6, 55 and center 57 may be naturally in the unexpanded state. The ends 6, 55 and center 57 may be self-expanding. The ends 6, 55 and center 57 may be expanded through mechanical, temperature, or other manipulation. FIG. 22A shows the elongate member 69 in its unexpanded state. The elongate member 69 in its unexpanded state may have a constant diameter along the length of the elongate member 69. FIG. 22B shows the elongate member 69 in its expanded state. The elongate member 69 may be expanded after implantation. The end 6, 55 tips may flare radially outward away from one another in its expanded state. The end 6, 55 tips may contact the intramedullary canal surface of the bone. The end 6, 55 tips may have an arcuate shape. The ends 6, 55 may have any other shape. The distance between the end 6, 55 tips in its expanded state is preferably 5 mm to 30 mm. More preferably, the distance between the ends 6, 55 may be 5 mm to 15 mm. The expanding center 57 may flare radially outward into a bifurcated center section in its expanded state. The center 57 may have an ovular shape. The center 57 may take any other shape with a convex outer surface and a concave inner surface. The center 57 expansion distance is preferably 5 mm to 30 mm. More preferably, the expansion distance may be 5 mm to 15 mm. The expanded center 57 may aid in compressing two bone fragments together. The expanding center 57 may be expanded at the same time as the distal 6 and proximal ends 55. The expanding center 57 may be expanded after the distal 6 and proximal ends 55. The center 57 expansion may cause the distal 6 and proximal ends 55 to be drawn inward towards each other, further reducing the fracture.

Figure 23A:
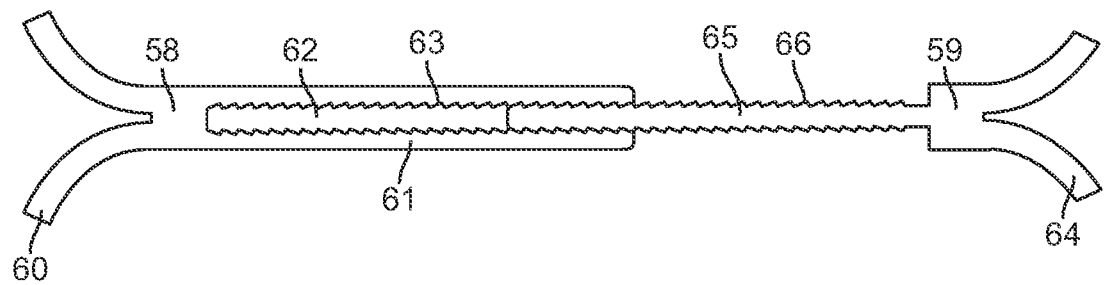
FIG. 23A shows a side view of another exemplary embodiment of an implant before expansion.
Figure 23B:
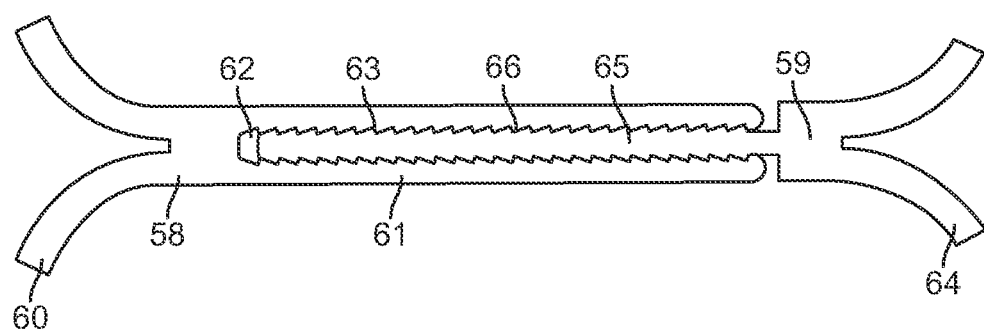
FIG. 23B shows a side view of another exemplary embodiment of an implant after expansion.

FIGS. 23A-23B show another embodiment of an implant for treating fractured bones. FIGS. 23A and 23B each illustrate an embodiment with optional features, any of which may be optionally used or substituted with other features in other embodiments discussed herein. FIG. 23A shows a side view of another exemplary embodiment of an implant before expansion. FIG. 23B shows a side view of another exemplary embodiment of an implant after expansion.

The implant may comprise an elongate member 61 with a distal component 58 and a proximal component 59. The distal component 58 may have an internal channel 62 with internal teeth 63 that extend radially inward. The internal channel 21 may partially span the length of the distal component 58. The proximal component 59 may have a shaft 65 which may contain external teeth 66 that extend radially outward. The external teeth 66 may be sized and positioned to engage with the internal teeth 63. The teeth 63, 66 may allow the shaft 65 to be telescopically inserted into the channel 62 of the distal component 58. The shaft 65 may insert into channel 62 such that external teeth 66 and internal teeth 63 engage one another and lock together to prevent the proximal end 59 from retreating out of the channel 62. The elongate member 61 is preferably circular. The elongate member 61 may also be of ovular cross-section, square cross-section or any other shape. The elongate member 61 may be available in various lengths to provide for different long bone uses and varying patient anatomy. In some cases, the elongate member 61 may have a length of 100 mm to 150 mm for use in a clavicle. In some cases, the elongate member 61 may have a length of 320 to 370 mm for use in a fibula. The elongate member 61 may be cut to length during implantation. The elongate member 61 may have various diameters to account for different long bone uses and varying patient anatomy. The elongate member 61 preferably has a diameter of 1 mm to 5 mm. More preferably, the elongate member 61 may have a diameter of 1.5 mm to 3.5 mm. The elongate member 61 is preferably rigid across its entire length. The elongate member 61 may be flexible along a portion or all of its length. The elongate member 61 may be nickel titanium or any metal. The distal component 58 may comprise an expanding distal end 60. The proximal component 59 may comprise an expanding proximal end 64. The distal end 60 and proximal end 64 may have features for expansion and bone contact described herein. The distal end 60 and proximal end 64 may have identical features. The distal end 60 and proximal end 64 may have features of varying shape and/or size. The ends 60, 64 may be sectioned into two or more pieces with a slit extending longitudinally toward the opposite end. The ends 60, 64 sectioned pieces may be abutting each other such that there is no slit. The ends 60, 64 slits preferably extend 5 mm to 30 mm along its length. More preferably, the ends 60, 64 slits extend 5 mm to 15 mm. The ends 60, 64 may be sectioned by cutting, wire EDM, or any other method of separation. The ends 60, 64 of the elongate member 61 may have an expanded state and an unexpanded state such that the ends 60, 64 may expand inside the cancellous bone at the end of the long bone (not pictured, as described in FIG. 1) when implanted. The ends 60, 64 may be naturally in the expanded state. The ends 60, 64 may be naturally in the unexpanded state. The ends 60, 64 may be self-expanding. The ends 60, 64 may be expanded through mechanical, temperature, or other manipulation. The elongate member 61 in its unexpanded state may have a diameter similar to that of the shaft of the elongate member 61. The end 60, 64 tips may flare radially outward away from one another in its expanded state. The end 60, 64 tips may have an arcuate shape. The ends 60, 64 may have any other shape. The distance between the end 60, 64 tips in its expanded state is preferably 5 mm to 30 mm. More preferably, the distance between the ends 60, 64 may be 5 mm to 15 mm. After ends 60, 64 expand and are anchored to bone, the shaft 65 may be inserted further into channel 62 to compress the two bone fragments. FIG. 23A shows the implant before the proximal component 59 has been advanced into the distal component 58 and FIG. 23B shows the implant after the proximal component 59 has been advanced into the distal component 58 thereby reducing the overall length of the device and allowing a compressive force to be applied to the fractured bone thereby compressing the bone fragments together.

Figure 24:
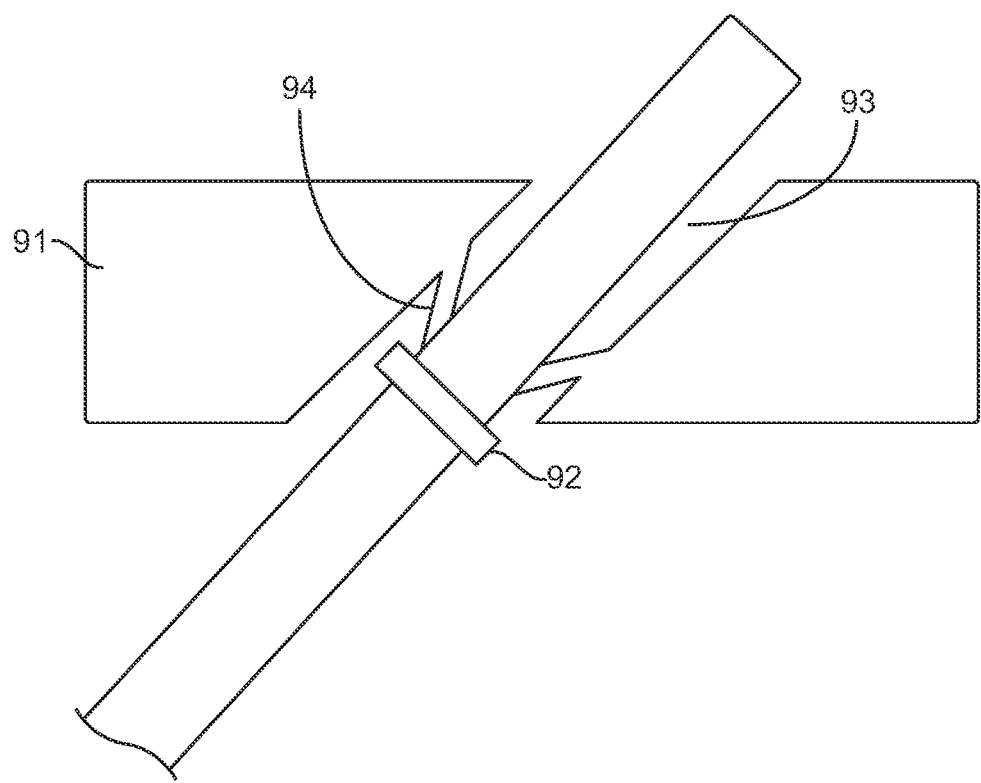
FIG. 24 shows a side view of another exemplary embodiment of a locking mechanism.

FIG. 24 shows a side view of another exemplary embodiment of a locking mechanism. FIG. 24 illustrates an embodiment with optional features, any of which may be optionally used or substituted with other features in other embodiments discussed herein. In particular, FIG. 24 shows another embodiment of a locking mechanism which may be used with any of the embodiments described herein. The locking mechanism may comprise a plate 91, an annular flange 92, a hole 93, and a tang 94. The plate 91 may have flat inferior and superior surfaces. The plate 91 may have inferior and superior surfaces to mimic bone surface. The plate 91 may have inferior and superior surfaces of any profile. The plate 91 may be pill shaped. The plate 91 may be rectangular. The plate 91 may be any other shape. The plate 91 may have a diagonally oriented round hole 93 extending all the way through the plate 91. The hole 93 is preferably offset at an angle of 30 degrees to 60 degrees. More preferably, the hole 93 is offset at an angle of 40 degrees to 50 degrees. The hole 93 may have a tang 94 located at any point in the hole. The tang 94 may be a plurality of tabs located circumferentially around the hole 91, extending inwardly perpendicular from the hole 93 wall. The tang 94 may be a plurality of tabs located circumferentially around the hole 91, extending inwardly at an angle from the hole 93 wall. The tang 94 may be a flange disposed circumferentially around the hole 93 wall, extending inwardly perpendicular to the hole 93 wall. The tang 94 may be a flange disposed circumferentially around the hole 93 wall, extending inwardly at an angle to the hole 93 wall. The tang 94 may be flexible to deflect. An annular flange 92 may attach to any of the embodiments of the elongate member disclosed herein. The annular flange 92 may attach near the proximal end. The annular flange 92 may be attached by welding, bonding, press fit, or any other bonding method. The tang 94 may deflect as the elongate member inserts through hole 93 and into the intramedullary canal but then springs back to an unbiased position and prevents the annular flange 92 from exiting the hole. The tang 94 may also prevent the retreat of the elongate member out of the hole 93 and bone.

Figure 25A:
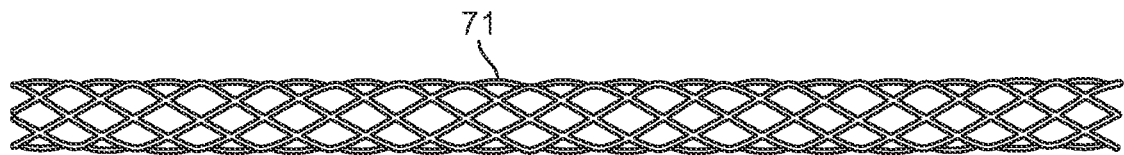
FIG. 25A shows a side view of another exemplary embodiment of an implant before expansion.
Figure 25B:
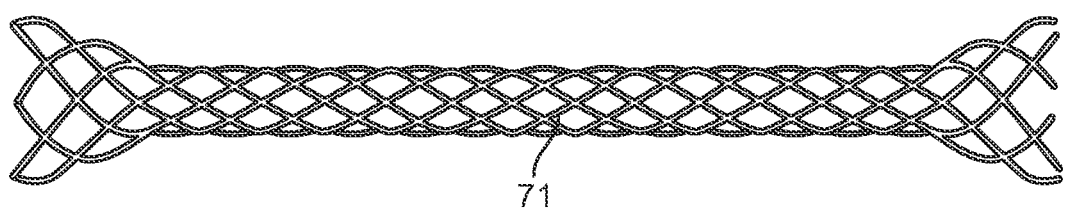
FIG. 25B shows a side view of another exemplary embodiment of an implant after expansion.

FIGS. 25A-25B show another embodiment of an implant for treating fractured bones. FIGS. 25A and 25B each illustrate an embodiment with optional features, any of which may be optionally used or substituted with other features in other embodiments discussed herein. FIG. 25A shows a side view of another exemplary embodiment of an implant before expansion. FIG. 25B shows a side view of another exemplary embodiment of an implant after expansion.

The implant may comprise a mesh tube 71 which can expand upon insertion into the medullary cavity. The mesh may be woven in a braid pattern. The mesh may be made of expanding shape memory material. The mesh may be made of other compressed mesh comprised of titanium, biocompatible plastic, or other biocompatible material. The tube 71 may self-expand. The tube 71 may naturally be in its expanded state. During insertion, a constraint may hold the mesh in the collapsed configuration and when the constraint such as an outer sheath is removed, the mesh self-expands. The tube may expand into the medullary cavity and into engagement with ends of the bone. FIG. 25A shows the implant in its unexpanded state and FIG. 25B shows the implant in its expanded state. In the expanded state, the tube may conform to the inner surface of the medullary canal of the bone to help hold the bone fragments together.

Figure 26A:
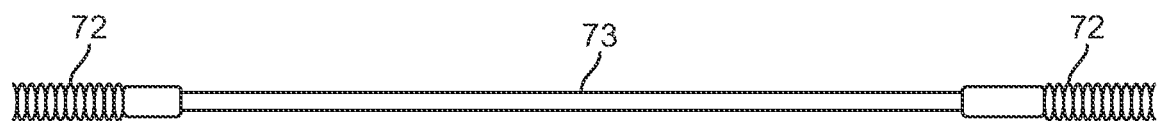
FIG. 26A shows a side view of another exemplary embodiment of an implant before expansion.
Figure 26B:
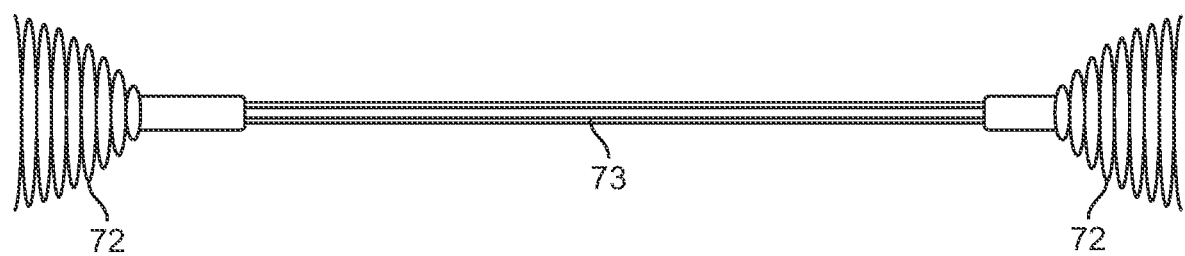
FIG. 26B shows a side view of another exemplary embodiment of an implant after expansion.

FIGS. 26A-26B show another embodiment of an implant. FIGS. 26A and 26B each illustrate an embodiment with optional features, any of which may be optionally used or substituted with other features in other embodiments discussed herein. FIG. 26A shows a side view of another exemplary embodiment of an implant before expansion. FIG. 26B shows a side view of another exemplary embodiment of an implant after expansion.

The implant comprises an elongate member 73 with an expandable coil 72 on the distal and/or proximal ends. The elongate member 73 is preferably circular with a proximal end and distal end. The elongate member 73 may also be of ovular cross-section, square cross-section or any other shape. The elongate member 73 is preferably a solid member but may also be hollow. The elongate member 73 may be available in various lengths to provide for different long bone uses and varying patient anatomy. In some cases, the elongate member 73 may have a length of 100 mm to 150 mm for use in a clavicle. In some cases, the elongate member 73 may have a length of 320 to 370 mm for use in a fibula. The elongate member 73 may have various diameters to account for different long bone uses and varying patient anatomy. The elongate member 73 preferably has a diameter of 1 mm to 5 mm. More preferably, the elongate member 73 may have a diameter of 1.5 mm to 3.5 mm. The elongate member 73 is preferably rigid across its entire length. The elongate member 73 may be flexible along a portion or all of its length. The elongate member 73 may be nickel titanium or any metal. The expandable coil 72 may be a single wire coiled with an increasing radial pattern. The expandable coil 72 may be multiple wires coiled with an increasing radial pattern. The expandable coil 72 is preferably made of solid wire of diameter 0.2 mm to 3 mm. More preferably, the expandable coil 72 is made of solid wire of diameter 0.2 mm to 0.5 mm. The coil 72 may be made of tubular structures. The expandable coil 72 may be multiple wires woven in a helical pattern. The coils 72 may be attached to the proximal and distal ends of the elongate member 73 by welding, mechanical mechanisms, or other bonding methods. The coil 72 may have an expanded state and an unexpanded state such that the distal and proximal ends may expand inside the cancellous bone at the end of the long bone (not pictured) when implanted. The coil 72 may be naturally in the expanded state. The coil 72 may be naturally in the unexpanded state. The coil 72 may be self-expanding. The coil 72 may be expanded through mechanical, temperature, or other manipulation. The coil 72 in its unexpanded state may have a diameter similar to that of the shaft of the elongate member 73. The coil 72 in its expanded state preferably has a maximum diameter of 5 mm to 30 mm. More preferably, the coil 72 has a maximum diameter of 5 mm to 15 mm. The expandable coil 72 may increase in diameter upon expansion and may expand into the cancellous bone and the walls of the medullary cavity at the end of the bone in order to grip and stabilize the bone. The distal and proximal coils 72 may expand simultaneously. The distal coil 72 may expand first, followed by the proximal. The proximal coil 72 may expand first, followed by the distal. FIG. 26A shows the implant in its unexpanded state and FIG. 26B shows the implant in its expanded state.

Figure 27A:
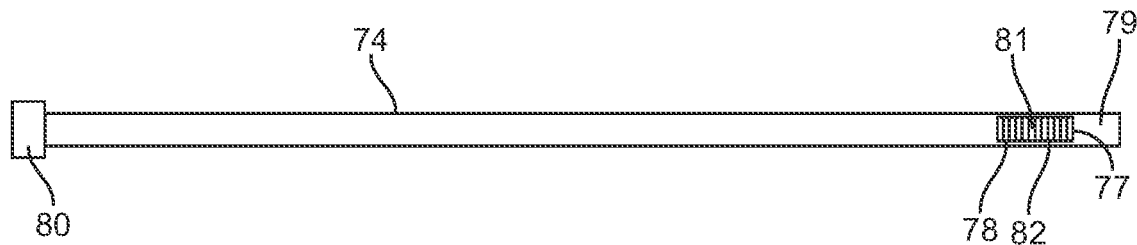
FIG. 27A shows a side view of another exemplary embodiment of an implant before expansion.
Figure 27B:
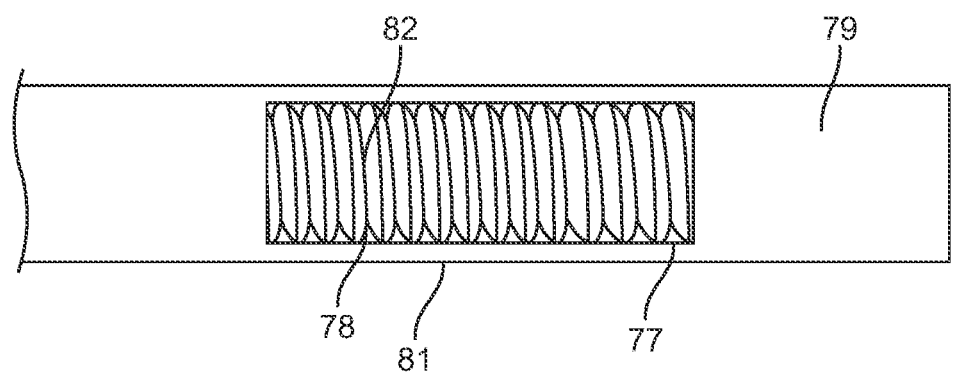
FIG. 27B shows a detailed view of another exemplary embodiment of an implant before expansion.
Figure 27C:
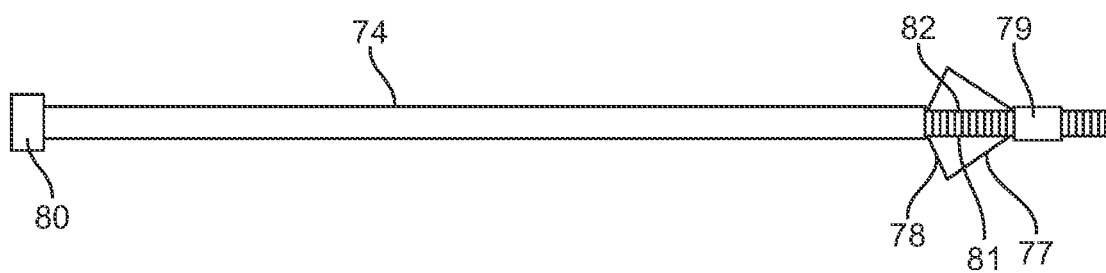
FIG. 27C shows a side view of another exemplary embodiment of an implant after expansion.

FIGS. 27A-27C show another embodiment of an implant for treating fractured bones. FIGS. 27A-27C each illustrate an embodiment with optional features, any of which may be optionally used or substituted with other features in other embodiments discussed herein. FIG. 27A shows a side view of another exemplary embodiment of an implant before expansion. FIG. 27B shows a detailed view of another exemplary embodiment of an implant before expansion. FIG. 27C shows a side view of another exemplary embodiment of an implant after expansion.

The implant may comprise a tubular component 74 and a fastener component 80. The tubular component 74 may be circular. The tubular component 74 may be any shape. The tubular component 74 may have a lumen extending along its length. The tubular component 74 may have a cutout 77 with a side wall 78. The cutout 77 may extend through the entire shaft. The cutout 77 may be rectangular in shape. The cutout 78 may be any shape such that there are side walls 78 on each side. The side walls 78 may be flexible. The side walls 78 may have spots that are prone to bending. The tubular component 74 may have a distal end 79. The lumen of the distal end 79 may be internally threaded (not pictured). A fastener such as a bolt, comprising a head 80, rod 81 and threads 82, may be slidably disposed through the center of tube 74 and threadably engaged with the internal threads of the distal end 79. As the fastener threads into distal end 79, the distal end may be pulled towards the proximal end and the side walls 78 may begin to expand radially outward due to the compression from the fastener threadably engaging the tube 74. In their expanded state, the side walls 78 may be triangular wings. In their expanded state, the side walls 78 may be any shape. The expanded side walls 78 act as anchors into the bone, preventing movement and providing rotational and translational stability. FIG. 27A shows the implant in its uncompressed state, FIG. 27B shows a detailed view of the distal portion of the implant, and FIG. 27C shows the implant in its compressed, or expanded, state. The proximal end of the shaft may be anchored with any anchoring methods disclosed herein.

Figure 28A:
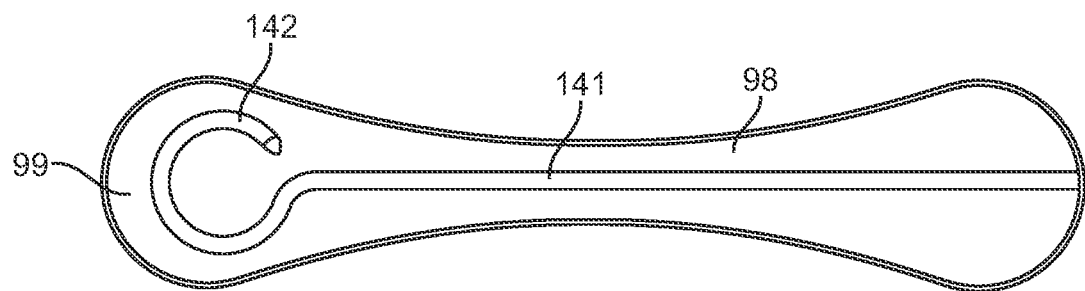
FIG. 28A shows a side view of another exemplary embodiment of an implant after expansion in the intramedullary canal.
Figure 28B:
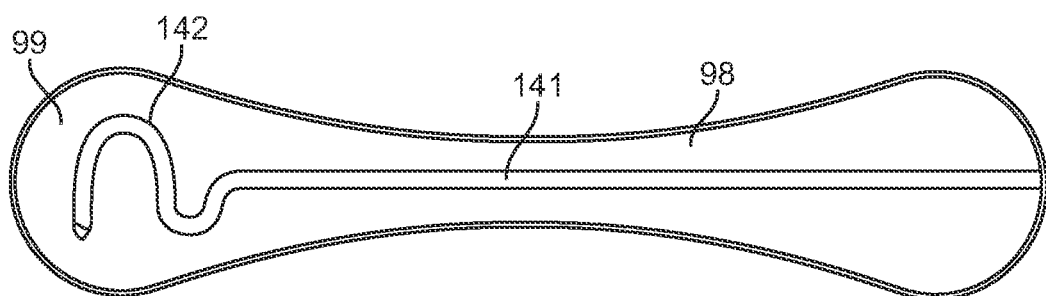
FIG. 28B shows a side view of another exemplary embodiment of an implant after expansion in the intramedullary canal.
Figure 28C:
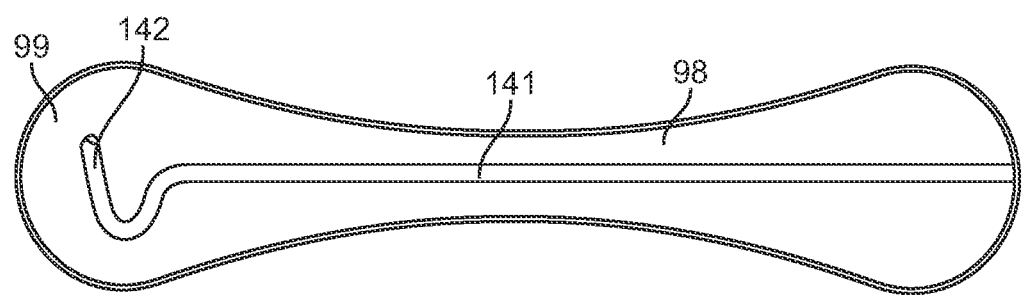
FIG. 28C shows a side view of another exemplary embodiment of an implant after expansion in the intramedullary canal.

FIGS. 28A-28C illustrate alternative embodiments of a fixation implant having different tip geometries for anchoring the tip in bone that may be used in any of the embodiments disclosed herein. FIGS. 28A-28C each illustrate an embodiment with optional features, any of which may be optionally used or substituted with other features in other embodiments discussed herein. FIG. 28A shows a side view of another exemplary embodiment of an implant after expansion in the intramedullary canal. FIG. 28B shows a side view of another exemplary embodiment of an implant after expansion in the intramedullary canal. FIG. 28C shows a side view of another exemplary embodiment of an implant after expansion in the intramedullary canal.

The implant includes an elongate main body 141. The elongate member 141 is preferably circular with a proximal end and distal end. The elongate member 141 is preferably shaped to fit an intramedullary canal 98 and has an end 142 to fit a metaphysis 99. The elongate member 141 may also be of ovular cross-section, square cross-section or any other shape. The elongate member 141 is preferably a solid member but may also be hollow. The elongate member 141 may be available in various lengths to provide for different long bone uses and varying patient anatomy. In some cases, the elongate member 141 may have a length of 100 mm to 150 mm for use in a clavicle. In some cases, the elongate member 141 may have a length of 320 to 370 mm for use in a fibula. The elongate member 141 may be cut to length during implantation. The elongate member 141 may have various diameters to account for different long bone uses and varying patient anatomy. The elongate member 141 preferably has a diameter of 1 mm to 5 mm. More preferably, the elongate member 141 may have a diameter of 1.5 mm to 3.5 mm. The tip 142 may vary in shape. In some cases, it may be a circular shape as shown in FIG. 37A such that the center of the circle sits relatively close to the main axis. The tip 142 may have a plurality of bends as shown in FIGS. 28B and 28C such that there is material on both sides of the main axis. In FIG. 37A the circle may be a closed ring, or an open ring. In FIG. 28B the bends may be sinusoidal or otherwise form an undulating pattern with one or more peaks and valleys. In FIG. 28C the tip 142 may form a crook or J-shaped pattern. The tip 142 of the elongate member 1 may have an expanded state and an unexpanded state such that it may expand inside the metaphysis 99 when implanted. The tip 142 may be naturally in the expanded state. The tip 142 may be naturally in the unexpanded state. The tip 142 may be self-expanding. The tip 142 may be expanded through mechanical, temperature, or other manipulation. Note that the elongate member 141 may be paired with any locking mechanism disclosed herein. The elongate member 141 is preferably rigid across its entire length. The elongate member 141 may be flexible along a portion or all of its length. The elongate member 141 may be nickel titanium or any metal.

Figure 29A:
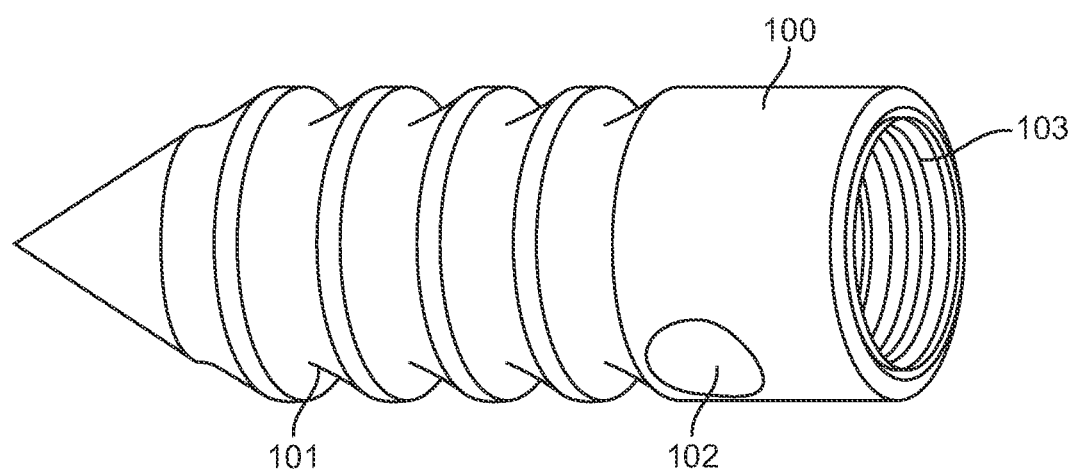
FIG. 29A shows a perspective view of another exemplary embodiment of a threaded component.
Figure 29B:
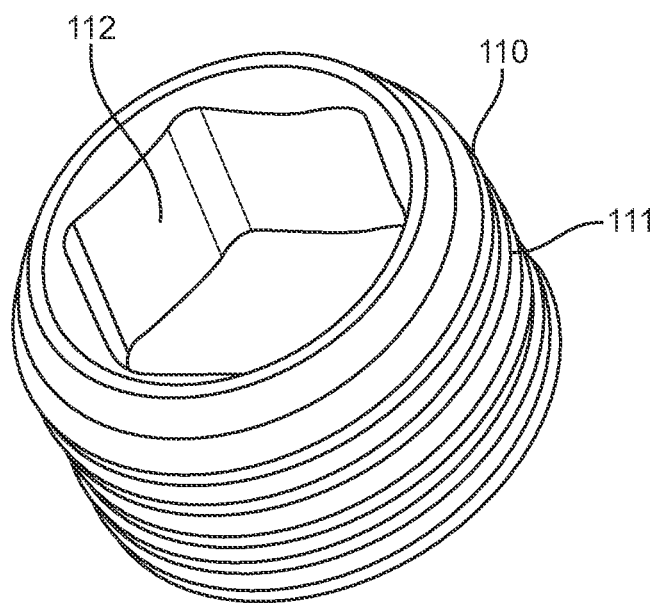
FIG. 29B shows a perspective view of another exemplary embodiment of a locking component.
Figure 29C:
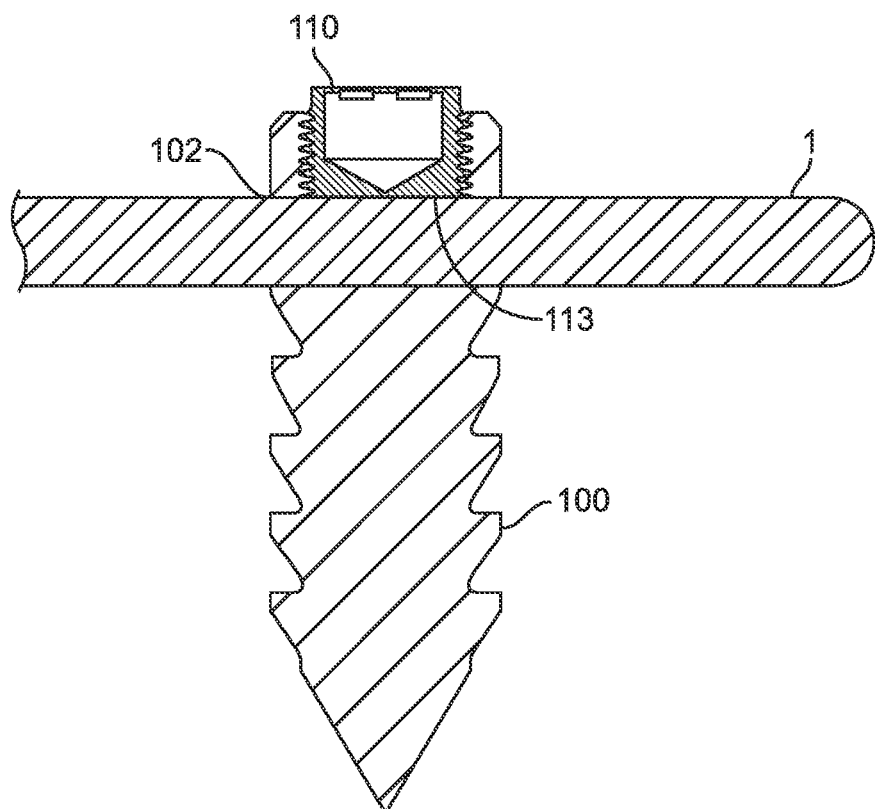
FIG. 29C shows a side view of another exemplary embodiment of a locking mechanism.
Figure 29D:
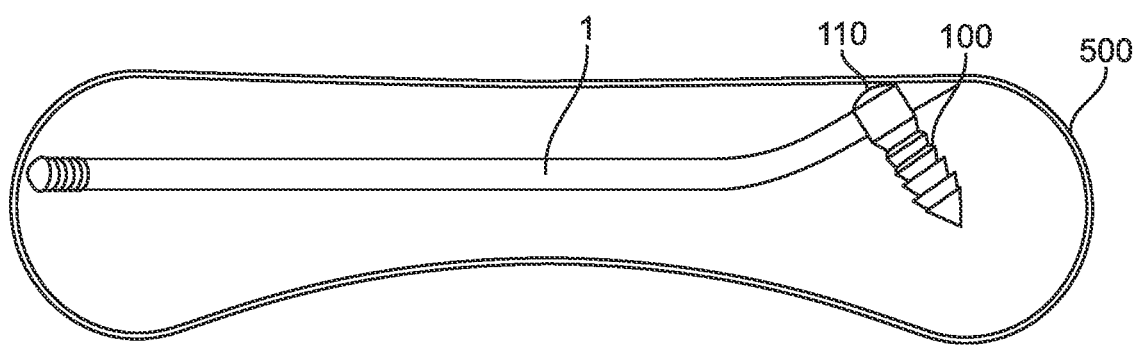
FIG. 29D shows a side view of another exemplary embodiment of an implant in the intramedullary canal.

FIGS. 29A-29D illustrate another exemplary embodiment of a locking mechanism that may be used with any of the fixation implants 1 described herein. FIGS. 29A-29D each illustrate an embodiment with optional features, any of which may be optionally used or substituted with other features in other embodiments discussed herein. The locking mechanism may comprise a bone anchor 100 and set screw 110. FIG. 29A shows a perspective view of another exemplary embodiment of a threaded component. FIG. 29B shows a perspective view of another exemplary embodiment of a locking component. FIG. 29C shows a side view of another exemplary embodiment of a locking mechanism. FIG. 29D shows a side view of another exemplary embodiment of an implant in the intramedullary canal.

FIG. 29A shows an embodiment of a bone anchor 100. The anchor 100 may be cylindrical with a tapered or pointed tip that can be malleted into bone (not pictured) such that its axis is substantially perpendicular or otherwise transverse to the axis of the intramedullary canal. The anchor 100 may comprise one or more circumferential grooves 101 or barbed regions on its outer surface to engage bone and resist migration after anchor 100 placement in the bone. The anchor 100 may also comprise a through hole 102 substantially perpendicular to the anchor's main axis to receive an elongate member (not pictured) and internal thread 103 in line with the anchor's main axis to receive a set screw (not pictured).

FIG. 29B shows an embodiment of a set screw 110. The set screw 110 may comprise an external thread 111 to engage with an anchor (not pictured) and hex socket or equivalent driving feature 112 to engage with a driver (not pictured).

FIG. 29C shows the bone anchor 100 as described in FIG. 29A and the set screw 110 as described in FIG. 29B with an elongate hollow member 1. The set screw 110 may further comprise a distal or bottom surface 113. The bottom surface 113 may engage the elongate member 1 to prevent motion of the elongate member 1 relative to the anchor 100. In use, the elongate member 1 may be disposed into the bone (not pictured) and the anchor 100 may threadably engage with bone. The elongate member 1 may be inserted into hole 102 on the anchor and the set screw 110 may be threadably engaged with the bone anchor 100 to hold the elongate member 1 and prevent movement.

FIG. 29D shows the embodiment described in FIGS. 29A-C. The anchor 100 and set screw 110 are preferably driven into the bone 500 deep enough so that they either are flush with the outer surface of bone being treated or are below the outer surface of the bone. The distal end of the elongate member 1 may be anchored to the bone with any of the distal anchoring features described herein.

Figure 30A:
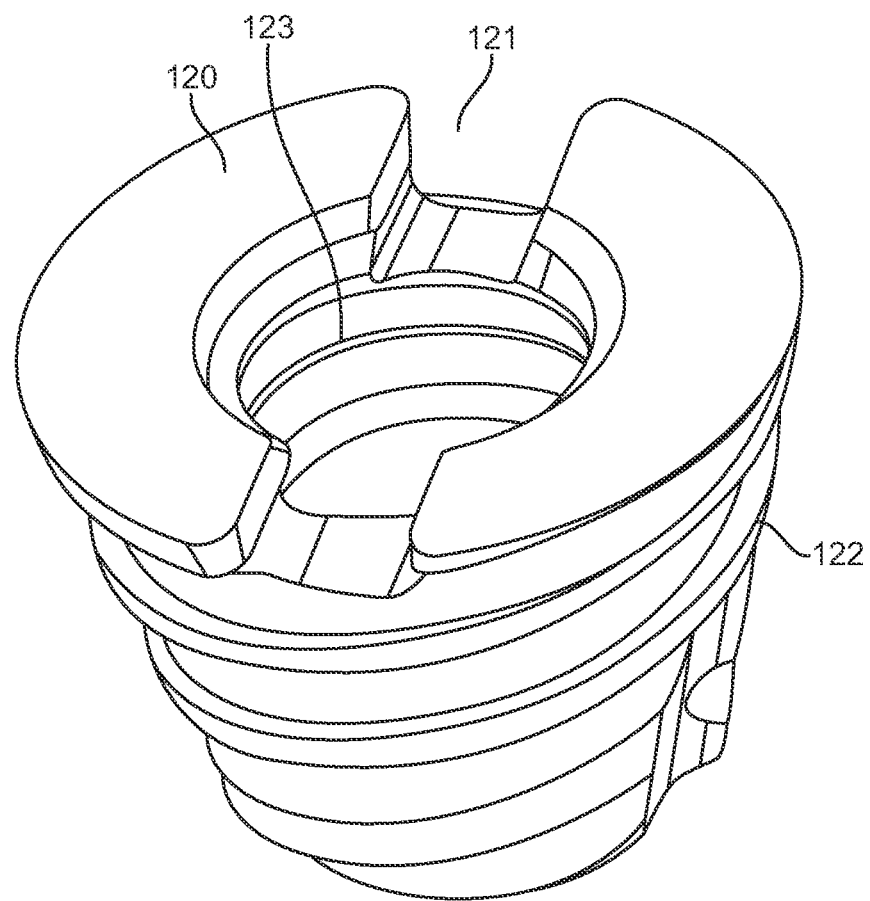
FIG. 30A shows a perspective view of another exemplary embodiment of a threaded component.
Figure 30B:
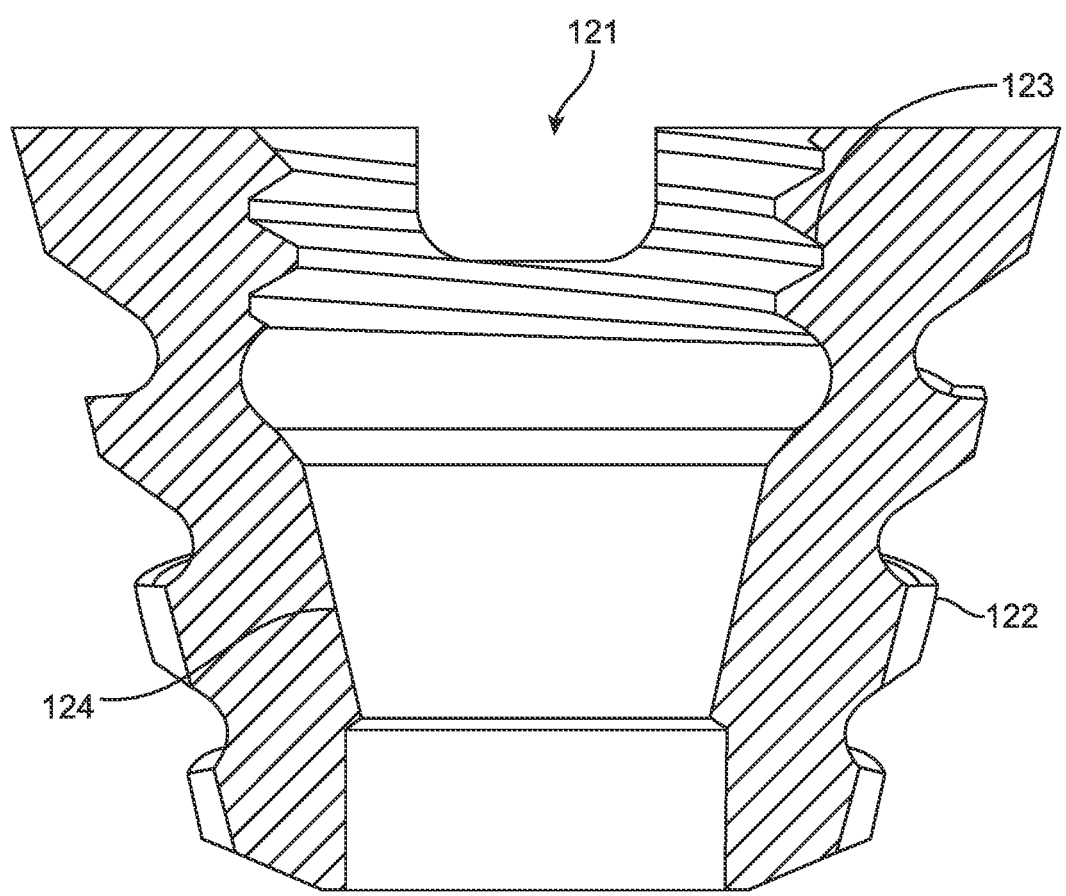
FIG. 30B shows a side view of another exemplary embodiment of a threaded component.
Figure 30C:
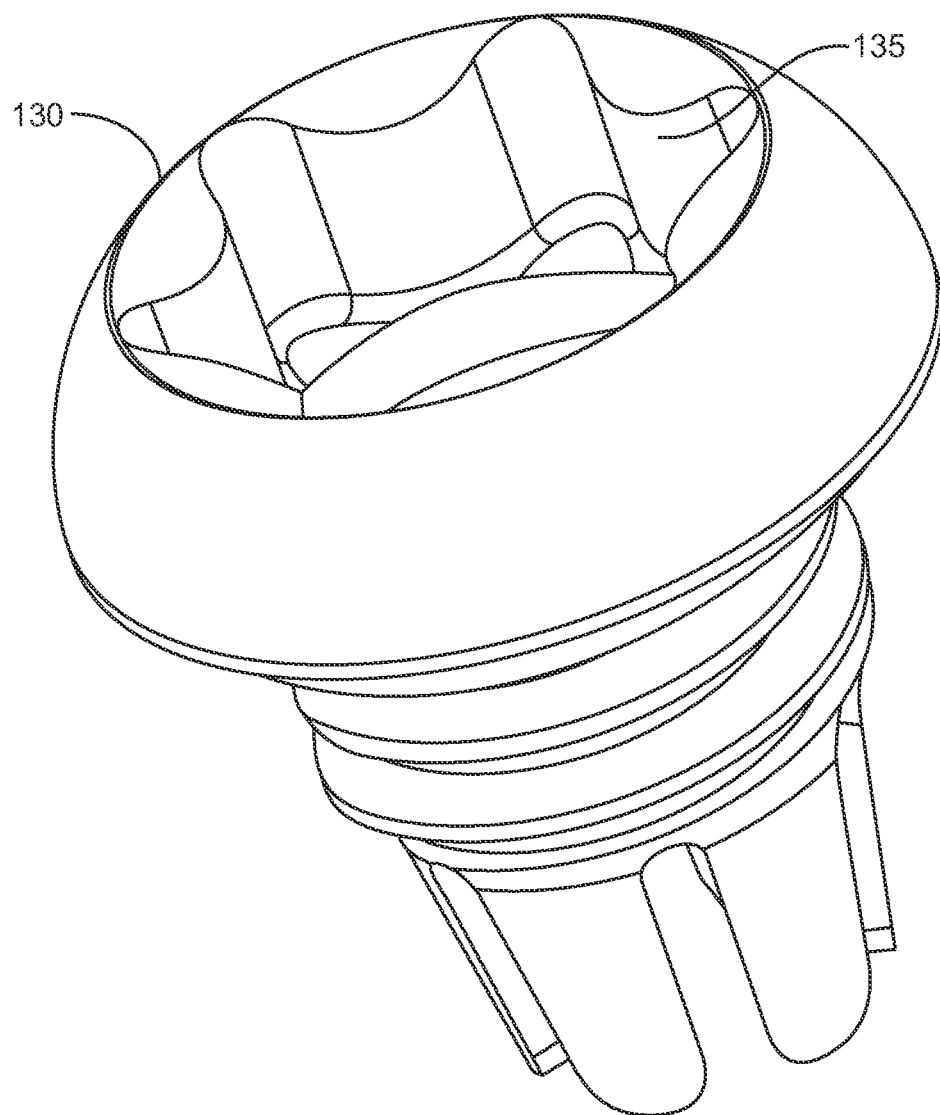
FIG. 30C shows a perspective view of another exemplary embodiment of a locking component.
Figure 30D:
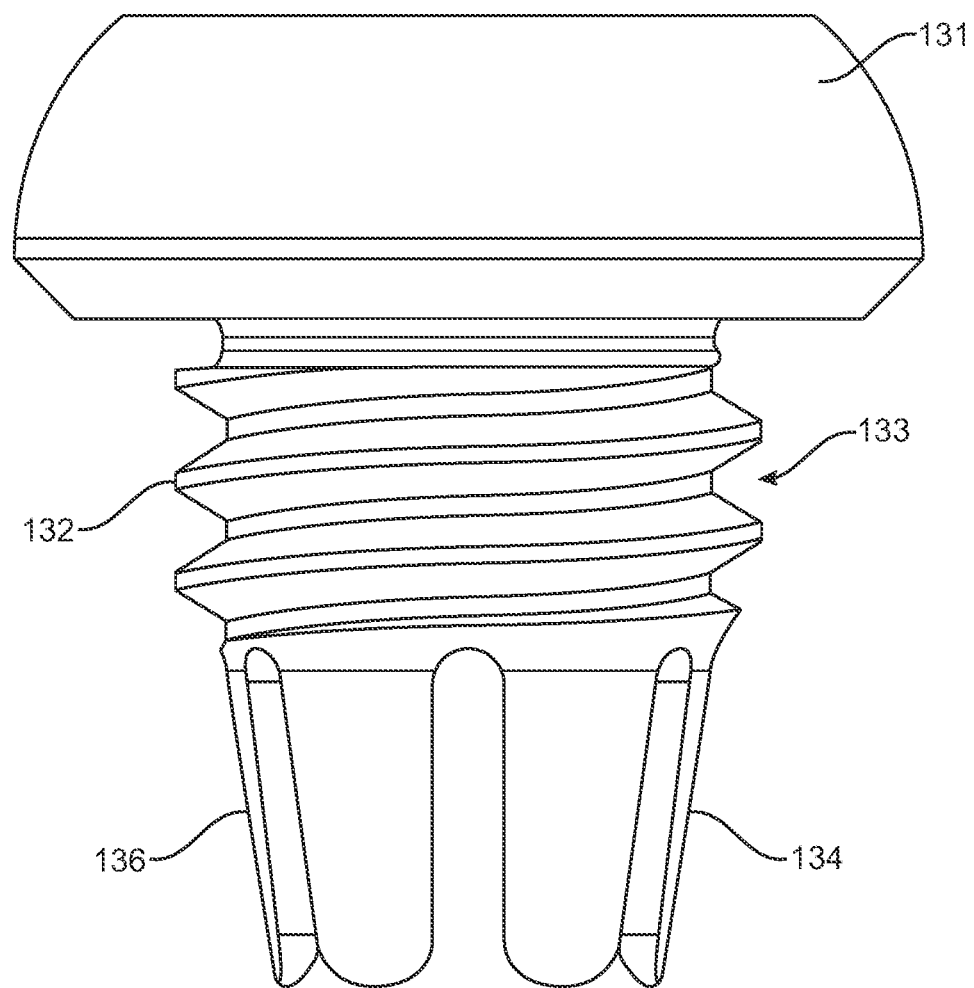
FIG. 30D shows a side view of another exemplary embodiment of a locking component.
Figure 30E:
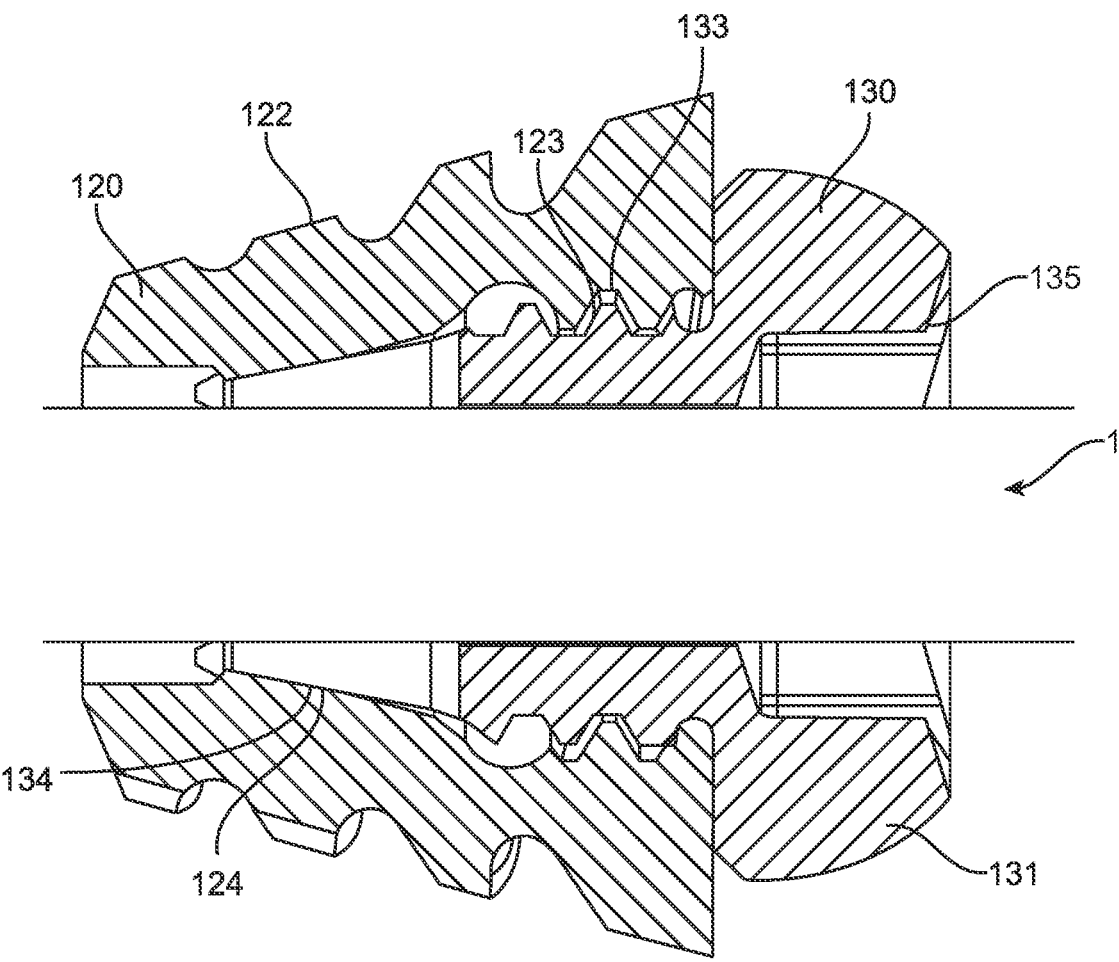
FIG. 30E shows a side view of another exemplary embodiment of a locking mechanism and implant.
Figure 30F:
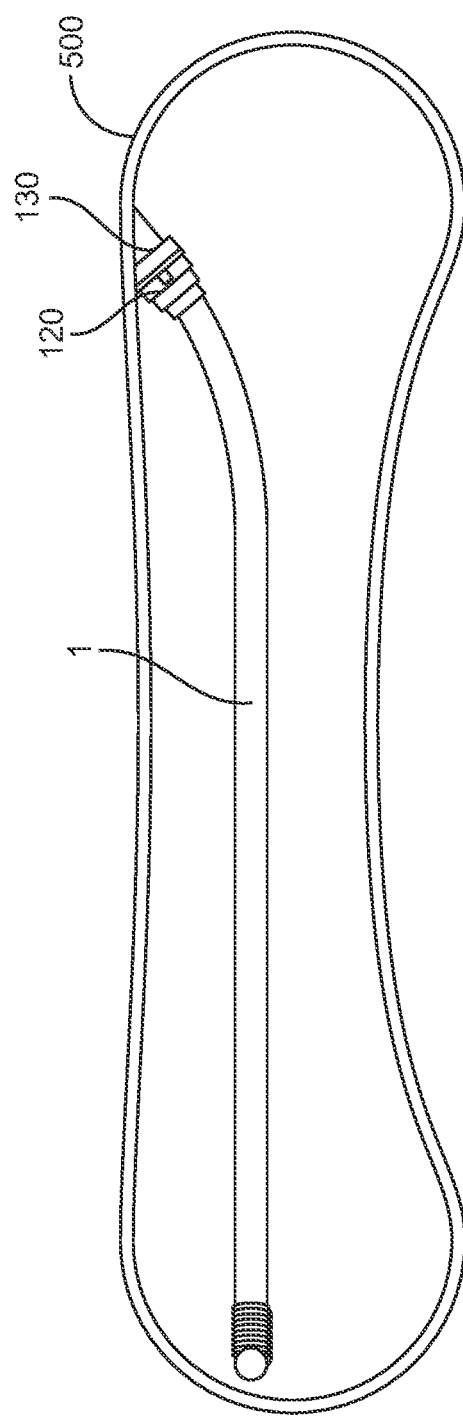
FIG. 30F shows a side view of another exemplary embodiment of an implant in the intramedullary canal.

FIGS. 30A-30F show another embodiment of a locking mechanism that may be used with any of the fixation implants described herein. FIGS. 30A-30F each illustrate an embodiment with optional features, any of which may be optionally used or substituted with other features in other embodiments discussed herein. The locking mechanism may be comprised of bone screw 120 and locking screw 130. FIG. 30A shows a perspective view of another exemplary embodiment of a threaded component. FIG. 30B shows a side view of another exemplary embodiment of a threaded component. FIG. 30C shows a perspective view of another exemplary embodiment of a locking component. FIG. 30D shows a side view of another exemplary embodiment of a locking component. FIG. 30E shows a side view of another exemplary embodiment of a locking mechanism and implant. FIG. 30F shows a side view of another exemplary embodiment of an implant in the intramedullary canal.

FIGS. 30A and 30B show a perspective view and front cross-section, respectively, of a bone screw 120. The bone screw 120 may be conical in shape but may be any other shape. The bone screw 120 may be cannulated, allowing it to slide onto an elongate member (not pictured). The bone screw 120 preferably has a length of 2 mm to 10 mm. More preferably, the bone screw 120 has a length of 3 mm to 9 mm. The bone screw 120 cannulation is preferably sized to have a sliding fit with the elongate member. The bone screw 120 preferably has an inner diameter of 1 mm to 8 mm. More preferably, the inner diameter is 2 mm to 7 mm. The bone screw 120 may also comprise a slot 121 or similar feature to engage with a driver. The bone screw 120 may comprise an external bone thread 122. The external thread 122 may extend along the majority of the length of the screw axis for fixation to bone (not pictured). The external thread 122 may extend the entire length. The bone screw 120 may also comprise an internal thread 123 along a partial length of the screw axis to receive a locking screw (not pictured). The bone screw 120 may comprise an internal tapered surface 124 along an adjacent partial length of the screw axis. The bone screw 120 may be titanium, a titanium alloy, or any metal. The bone screw 120 may be a polymer or ceramic.

FIGS. 30C and 30D show a perspective and front view, respectively, of a locking screw 130. The locking screw 130 may also be cannulated to slide over an elongate member (not pictured). The locking screw 130 may comprise a head 131, cylindrical body 132, and tapered end 136. The body 132 may comprise an external thread 133 sized to engage with the internal thread on the bone screw (not pictured). The tapered end 136 may be comprised of a plurality of tabs 134. The plurality of tabs 134 are preferably substantially rectangular in shape, preferably extend parallel to the main axis, and are patterned circumferentially around the main axis. The head 131 may comprise a Torx T15 socket 135 or similar feature to engage with a driver. The locking screw 130 may be made in multiple pieces or may be integrally formed. The locking screw 130 may be titanium, a titanium alloy, or any metal. The locking screw 130 may be a polymer or ceramic.

FIG. 30E shows a front cross-section of the locking mechanism, with bone screw 120 and locking screw 130, on an elongate member 1. The bone screw 120 may be driven over the elongate member 1 such that the external threads 122 engage the surrounding bone (not pictured). The locking screw 130 may be driven by the torx socket 135 towards the bone screw 120, with the locking screw 130 external threads 133 threadably engaging with the bone screw 120 internal threads 123. The tabs 134 may hit the bone screw 120 internal surface 124 and flex inward, clamping on the elongate member 1 to hold it in position and prevent movement. The locking screw 130 head 131 may prevent the locking screw 130 from being driven past the bone screw 120.

FIG. 30F shows the implantation configuration on a long bone 500. The bone screw 120 and locking screw 130 may be disposed below the outer surface of the bone 500 being treated or they may be flush with the bone's outer surface. The distal end of the elongate member 1 may be anchored to the bone with any of the distal anchoring features described herein.

Figure 31:
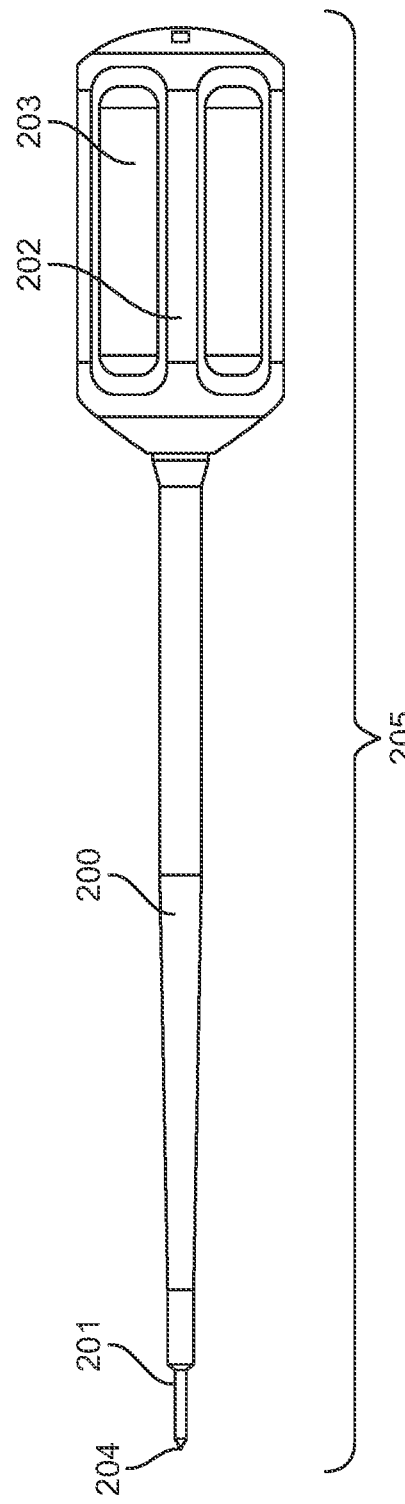
FIG. 31 shows a side view of an exemplary embodiment of an awl.

FIG. 31 shows a side view of an exemplary embodiment of an awl. FIG. 31 illustrates an embodiment with optional features, any of which may be optionally used or substituted with other features in other embodiments discussed herein. In particular, FIG. 31 shows an embodiment of an awl 205 for piercing the cortical shell of a bone. The awl 205 may comprise a shaft 200 with a tip 201 on one end and handle 202 on the other. The shaft 200 may be circular along its entire length. The shaft 200 may be any shape. The shaft 200 is preferably solid but may also be hollow. The shaft 200 preferably has a length of 100 mm to 300 mm. More preferably, the shaft 200 has a length of 120 mm to 160 mm. The shaft 200 may have length markings. The shaft 200 may have a uniform diameter across its length. The shaft 200 may have a diameter that decreases from the handle 202 to the tip 201. The shaft 200 preferably has a diameter of 2 mm to 15 mm. More preferably, the shaft 200 has a diameter of 3 mm to 10 mm. The tip 201 may be disposed on one end of the shaft 200. The tip 201 may have a sharp pointed end 204. The pointed end 204 may pierce the cortical shell of bone. The tip 201 preferably has a length of 5 mm to 15 mm. More preferably, the tip 201 has a length of 7 mm to 12 mm. The tip 201 may have a rectangular cross-section along its length, terminating at a sharp point. The tip 201 may be any shape. The tip 201 may be straight along its longitudinal axis. The tip 201 may be curved. The tip 201 preferably has a maximum diameter or width of 2 mm to 10 mm. More preferably, the tip 201 has a maximum diameter or width of 2 mm to 6 mm. The shaft 200 and tip 201 may be manufactured as one piece. The shaft 200 and tip 201 may be joined by mechanical mechanisms, bonding, or any other method of adjoining two pieces. The shaft 200 and tip 201 are preferably the same material but may also be different materials. The shaft 200 and tip 201 may be stainless steel or any other metal, polymer, or ceramic. The handle 202 may be disposed on the other end of the shaft 200. The handle 202 may be a cylindrical shape. The handle 202 may be any shape. The handle 202 is preferably 40 mm to 100 mm in length. More preferably, the handle 202 has a length of 50 mm to 70 mm. The handle 202 preferably has a diameter of 20 mm to 100 mm. More preferably, the handle 202 has a diameter of 40 mm to 60 mm. The handle 202 may have a plurality of grooves 203 located circumferentially around to provide for easier handling. There are preferably four to ten grooves 203. More preferably, there are five to seven grooves 203. The grooves 203 may be ovular in shape. The grooves 203 may be any shape. The grooves 203 are preferably 30 mm to 90 mm in length. More preferably, the grooves 203 are 40 mm to 60 mm in length. The handle 202 may be radel or any type of polymer. The handle 202 may be a metal or ceramic. The handle 202 and shaft 200 may be joined by mechanical mechanisms, bonding, press fit, or any other method of adjoining two pieces.

Figure 32:
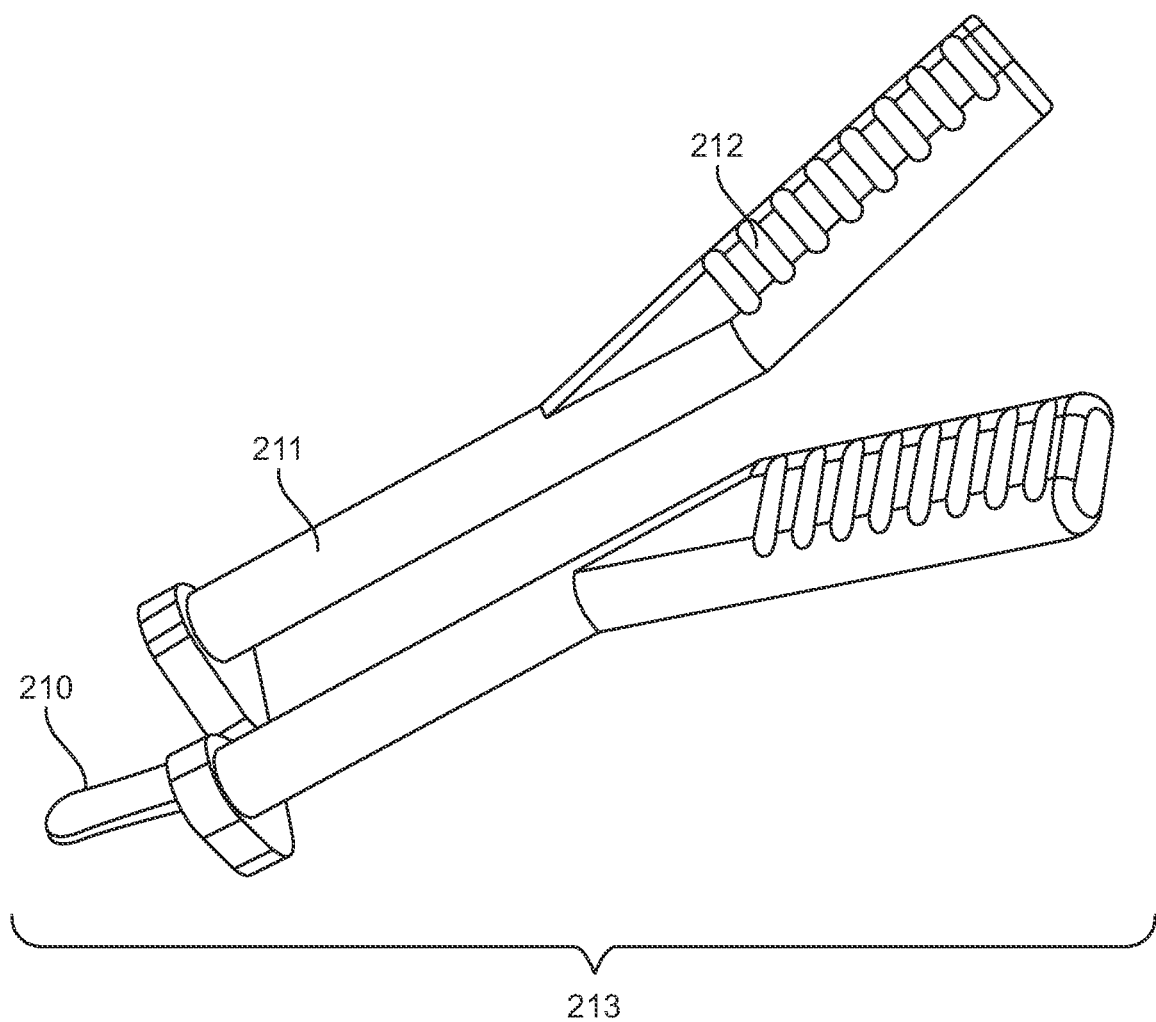
FIG. 32 shows a perspective view of an exemplary embodiment of a marker.

FIG. 32 shows a perspective view of an exemplary embodiment of a marker. FIG. 32 illustrates an embodiment with optional features, any of which may be optionally used or substituted with other features in other embodiments discussed herein. In particular, FIG. 32 shows an embodiment of a marker 213 to maintain the entry path into the cortical shell of a bone. The marker 213 comprises a guiding end 210 and one or more wings 211. The guiding end 210 may be an elongate member with c-shaped cross section. The guiding end 210 may have a shape and size to accommodate other instruments. The guiding end 210 may be curved. The guiding end 210 may be straight. There may be one or more wings 211 that are attached to the one end of the guiding end 210. The wings 211 may be positioned at a distance on either side or around the guiding end 210 so as not to interfere with the pathway created by its shape. The wings 211 may be straight shafts along a longitudinal axis. The wings 211 may be straight along a longitudinal axis partially along their length. The wings 211 may bend outward from the longitudinal axis at any point along their length. The wings 211 preferably bend outward at an angle of 10 degrees to 50 degrees. More preferably, the wings 211 bend outward at an angle of 15 degrees to 30 degrees. The wings 211 may have a uniform cross section along their length. The wings 211 may have a transitioning cross section from one shape to another along their length. The wings 211 may be circular, ovular, rectangular, or any other shape. The wings 211 may have a plurality of grooves 212 traversing the length of the wings 211 to provide for easier handling. There are preferably five to fifteen grooves 212. More preferably, there are five to ten grooves 212. The grooves 212 may be ovular in shape. The grooves 212 may be any shape. The grooves 212 preferably have a width of 0.5 mm to 5 mm. More preferably, the grooves 212 have a width of 1 mm to 3 mm. The marker 213 may be radel or any type of polymer. The marker 213 may be a metal or ceramic.

Figure 33:
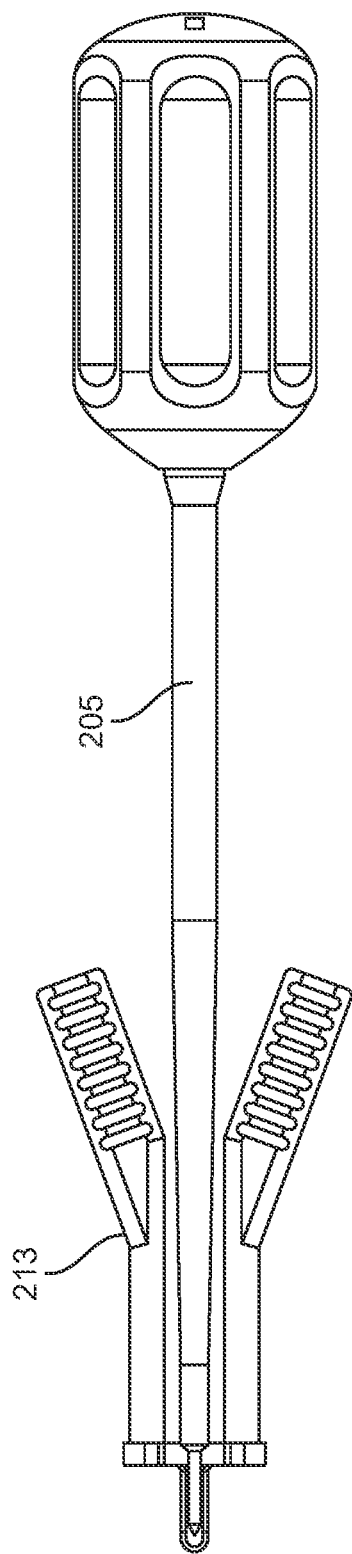
FIG. 33 shows a side view of an exemplary embodiment of an awl and marker.

FIG. 33 shows a side view of an exemplary embodiment of an awl and marker. FIG. 33 illustrates an embodiment with optional features, any of which may be optionally used or substituted with other features in other embodiments discussed herein. In particular, FIG. 33 shows an embodiment of the awl 205 as described in FIG. 31 and an embodiment of the marker 213 as described in FIG. 32. FIG. 33 shows how the marker 213 may be interact with the awl 205. The awl 205 may pierce the cortical bone (not pictured) and the marker 213 may be inserted around the awl 205 to mark the position of the pierced bone. The marker 213 may be sized and shaped to receive the awl 205 and/or other instruments.

Figure 34:
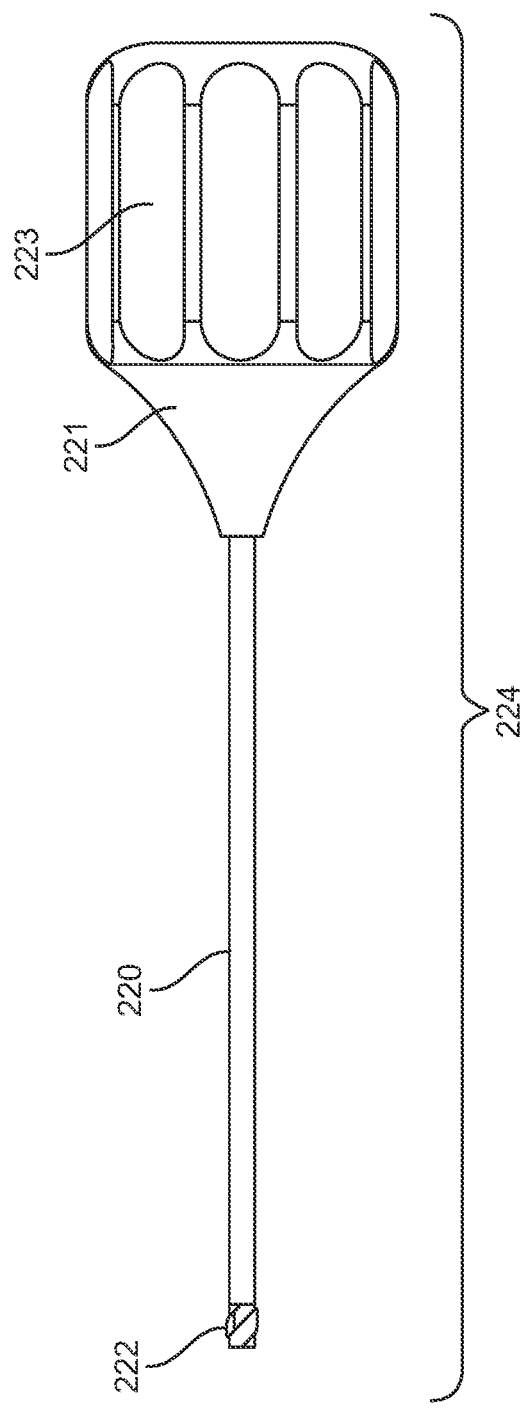
FIG. 34 shows a side view of an exemplary embodiment of a reamer.

FIG. 34 shows a side view of an exemplary embodiment of a reamer. FIG. 34 illustrates an embodiment with optional features, any of which may be optionally used or substituted with other features in other embodiments discussed herein. In particular, FIG. 34 shows an embodiment of a reamer 224. The reamer 224 may comprise a shaft 220 with a tip 222 at one end and handle 221 on the other. The shaft 220 is preferably cannulated along the entire length of the shaft 200. The shaft 220 may also be cannulated partially along its length. The shaft 220 may have a uniform outer diameter along its length. The shaft 220 may also have variable outer diameters across its length. The outer diameter of the shaft 220 is preferably 1 mm to 6 mm. More preferably, the diameter of the shaft 220 is 2 mm to 5 mm. The shaft 220 may be stainless steel or any other metal. The shaft 220 may be any polymer or ceramic. The tip 222 of the shaft 220 may have external cutting flutes along the length of the tip 222. The flutes may be designed for reaming the medullary canal of bone. The tip 222 preferably has a length of 3 mm to 10 mm. More preferably, the tip 222 has a length of 4 mm to 6 mm. The handle 221 may be disposed on the other end of the shaft 220. The handle 221 may be cylindrical in shape. The handle 221 may be any other shape. The handle 221 may have a uniform diameter across its length. The handle 221 may have a decreasing diameter, sloping towards the diameter of the shaft 220. The handle 221 preferably has a diameter of 1 mm to 100 mm. More preferably, the handle 221 has a diameter of 3 mm to 60 mm. The handle 221 is preferably 40 mm to 100 mm in length. More preferably, the handle 221 has a length of 50 mm to 70 mm. The handle 221 may have a plurality of grooves 223 located circumferentially around to provide for easier handling. There are preferably four to fifteen grooves 223. More preferably, there are five to twelve grooves 223. The grooves 223 may be ovular in shape. The grooves 223 may be any shape. The grooves 223 are preferably 30 mm to 90 mm in length. More preferably, the grooves 223 are 40 mm to 60 mm in length. The handle 221 may be radel or any type of polymer. The handle 221 may be a metal or ceramic. The handle 221 and shaft 220 may be joined by mechanical mechanisms, bonding, press fit, or any other method of adjoining two pieces.

FIGS. 35A-35B show an embodiment of an inserter 245. FIGS. 35A and 35B each illustrate an embodiment with optional features, any of which may be optionally used or substituted with other features in other embodiments discussed herein. FIG. 35A shows a side view of an exemplary embodiment of an inserter. FIG. 35B shows a cross-section view of an exemplary embodiment of an inserter. The inserter 245 may comprise a sheath 230, a handle 231, a locking knob 232, an axial knob 233, and a handle tip 234. The sheath 230 may be tubular with cannulation throughout its entire length. The sheath 230 is preferably flexible. The sheath 230 may also be rigid. The sheath tip 240 may have a jagged edge. The sheath tip 240 may have a profile similar to that of a cutting flute to ream the medullary canal of bone. The sheath tip 240 may be substantially parallel with the sheath 230. The sheath tip 240 may be curved. The length of the sheath 230 is preferably 100 mm to 400 mm. The length of the sheath 230 may be dependent on the anatomy of the patient and the type of bone. The outer diameter of the sheath 230 is preferably 1 mm to 10 mm. More preferably, the outer diameter of the sheath 230 is preferably 2 mm to 5 mm. The inner diameter of the sheath 230 is preferably 0.5 mm to 8 mm. More preferably, the inner diameter of the sheath 230 is 1 mm to 5 mm. The sheath 230 may be nickel titanium. The sheath 230 may be any metal, polymer, or ceramic.

The handle 231 is preferably cylindrical. The handle 231 may be any shape. The handle 231 may be hollow with internal threads 235. The threads 235 may have a pitch of 1 mm to 3 mm. The threads 235 may have a standard profile. The handle 231 may have a uniform outer diameter across its entire length. The handle 231 may have a decreasing outer diameter on one end. The handle 231 outer diameter is preferably 15 mm to 60 mm. More preferably, the handle 231 outer diameter is 20 mm to 50 mm. The handle 231 may have a uniform inner diameter across its entire length. The handle 231 may have a decreasing inner diameter on one end. The handle 231 inner diameter is preferably 3 mm to 20 mm. More preferably, the inner diameter is 5 mm to 10 mm. The handle 231 may have a plurality of grooves 238 circumferentially around its outer diameter to provide for easier handling. There are preferably two to ten grooves 238. More preferably, there are three to six grooves 238. The grooves 238 may be ovular in shape. The grooves 238 may be any shape. The grooves 238 may cut through the inner diameter of the handle 231 to create a viewing hole. The grooves 238 are preferably 30 mm to 90 mm in length. More preferably, the grooves 238 are 40 mm to 60 mm in length. The handle 231 may be radel or any type of polymer. The handle 231 may be a metal or ceramic.

The locking knob 232 may have a shaft 242 and a top end 243. The locking knob 232 may be cylindrical. The locking knob 232 may be cannulated. The locking knob 232 preferably has an inner diameter of 1.5 mm to 10 mm. More preferably, the inner diameter is 3 mm to 6 mm. The shaft 242 may have external threads 236. The shaft 242 may be threaded along its entire length. The shaft 242 may be threaded partially along its length. The external threads 236 may be sized to mate with the internal threads 235 of the handle 231. The shaft 242 preferably has a length of 2 mm to 8 mm. More preferably, the shaft 242 may have a length of 2 mm to 5 mm. The shaft 242 may be tapered at the end. The top end 243 preferably has a diameter of 10 mm to 30 mm. More preferably, the top end 243 has diameter of 15 mm to 25 mm. The top end 243 preferably has a length of 7 mm to 20 mm. More preferably, the top end 243 has a length of 7 mm to 12 mm. The top end 243 may have a plurality of grooves 239 circumferentially around its outer diameter to provide for easier handling. There are preferably eight to thirty grooves 239. More preferably, there are ten to twenty grooves 239. The grooves 239 may be ovular in shape. The grooves 239 may be any shape. The grooves 239 are preferably 5 mm to 15 mm in length. More preferably, the grooves 239 are 5 mm to 10 mm in length. The locking knob 232 may be radel or any type of polymer. The locking knob 232 may be a metal or ceramic.

The axial knob 233 may be a flat ovular shape. The axial knob 233 may be any shape. The axial knob 233 may have an inner cannulation 244. The inner cannulation 244 may be round. The inner cannulation 244 may have one or more flat surfaces to interface with a flat surface on the elongate member (not pictured) for increased rotational control. The inner cannulation 244 may be any shape. The inner cannulation 244 may span partially across the length of the axial knob 233. The length of the axial knob 233 is preferably 10 mm to 50 mm. More preferably, the length is 20 mm to 40 mm. The width of the axial knob 233 is preferably 10 mm to 50 mm. More preferably, the width is 20 mm to 40 mm. The axial knob 233 may be radel or any type of polymer. The axial knob 233 may be a metal or ceramic.

The handle tip 234 may be cylindrical. The handle tip 234 may be cannulated. The handle tip 234 preferably has an inner diameter of 1.5 mm to 10 mm. More preferably, the inner diameter is 3 mm to 6 mm. The handle tip 234 may have external threads 237. The external threads 237 may extend partially along the length of the handle tip 234. The external threads 237 may extend along its entire length. The external threads 237 may be sized to mate with the internal threads 235 of the handle 231. The handle tip 234 preferably has a length of 10 mm to 70 mm. More preferably, the handle tip 234 has a length of 20 mm to 60 mm. The handle tip 234 may be tapered at either or both ends. The outer diameter of the handle tip 234 may be constant across its length. The outer diameter of the handle tip 234 may be variable across its length. The outer diameter is preferably 2 mm to 40 mm. More preferably, the outer diameter is 2 mm to 30 mm. The handle tip 234 may have a plurality of tangs 241 at one end. The tangs 241 may be formed by a slot between material to create a flexible member. There are preferably between two and eight tangs 241. More preferably, there are between three and six tangs 241. With outward-to-inward pressure, the tangs 241 may collapse inward. The tangs 241 preferably have a length of 5 mm to 15 mm. More preferably, the tangs have a length of 5 mm to 10 mm. The handle tip 241 may be radel or any type of polymer. The handle tip 241 may be a metal or ceramic.

The inserter 245 may be assembled with the handle tip 234 being threadably inserted into one end of the handle 231. The sheath 230 may be inserted by passing the non-tip end through the inner lumen of the handle tip 234 so that it passes part way through. The sheath 230 may be adhered to the handle tip 234 by mechanical locking, bonding, welding, or using any other adhesion method. The locking knob 232 may be threadably inserted into the other end of the handle 231. Any embodiments of the elongate member 1 described herein may be used. The elongate member 1 proximal end may be inserted through the sheath 230 tip 240, through the handle 231, handle tip 234, extending past the locking knob 232. The elongate member 1 proximal end may be inserted through the handle 231 to the end of the sheath 230 tip 240. The distal end (not pictured) of the elongate member 1 may be inserted into the sheath 230 such that it remains in its unexpanded state. The axial knob 233 may slide onto the elongate member 1 via its inner cannulation 244 for easy handling. The top end 243 of the locking knob 232 may be twisted in the clockwise direction, causing the locking knob 232 to traverse the handle 231 internal threads 235. The inner cannulation of the locking knob 232 may come in contact with the outer surface of the handle tip 234 tangs 241, providing an outward-to-inward force that may cause the tangs 241 to clamp down on the elongate member 1. Thus, the elongate member 1 may be restricted from axial and radial movement.

During use, the inserter 245 may be forcibly pushed into the medullary canal of the bone (not pictured). Once in place, the top end 243 of the locking knob 232 may be twisted in a counter-clockwise direction to release the handle tip 234 tangs 241 and release the elongate member 1. The elongate member 1 may be manually held in place in the bone (not pictured) while the inserter 245 is removed, allowing the elongate member 1 to expand in the intramedullary canal.

Figure 36:
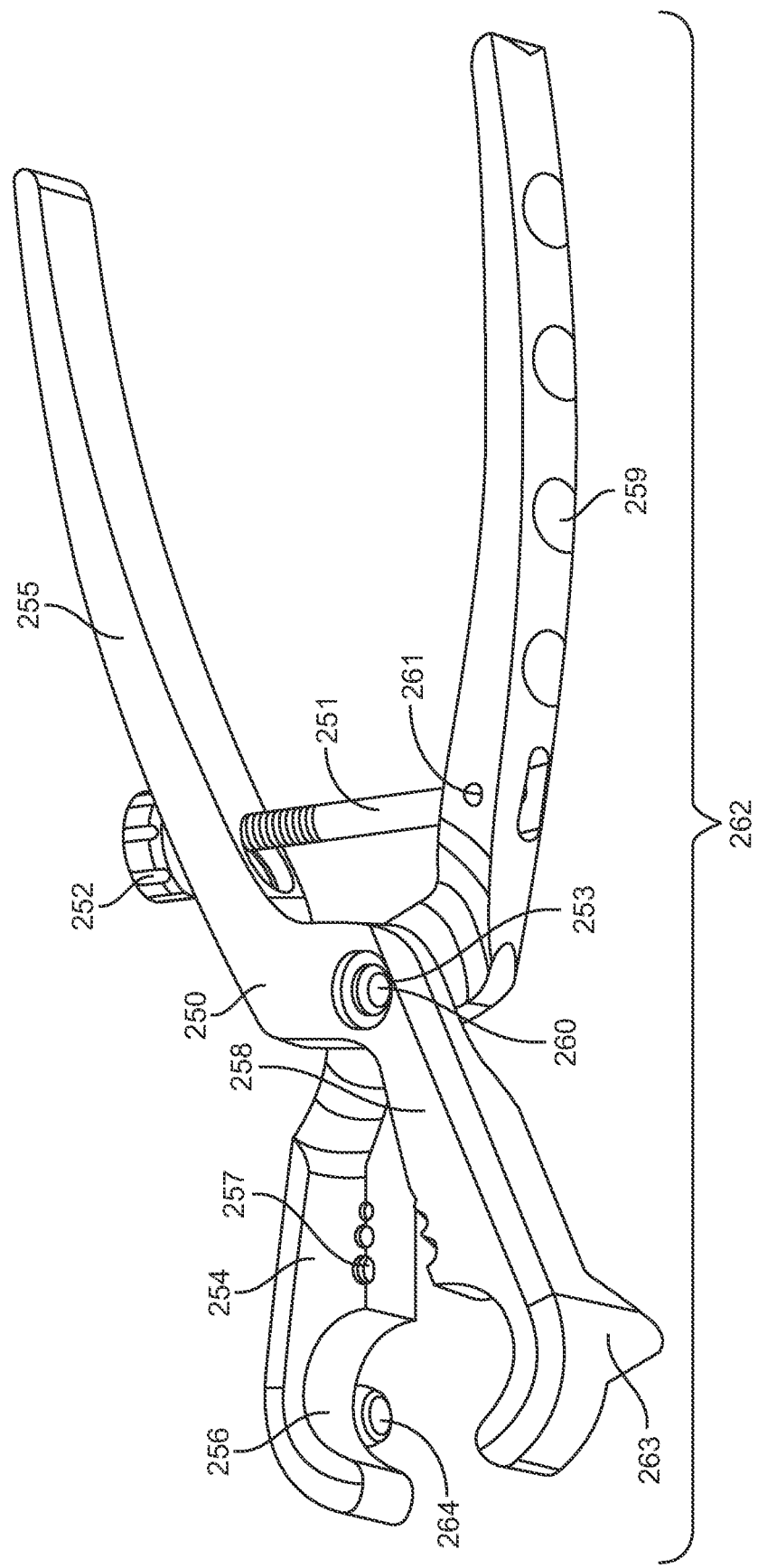
FIG. 36 shows a perspective view of an exemplary embodiment of an impaction accessory.

FIG. 36 shows a perspective view of an exemplary embodiment of an impaction accessory. FIG. 36 illustrates an embodiment with optional features, any of which may be optionally used or substituted with other features in other embodiments discussed herein. In particular, FIG. 36 shows an embodiment of an impaction attachment 262. The impaction attachment 262 comprises two arms 250, 258, a crossbar 251, a nut 252, and a screw 260. The arms 250, 258 may have a working end 254 and a handle 255. The working end 254 and handle 255 are substantially parallel but are offset, preferably by 10 mm to 50 mm. More preferably, they are offset by 15 mm to 30 mm. The working end 254 preferably has a length of 40 mm to 70 mm. More preferably, the working end 254 has a length of 45 mm to 65 mm. The working end 254 may have a cross-sectional shape and size that varies along its length. The working end 254 may have a rectangular cross section or any other shape. The working end 254 may have an instrument clamp 256 and one or more of wire clamps 257. The instrument clamp 256 may be a hole in a semi-circle shape. The instrument clamp 256 may span through the entire thickness of the arm 250, 258. The instrument clamp 256 may be disposed on the internal end (i.e. side in which the handle 255 is offset) of the working end 254, such that as the working ends 254 of the two arms 250, 258 come together, the clamps 256 become circular. The instrument clamp 256 may be sized to interface with or clamp to any instrument disclosed herein. The instrument clamp 256 preferably has a diameter of 10 mm to 60 mm. More preferably, the diameter is 15 mm to 40 mm. The instrument clamp 256 may have one or more clamp extensions 263. The extension 263 may extend from the sides of the clamp 256 in one direction. The extension 263 may be rectangular in shape. The extension 263 may be any shape. The extension 263 may comprise an inwardly extending component 264. The inwardly extending component 264 may be sized and configured to engage with any instrument disclosed herein. The component 264 may constrain the instrument to create rotational alignment between the instrument and the impaction attachment 262. There are preferably one to five wire clamps 257 of varying sizes. The wire clamps 257 may be a hole in a semi-circle shape. The wire clamps 257 may span partially through the thickness of the arms 250, 258. The wire clamp 257 may be disposed on the internal end of the working end 254, such that as the working ends 254 of the two arms 250, 258 come together, the clamps 257 become circular. The wire clamps 257 preferably have diameters of 1 mm to 5 mm. More preferably, the wire clamps 257 have diameters of 1 mm to 4 mm. The instrument clamp 256 and wire clamps 257 may be positioned in line with one another. The handle 255 preferably has a length of 50 mm to 200 mm. More preferably, the handle 255 has a length of 100 mm to 150 mm. The handle 255 may have a cross-sectional size and shape that varies along its length. The handle 255 may have a rectangular cross section or any other shape. The handle 255 may be curved along its length or it may be straight. The handle 255 may be shelled out on its internal surface. The handle 255 may have a plurality of grooves 259 along its length to provide for easier handling. The grooves 259 preferably have a width of 5 mm to 20 mm. More preferably, the grooves 259 have a width of 5 mm to 15 mm. There are preferably three to ten grooves 259 evenly spaced along the length. More preferably, there are four to eight grooves 259. The arms 250, 258 may have round screw holes 253. The screw holes 253 may span through the entire thickness of the arms 250, 258. The screw holes 253 may be internally threaded along the entire length. The screw holes 253 may be threaded partially along their length.

The cross bar 251 may be cylindrical. The cross bar 251 is preferably solid but may also be hollow. The cross bar 251 preferably has a diameter of 2 mm to 10 mm. More preferably, the diameter is 3 mm to 7 mm. The cross bar 251 preferably has a length of 30 mm to 100 mm. More preferably, the length is 55 mm to 75 mm. The cross bar 251 may have external threads. The cross bar 251 may be externally threaded along its entire length. The cross bar 251 may be partially threaded.

The nut 252 may be cylindrical. The nut 252 may have a round through hole, parallel with its axis. The internal surface of the nut 252 may have internal threads. The nut 252 may have internal threads along its entire length. The threads may be sized and shaped to mate with the external threads of the cross bar 251. The nut 252 may have a uniform outer diameter along its entire length. The nut 252 may have a variable outer diameter. The outer diameter of the nut 252 is preferably 5 mm to 25 mm. More preferably, the outer diameter is 12 mm to 20 mm.

The screw 260 may be a standard screw that is sized to fit the screw holes 253 and span the thickness of the arms 150, 158.

The impaction attachment 262 may be assembled by screwing the arms 150, 158 together with the screw 260. The screw 260 may serve as the axis of rotation. The cross bar 251 may be inserted into the second arm 258 with a pin 261. The pin 261 may be press fit, glued, or secured using any other attachment method. The cross bar 251 may threadably engage with the first arm 250. The cross bar 251 may be secured by tightening (threadably engaging) the nut 252 onto the end of the cross bar 251. The impaction attachment 262 may be stainless steel or any other metal. The impaction attachment 262 may be a polymer or ceramic.

FIG. 37A-37B shows an embodiment of a driver 280. FIGS. 37A and 37B each illustrate an embodiment with optional features, any of which may be optionally used or substituted with other features in other embodiments discussed herein. FIG. 37A shows a side view of an exemplary embodiment of a driver. FIG. 37B shows a cross-section view of an exemplary embodiment of a driver. The driver 280 may comprise a body 270 and a knob 271. The body 270 may have a first driving end 272 and a second driving end 276. The body 270 may be cylindrical. The body 270 may be any shape. The body 270 preferably has a length of 100 mm to 200 mm. More preferably, the body 270 length is 120 mm to 180 mm. The body 270 is preferably cannulated. The body 270 preferably has an inner diameter of 0.5 mm to 4.5 mm. More preferably, the inner diameter is 1 mm to 4 mm. The outer diameter of the body 270 may vary along its length. The outer diameter preferably ranges from 2 mm to 50 mm. More preferably, the other diameter ranges from 2 mm to 40 mm. The first driving end 272 may have a torx shape. The first driving end 272 may have a hexagonal shape. The first driving end 272 may have any shape that can be used as a driving element. The first driving end 272 may be slotted to be able to compress inwardly slightly and to provide a press fit with the receiving feature (not pictured). The second driving end 276 may have an engagement feature 273. The engagement feature 273 may be an extruded slot that may engage a slot head. The engagement feature 273 may be any shape. The body 270 may have a plurality of grooves 274 circumferentially about the body 273 and axially along the length. The grooves 274 may be ovular. The grooves 274 may be any shape. The grooves 274 may be sized and spaced to fill the surface and provide for easier handling. There may be a plurality of cutouts 275 on the body 270. The cutouts 275 may be located circumferentially around the body. The cutouts 275 are preferably 20 mm to 60 mm from the second driving end 276. There are preferably one to three cutouts 275.

The knob 271 may have a head 277 and a shaft 278. The head 277 may be cylindrical. The head 277 may be any shape. The head 277 may have a through hole through its center axis. The through hole preferably has a diameter of 1 mm to 8 mm. More preferably, the diameter is 1 mm to 6 mm. The head 277 preferably has a length of 10 mm to 20 mm. More preferably, the head 277 has a length of 12 mm to 18 mm. The head 277 preferably has an outer diameter of 10 mm to 35 mm. More preferably, the head 277 has an outer diameter of 15 mm to 30 mm. The head 277 may have a plurality of grooves 279 located circumferentially around its diameter to provide for easier handling. There are preferably four to twelve grooves 279 spaced evenly about the surface. More preferably, there are six to ten grooves 279 spaced evenly about the surface. The grooves 279 may be ovular in shape. The grooves 279 may be any shape. The shaft 278 may be cylindrical. The shaft 278 may be cannulated. The shaft 278 preferably has an inner diameter of 0.5 mm to 5.5 mm. More preferably, the inner diameter is 1 mm to 5 mm. The shaft 278 preferably has an outer diameter of 1 mm to 8 mm. More preferably, the outer diameter is 1 mm to 6 mm. The shaft 278 preferably has a length of 20 mm to 70 mm. More preferably, the shaft 278 has a length of 30 mm to 60 mm. The shaft 278 may be externally threaded at one end, partially along its length. The external threads may be sized to mate with the threads of a locking mechanism (not pictured). The non-threaded end of the shaft 278 may be disposed in the through hole of the head 277. The head 277 and shaft 278 may be manufactured together. The head 277 and shaft 278 may be joined by bonding, welding, press fit, or any other method for joining two components.

The driver 280 may be assembled so that the knob 271 head 277 is positioned in the body 270 cutouts 275 and the shaft 277 is disposed in the body 270 cannulation, with the threaded end of the shaft 277 extending past the second driving end 276 of the body 270. The driver 280 may be used to insert the locking mechanisms of any embodiment disclosed herein.

Figure 38A:
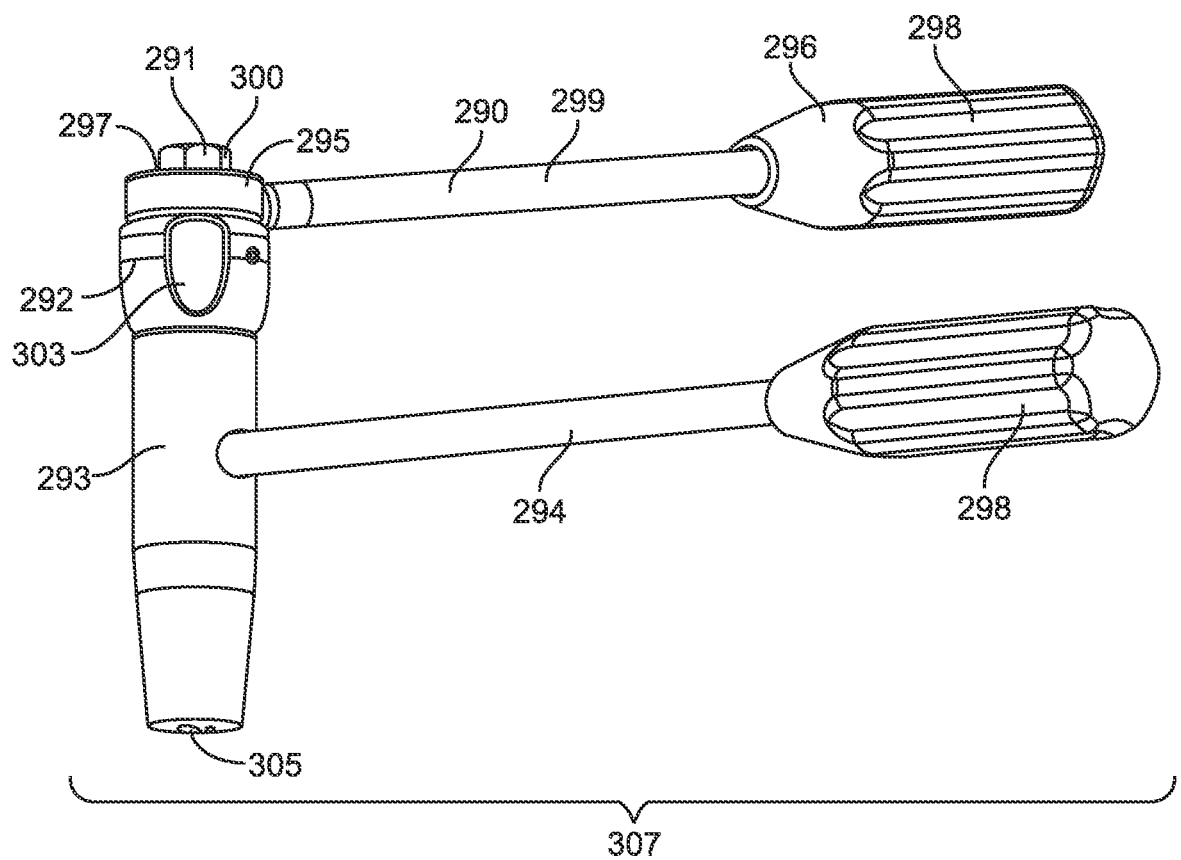
FIG. 38A shows a perspective view of an exemplary embodiment of a cutter.
Figure 38B:
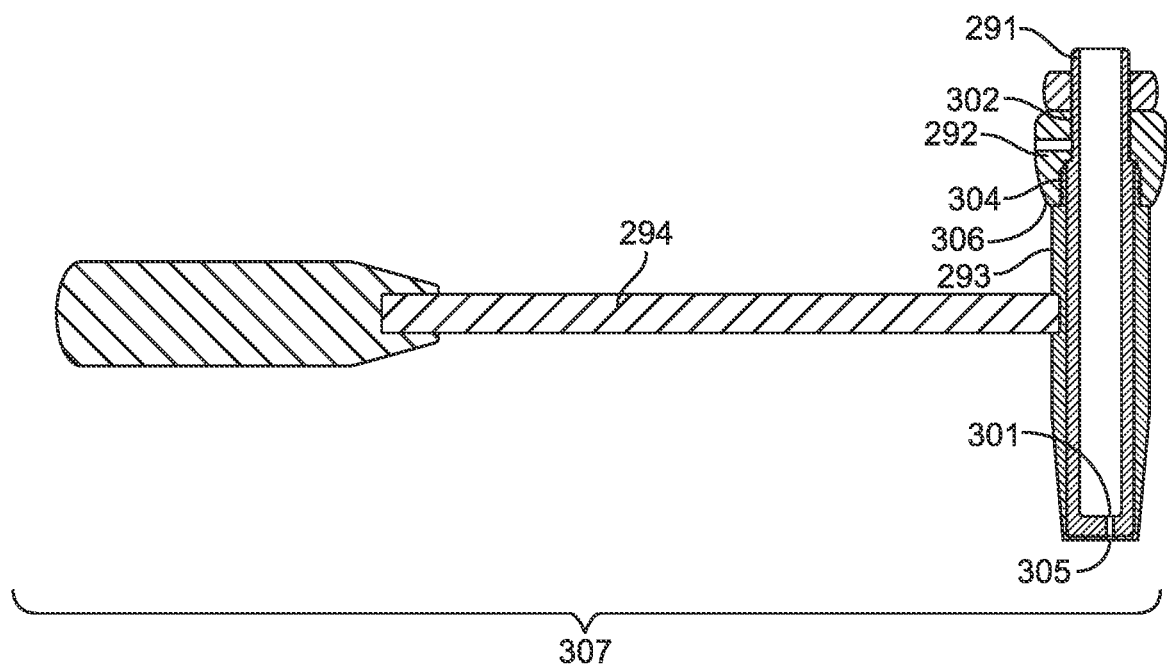
FIG. 38B shows a cross-section view of an exemplary embodiment of a cutter.

FIG. 38A shows a perspective view of an exemplary embodiment of a cutter. FIG. 38B shows a cross-section view of an exemplary embodiment of a cutter. FIGS. 38A and 38B each illustrate an embodiment with optional features, any of which may be optionally used or substituted with other features in other embodiments discussed herein. FIG. 38A and FIG. 38B illustrate an embodiment of a cutter 307 comprising a wrench 290, bolt 291, cap 292, body 293, and handle 294. The wrench 290 is an elongate member with a turning end 295, shaft 299, and a handle 296. The wrench 290 is preferably cylindrical in shape but may be any shape. The wrench 290 is preferably solid. The wrench 290 is preferably rigid. The wrench 290 preferably has a length of 100 mm to 400 mm. More preferably, the wrench 290 has a length of 200 mm to 300 mm. The wrench 290 may have a uniform diameter across its length. The wrench 290 may have a variable diameter across its length. The wrench 290 preferably has a diameter of 5 mm to 50 mm. More preferably, the wrench 290 has a diameter of 10 mm to 40 mm. The turning end 295 may have a through hole 297. The through hole 297 may be shaped as a hex to act as a driving mechanism. The through hole 297 may be any other shape. The turning end 295 and shaft 299 may be stainless steel. The turning end 295 and shaft 299 may be any metal, polymer, or ceramic. The handle 296 may have a plurality of grooves 298 located circumferentially around its diameter to provide for easier handling. There are preferably three to twelve grooves 298 spaced evenly about the surface. More preferably, there are five to ten grooves 298 spaced evenly about the surface. The grooves 298 may be ovular in shape. The grooves 298 may be any shape. The handle 296 may be radel or any polymer. The handle 296 may be a metal or ceramic. The handle 296 may be coupled to the shaft 299 by bonding, press fit, or any other process.

The bolt 291 is preferably a cylinder. The bolt 291 may have a driving shape 300 that spans partially across its length. The driving shape 300 may be a hex shape or any other shape. The driving shape 300 may mate with the through hole 297 on the wrench 290. The bolt 291 may have one or more round holes 301 that traverse the entire length of the bolt 291. The bolt 291 may be solid. The bolt 291 may be hollowed with the base remaining. The bolt 291 may be tapered on the non-driving shape 300 end. The bolt 291 may be stainless steel. The bolt 291 may be any metal, polymer, or ceramic.

The cap 292 is preferably cylindrical. The cap 292 may have a round through hole 302. The internal surface may be partially threaded 304. The cap 292 may have a plurality of grooves 303 located circumferentially around its diameter to provide for easier handling. There are preferably three to twelve grooves 303 spaced evenly about the surface. More preferably, there are three to ten grooves 303 spaced evenly about the surface. The grooves 303 may be ovular in shape. The grooves 303 may be any shape. The cap 292 may be stainless steel. The cap 292 may be any metal, polymer, or ceramic.

The body 293 is preferably cylindrical. The body 293 preferably has a length of 100 mm to 400 mm. More preferably, the body 293 has a length of 150 mm to 350 mm. The body 293 may have varying diameters across its length. The body 293 preferably has an outer diameter of 20 mm to 100 mm. More preferably, the body 293 has an outer diameter of 40 mm to 80 mm. The body 293 may be hollowed with the base remaining. The body 293 may be externally threaded 306 partially along its length. The body 293 may have a plurality of through holes 305. The plurality of through holes 305 may be aligned with the through holes 301 of the bolt 292. The body 293 may be stainless steel. The body 293 may be any metal, polymer, or ceramic.

The handle 294 is preferably cylindrical in shape but may be any shape. The handle 294 is preferably solid. The handle 294 is preferably rigid. The handle 294 preferably has a length of 100 mm to 400 mm. More preferably, the handle 294 has a length of 200 mm to 300 mm. The handle 294 may have a uniform diameter across its length. The handle 294 may have a variable diameter across its length. The handle 294 preferably has a diameter of 5 mm to 50 mm. More preferably, the handle 294 has a diameter of 10 mm to 40 mm. The handle 294 may have a plurality of grooves 298 located circumferentially around its diameter to provide for easier handling. There are preferably three to twelve grooves 298 spaced evenly about the surface. More preferably, there are five to ten grooves 298 spaced evenly about the surface. The grooves 298 may be ovular in shape. The grooves 298 may be any shape. The handle 294 may be the same material throughout or may have different materials. The handle 294 may be radel or any polymer. The handle 294 may be a metal or ceramic.

The handle 294 may be coupled to the body 293 by bonding, press fit, or any other process. The handle 294 may be coupled to the body 293 permanently. The cutter 307 may be assembled temporarily and taken apart. The bolt 291 may be inserted into the hollowed body 293. The bolt 291 may be constrained in the body 293 by threadably engaging the cap 292 to the body 293. The through holes 301, 305 on the body 293 and bolt 291 may be aligned so that an elongate member (not pictured) may be passed though. The wrench 290 may be placed over the bolt 291 and turned clockwise so that the holes 301, 305 transition from aligned to offset. The shear force on the elongate member may cause it to be cut.

Figure 39:
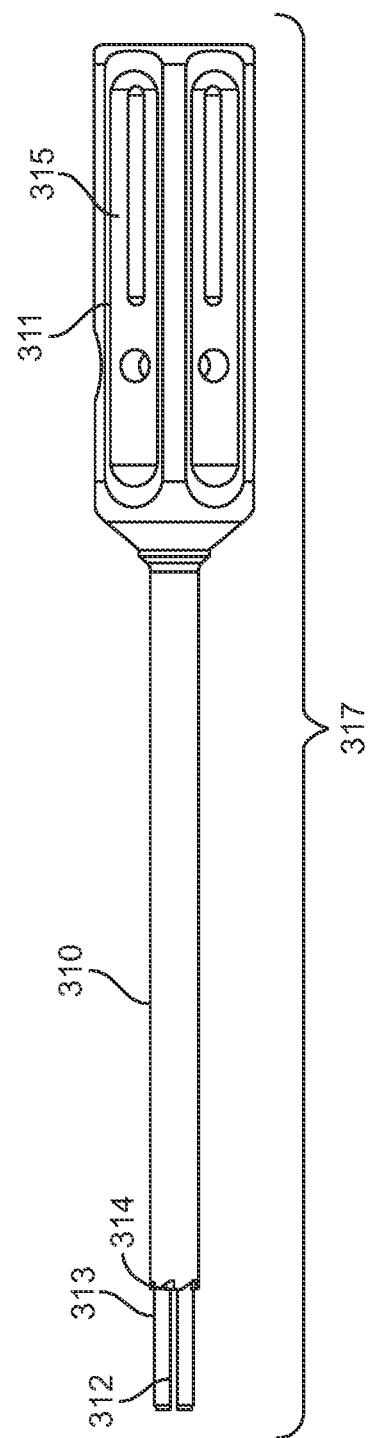
FIG. 39 shows a perspective view of an exemplary embodiment of a removal tool.

FIG. 39 shows a perspective view of an exemplary embodiment of a removal tool. FIG. 39 illustrates an embodiment with optional features, any of which may be optionally used or substituted with other features in other embodiments discussed herein. FIG. 39 is an embodiment of a removal tool 317 comprising a shaft 310, tabs 313, and handle 311. The shaft 310 is preferably tubular but may be any shape. The shaft 310 is preferably rigid. The shaft 310 preferably has a length of 50 mm to 200 mm. More preferably, the shaft 310 has a length of 100 mm to 150 mm. The shaft 310 preferably has an outer diameter of 5 mm to 20 mm. More preferably, the shaft 310 has an outer diameter of 5 mm to 15 mm. The shaft 310 preferably has an inner diameter of 3 mm to 17 mm. More preferably, the shaft 310 has an inner diameter of 3 mm to 12 mm. One end of the shaft 310 may have a reaming edge 314. The reaming edge 314 may have a jagged shape to ream bone.

The tab 313 preferably is tubular but may be any shape. The tab 313 preferably has a length of 60 mm to 210 mm. More preferably, the tab 313 has a length of 110 mm to 160 mm. The tab 313 preferably has an outer diameter of 3 mm to 17 mm. More preferably, the tab 313 has an outer diameter of 3 mm to 12 mm. The tab 313 preferably has an inner diameter of 2 mm to 16 mm. More preferably, the tab 313 has an inner diameter of 2 mm to 11 mm. One of the ends may have a plurality of slots 312 extending partially across its length located circumferentially around the tab 313. The slots 312 may allow the material in between to be flexible.

The handle 311 is preferably cylindrical and hollowed but may be any shape. The handle 311 preferably has a length of 30 mm to 100 mm. More preferably, the handle 311 has a length of 40 mm to 90 mm. The handle 311 preferably has an outer diameter of 10 mm to 30 mm. More preferably, the handle 311 has an outer diameter of 15 mm to 25 mm. The handle 311 preferably has an inner diameter of 3 mm to 10 mm. More preferably, the handle 311 has an inner diameter of 5 mm to 8 mm. The handle 311 may have a plurality of grooves 315 located circumferentially around its diameter to provide for easier handling. There are preferably three to twelve grooves 315 spaced evenly about the surface. More preferably, there are five to ten grooves 315 spaced evenly about the surface. The grooves 315 may be ovular in shape. The grooves 315 may be any shape. The handle 311 may be radel or any polymer. The handle 311 may be a metal or ceramic.

The tab 313 may be inserted into the shaft 310. The shaft 310 may be coupled to the handle 311. The shaft 310 may be threadably engaged with the handle 311 such that as it is unthreaded, the shaft 310 moves longitudinally. In use, the tab 313 may close around the locking mechanism (not pictured). A button on the handle 311 may be used to narrow the tab 313. The shaft 310 may move longitudinally so that the reaming edge 314 approaches the bone (not pictured). The handle 311 may be used to rotate the removal instrument 317 to ream the surrounding area. The handle 311 may be used to pull the locking mechanism and implant (not pictured) out of the bone.

FIGS. 40-47 illustrate an exemplary method for delivering the embodiment as described in FIG. 2 of an implant into a fractured metacarpal bone 500 of a patient. FIGS. 40-47 each illustrate an embodiment with optional features, any of which may be optionally used or substituted with other features in other embodiments discussed herein.

Figure 40:
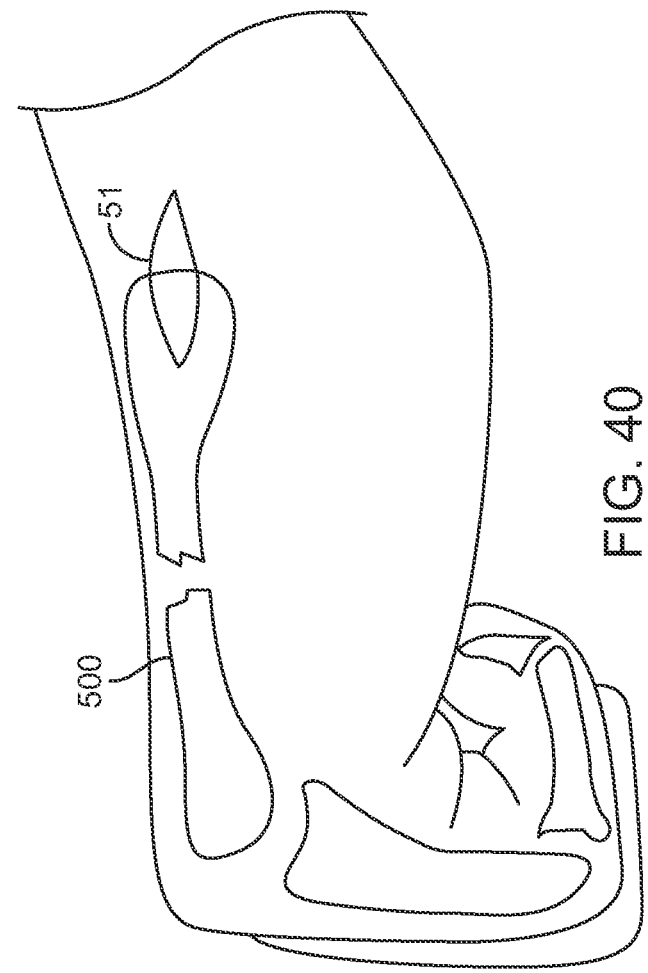
FIG. 40 shows a side view of an incision created to access a bone.

FIG. 40 shows a side view of an incision created to access a bone. In particular, FIG. 40 illustrates an incision 51 made at the proximal end of the fractured metacarpal bone 500 through tissue in the patient's hand to expose the bone.

Figure 41:
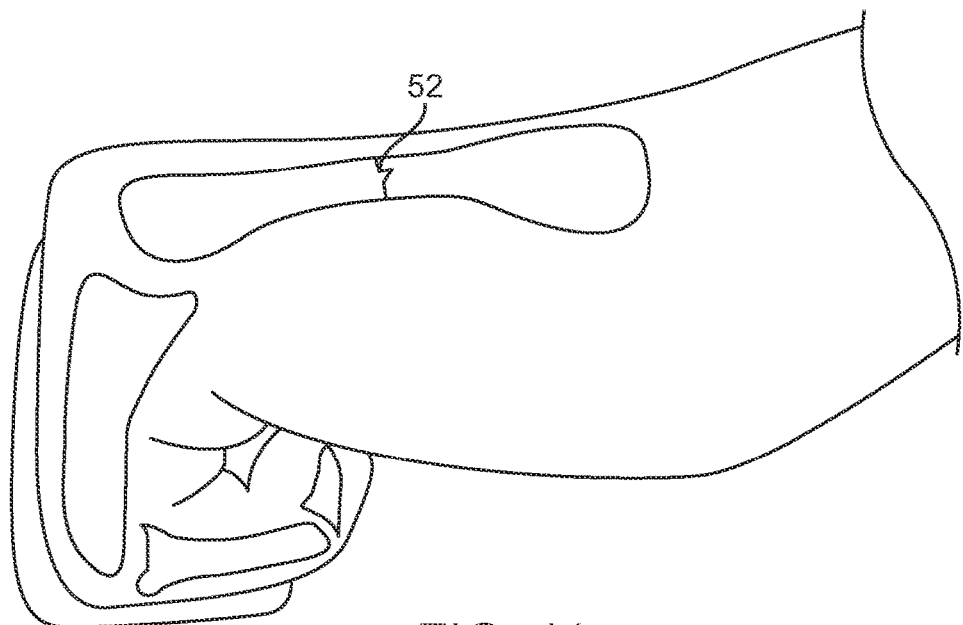
FIG. 41 shows a side view of a reduced fracture.

FIG. 41 shows a side view of a reduced fracture. In particular, FIG. 41 shows the reduction of a fracture 52 which can be done by axially retracting the fracture fragment and pushing it back in place, or other methods known to those skilled in the art.

Figure 42:
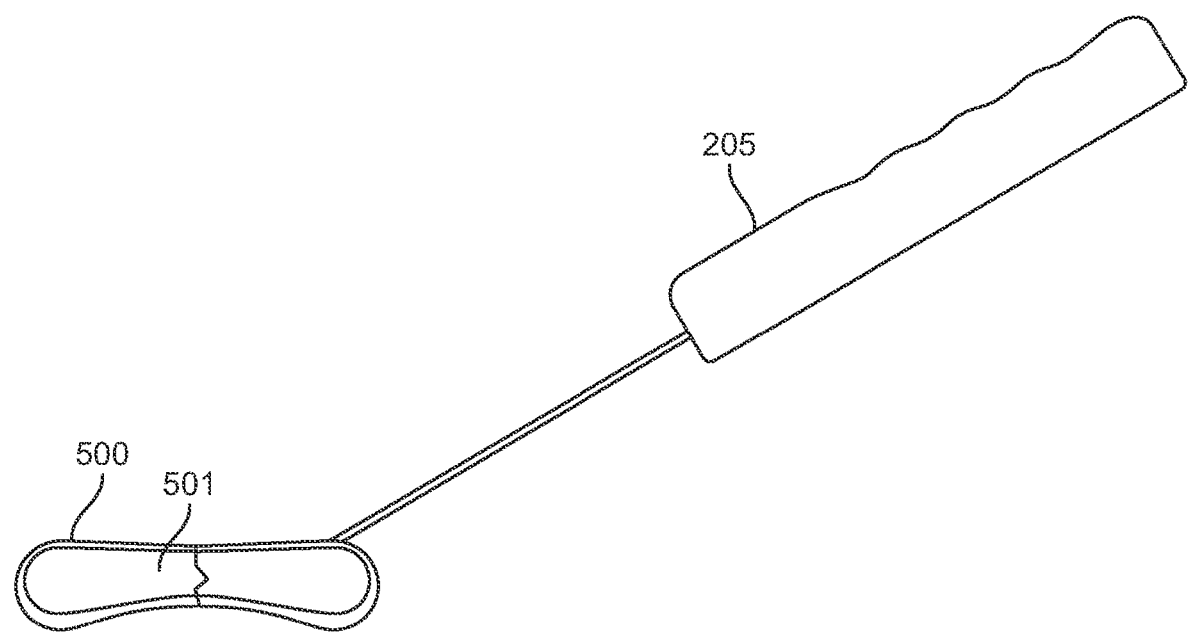
FIG. 42 shows a side view of an awl creating a hole in a bone to receive an implant.

FIG. 42 shows a side view of an awl creating a hole in a bone to receive an implant. In particular, FIG. 42 illustrates the use of an awl 205 passed through the incision (not pictured) to access the intramedullary canal 501 of metacarpal bone 500.

Figure 43:
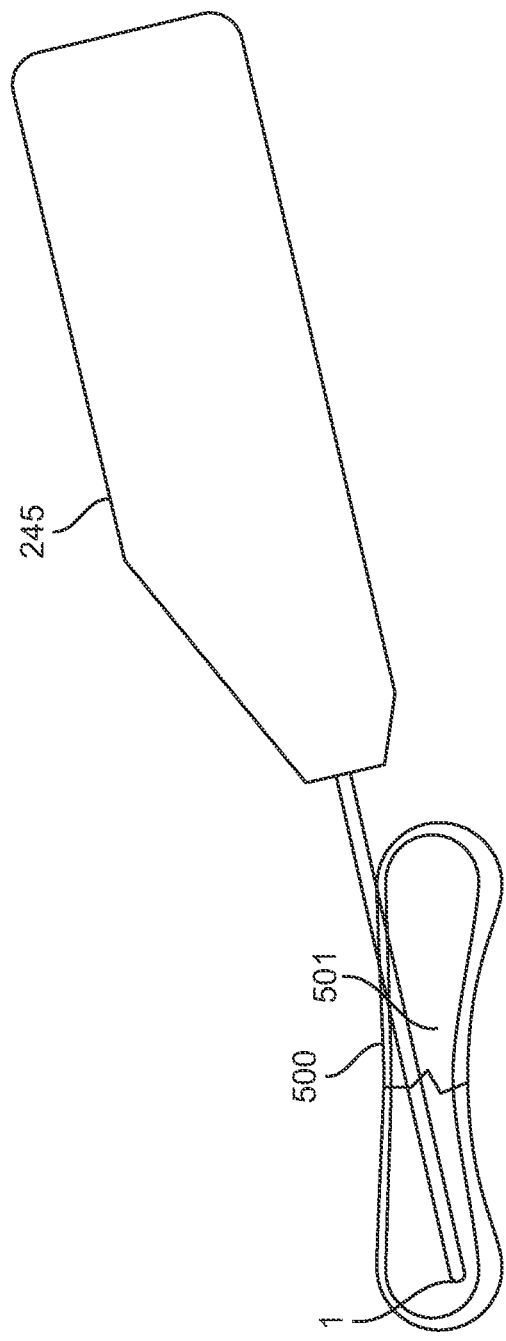
FIG. 43 shows a side view of an implant being inserted with the aid of an inserter.

FIG. 43 shows a side view of an implant being inserted with the aid of an inserter. In particular, FIG. 43 shows a side view of the insertion of the elongate member 1 into the intramedullary canal 501 of the metacarpal bone 500 with the aid of an inserter 245.

Figure 44:
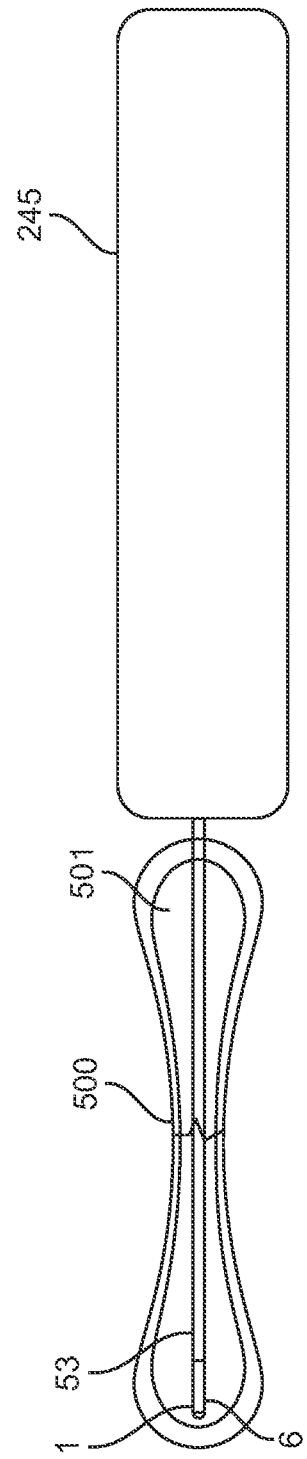
FIG. 44 shows a top view of an implant being inserted with the aid of an inserter.

FIG. 44 shows a top view of an implant being inserted with the aid of an inserter. In particular, FIG. 44 shows a top view of metacarpal bone 500 with inserter 245 and sheath 53 keeping elongate member 1 with distal end 6 in the compressed state within the intramedullary canal 501.

FIG. 45 shows a top view of an inserter retracting and an implant expanding. In particular, FIG. 45 shows a top view of metacarpal bone 500 with the retreat of inserter 245 after proximally retracting sheath 53 to allow for the radial expansion of the distal end 6 of elongate member 1 within in the intramedullary canal 501. The distal end 6 may expand as described in FIG. 2 to anchor to the bone. The inserter 245 and sheath 53 may be fully removed.

FIG. 46 shows a side view of a locking mechanism being driven into a long bone by a driver. In particular, FIG. 46 illustrates the use of a driving tool 50 to drive locking mechanism 2 into metacarpal cortical bone 500 in order to attach elongate member 1 to the bone 500 at both ends of the elongate member 1.

Figure 47:
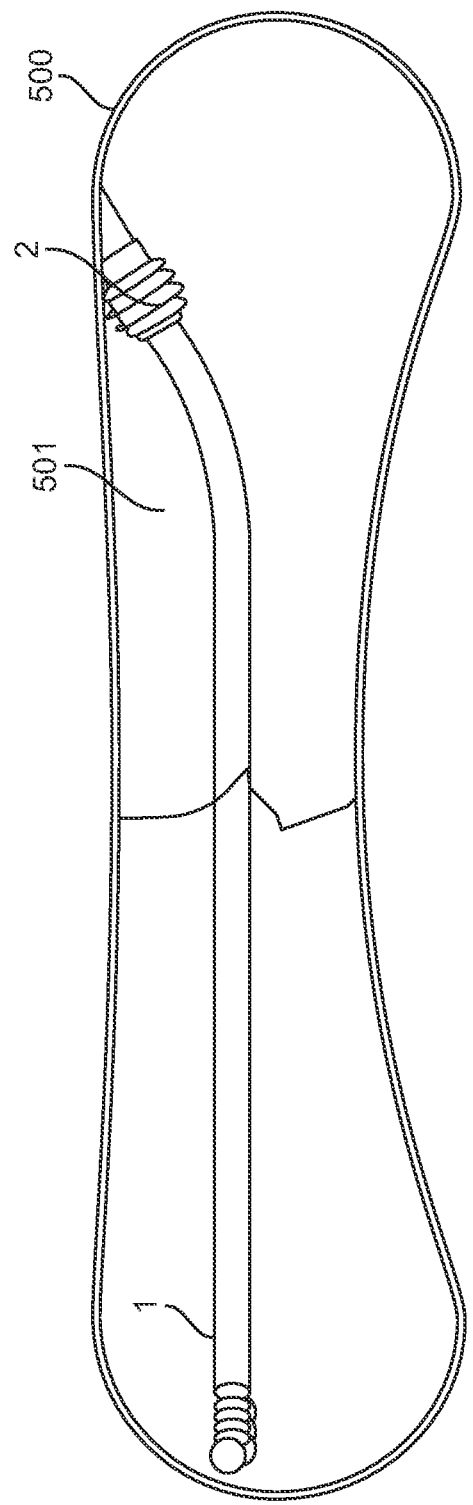
FIG. 47 shows a side view of an implant after the insertion of the locking mechanism.

FIG. 47 shows a side view of an implant after the insertion of the locking mechanism. In particular, FIG. 47 shows a final implant position in the intramedullary canal 501 of the metacarpal bone 500 such that elongate member 1 may be flush with the metacarpal bone 500 and the locking mechanism 2 is completely below the surface of metacarpal bone 500.

What is claimed is:

1. A method of delivering an implant into the intramedullary canal of a fractured long bone of a patient in an anterograde or retrograde manner, said method comprising:
   making an incision to access the fractured long bone;
   reducing and rotationally aligning the fractured long bone;
   accessing the intramedullary canal of the fractured long bone;
   inserting an elongate member of the implant into the intramedullary canal along a long axis of the bone;
   radially expanding a distal end of the elongate member to engage with walls of the intramedullary canal; and
   locking a locking mechanism at a proximal end of the implant to the bone wherein the locking mechanism comprises a bone component and a locking component, and
   wherein the locking component is configured to fit inside of the bone component.

2. The method of claim 1, wherein accessing the intramedullary canal comprises punching a hole through the bone with an awl instrument.

3. The method of claim 1, wherein accessing the intramedullary canal comprises drilling a hole through the bone.

4. The method of claim 2, wherein the bone is accessed at an angle between 15 and 45 degrees.

5. The method of claim 1, wherein inserting the implant into intramedullary canal is done with an inserter instrument.

6. The method of claim 5, wherein the inserter instrument comprises a reaming feature to clear a path through the intramedullary canal.

7. The method of claim 5, wherein the inserter instrument comprises a sheath to insert the implant in its unexpanded state.

8. The method of claim 5, wherein retracting the inserter instrument radially expands the distal end of the implant to engage with walls of the intramedullary canal.

9. The method of claim 5, wherein retracting the inserter instrument and implant further reduces the fractured long bone fracture.

10. The method of claim 5, wherein the inserter instrument is completely removed after the implant is placed in the intramedullary canal.

11. The method of claim 5, wherein a driver instrument couples the locking mechanism to the proximal end of the elongate member.

12. The method of claim 5, wherein a driver instrument attaches the locking mechanism to the proximal end of the bone.

13. The method of claim 1, wherein the implant is radially expanded manually.

14. The method of claim 13, wherein manual expansion comprises disposing a pin between a pair of arms and moving the pin proximally thereby causing the arms to flare radially outward.

15. The method of claim 13, wherein manual expansion comprises actuating a threaded mechanism thereby radially expanding the distal tip, wherein the actuating is performed outside of the bone.

16. The method of claim 1, wherein the implant is cut with a cutter instrument.

17. The method of claim 1, wherein the implant is cut to be flush with the outer surface of the bone.

18. The method of claim 1, wherein the distal end of the elongate member expands in the diaphysis.

19. The method of claim 1, wherein the distal end of the elongate member expands in the metaphysis.

20. The method of claim 1, wherein the distal end of the elongate member expands in the epiphysis.

21. The method of claim 1, wherein reducing the fractured long bone occurs after radially expanding the distal end of the elongate member.

22. The method of claim 21, wherein reducing the fractured long bone comprises manual manipulation of the elongate member.

23. A method of providing stability of a long bone fracture, the method comprising:
   positioning a monolithic elongate member substantially parallel to a longitudinal axis of a fractured long bone, the monolithic elongate member comprising a distal end, a proximal end, and a longitudinal axis; and
   fixating the monolithic elongate member to the fractured long bone using a locking screw mechanism,
   wherein the locking screw mechanism comprises a bone component and a locking component that are coupled together, wherein the locking screw mechanism is configured to receive the proximal end of the monolithic elongate member, wherein the bone component comprises a cannulated screw that is configured to receive the monolithic elongate member and that is configured to threadably engage the fractured long bone for fixation, and wherein the distal end of the monolithic elongate member comprises a distal tip that is expandable to become wider radially and is configured to engage the fractured long bone to anchor the distal end.

24. The method of claim 23, wherein the bone component and the locking component are configured to threadably engage.

25. The method of claim 23, wherein the bone component comprises an internal cannulation of a shape configured to mate with and compress the locking component.

26. The method of claim 23, wherein the distal end of the monolithic elongate member is naturally in its expanded state and is implanted with the expansion constrained.

27. The method of claim 23, wherein the distal end of the monolithic elongate member comprises shape memory material that is expanded through temperature properties of the material.

28. The method of claim 23, wherein the monolithic elongate member comprises one more through slots extending from the distal end proximally, configured to form two or more arms that can bend in an arcuate shape.

29. A method of providing stability of a long bone fracture, the method comprising:

positioning a monolithic elongate member substantially parallel to a longitudinal axis of a fractured long bone, the monolithic elongate member comprising a distal end, a proximal end, and a longitudinal axis; and fixating the monolithic elongate member to the fractured long bone using a locking screw mechanism, wherein the locking screw mechanism comprises a bone component and a locking component that are coupled together, wherein the locking screw mechanism is configured to receive the proximal end of the monolithic elongate member, wherein the bone component is configured to engage the bone, wherein the distal end comprises a distal tip that is expandable to become wider radially and is configured to engage the bone to anchor the distal end, and wherein the locking component is configured to fit inside the bone component and is cannulated to receive the monolithic elongate member.

30. The method of claim 29, wherein the locking component comprises one or more grasping features configured to interface with an internal cannulation of the bone component, causing the locking component to narrow and grasp the monolithic elongate member.

31. The method of claim 29, wherein the bone component comprises a cannulated screw that is configured to receive the monolithic elongate member and to threadably engage the bone for fixation.

* * * * *